US012161709B2

(12) United States Patent
Weissman et al.

(10) Patent No.: US 12,161,709 B2
(45) Date of Patent: *Dec. 10, 2024

(54) COMPOSITIONS FOR INDUCING AN IMMUNE RESPONSE AGAINST ZIKA VIRUS

(71) Applicant: The Trustees of the University of Pennsylvania, Philadelphia, PA (US)

(72) Inventors: Drew Weissman, Wynnewood, PA (US); Norbert Pardi, Philadelphia, PA (US); Michael Hogan, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,190

(22) Filed: Dec. 22, 2021

(65) Prior Publication Data

US 2022/0184201 A1    Jun. 16, 2022

Related U.S. Application Data

(63) Continuation of application No. 16/477,258, filed as application No. PCT/US2018/013270 on Jan. 11, 2018, now Pat. No. 11,241,490.

(60) Provisional application No. 62/444,931, filed on Jan. 11, 2017.

(51) Int. Cl.
| | |
|---|---|
| *A61K 39/12* | (2006.01) |
| *A61K 9/51* | (2006.01) |
| *A61P 31/14* | (2006.01) |
| *A61K 39/00* | (2006.01) |

(52) U.S. Cl.
CPC ............ *A61K 39/12* (2013.01); *A61K 9/5123* (2013.01); *A61P 31/14* (2018.01); *A61K 2039/53* (2013.01); *A61K 2039/545* (2013.01); *A61K 2039/55* (2013.01); *A61K 2039/55511* (2013.01); *A61K 2039/55555* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 2,856,420 | A | 10/1958 | Crawford, Jr. |
| 3,340,299 | A | 9/1967 | Weintraub |
| 3,931,430 | A | 1/1976 | Tada |
| 6,034,137 | A | 3/2000 | Belloni |
| 6,333,433 | B1 | 12/2001 | Banerjee |
| 6,458,381 | B1 | 10/2002 | Sourovoi |
| 8,278,036 | B2 | 10/2012 | Kariko |
| 8,748,089 | B2 | 6/2014 | Kariko |
| 8,835,108 | B2 | 9/2014 | Kariko |
| 9,352,042 | B2 | 5/2016 | Heyes |
| 9,737,619 | B2 | 8/2017 | Ansell |
| 9,738,593 | B2 | 8/2017 | Ansell |
| 9,750,824 | B2 | 9/2017 | Kariko |
| 9,795,566 | B2 | 10/2017 | Oya |
| 10,106,490 | B2 | 10/2018 | Du |
| 10,144,725 | B2 | 12/2018 | Brown |
| 10,166,298 | B2 | 1/2019 | Ansell |
| 10,221,127 | B2 | 3/2019 | Du |
| 10,723,692 | B2 | 7/2020 | Ansell |
| 2003/0153081 | A1 | 8/2003 | Tagawa |
| 2005/0032730 | A1 | 2/2005 | Von |
| 2005/0059624 | A1 | 3/2005 | Hoerr |
| 2005/0250723 | A1 | 11/2005 | Hoerr |
| 2006/0100177 | A1 | 5/2006 | Nishimura |
| 2006/0188490 | A1 | 8/2006 | Hoerr |
| 2008/0025944 | A1 | 1/2008 | Hoerr |
| 2009/0324584 | A1 | 12/2009 | Hoerr |
| 2010/0189729 | A1 | 7/2010 | Hoerr |
| 2010/0203076 | A1 | 8/2010 | Fotin-Mleczek |
| 2010/0291156 | A1 | 11/2010 | Barner |
| 2010/0305196 | A1 | 12/2010 | Probst |
| 2011/0250225 | A1 | 10/2011 | Fotin-Mleczek |
| 2011/0256175 | A1 | 10/2011 | Hope |
| 2011/0300205 | A1 | 12/2011 | Geall |
| 2011/0305770 | A1 | 12/2011 | Zhao |
| 2012/0021043 | A1 | 1/2012 | Kramps |
| 2012/0276209 | A1 | 11/2012 | Cullis |
| 2013/0129754 | A1 | 5/2013 | Thess |
| 2013/0259879 | A1 | 10/2013 | Baumhof |
| 2013/0261172 | A1 | 10/2013 | Kariko |

(Continued)

FOREIGN PATENT DOCUMENTS

| | | |
|---|---|---|
| EP | 1083232 A1 | 3/2001 |
| EP | 2567951 | 3/2013 |

(Continued)

OTHER PUBLICATIONS

Semple et al., 2010, "Rational design of cationic lipids for siRNA delivery." Nat Biotechnol., 28(2):172-176.

Szebeni et al., "Activation of complement by therapeutic liposomes and other lipid excipient-based therapeutic products: Prediction and prevention," Advanced Drug Delivery Reviews 63:1020-1030, 2011.

(Continued)

*Primary Examiner* — Nicole Kinsey White

(74) *Attorney, Agent, or Firm* — Riverside Law LLP

(57) ABSTRACT

The present invention relates to compositions and methods for inducing an adaptive immune response against Zika virus (ZIKV) in a subject. In certain embodiments, the present invention provides a composition comprising a nucleoside-modified nucleic acid molecule encoding a ZIKV antigen, adjuvant, or a combination thereof. For example, in certain embodiments, the composition comprises a vaccine comprising a nucleoside-modified nucleic acid molecule encoding a ZIKV antigen, adjuvant, or a combination thereof.

23 Claims, 11 Drawing Sheets

Specification includes a Sequence Listing.

(56) References Cited

U.S. PATENT DOCUMENTS

| | | |
|---|---|---|
| 2013/0266640 A1 | 10/2013 | De Fougerolles |
| 2013/0280283 A1 | 10/2013 | Lorenz |
| 2013/0280305 A1 | 10/2013 | Kuboyama |
| 2013/0295043 A1 | 11/2013 | Kallen |
| 2013/0336998 A1 | 12/2013 | Kallen |
| 2014/0323548 A1 | 10/2014 | Budzik |
| 2015/0037326 A1 | 2/2015 | Butler-Ransohoff |
| 2015/0050302 A1 | 2/2015 | Thess |
| 2015/0057340 A1 | 2/2015 | Thess |
| 2015/0093413 A1 | 4/2015 | Thess |
| 2015/0118183 A1 | 4/2015 | Baumhof |
| 2015/0118264 A1 | 4/2015 | Baumhof |
| 2015/0165006 A1 | 6/2015 | Thess |
| 2015/0184195 A1 | 7/2015 | Thess |
| 2015/0203446 A1 | 7/2015 | Manoharan |
| 2015/0218554 A1 | 8/2015 | Thess |
| 2015/0306249 A1 | 10/2015 | Baumhof |
| 2015/0376115 A1 | 12/2015 | Ansell |
| 2016/0038612 A1 | 2/2016 | Hoge |
| 2016/0130345 A1 | 5/2016 | Fotin-Mleczek |
| 2016/0166668 A1 | 6/2016 | Kallen |
| 2016/0166678 A1 | 6/2016 | Kallen |
| 2016/0166710 A1 | 6/2016 | Baumhof |
| 2016/0166711 A1 | 6/2016 | Schnee |
| 2016/0168207 A1 | 6/2016 | Kramps |
| 2016/0168227 A1 | 6/2016 | Kallen |
| 2016/0235864 A1 | 8/2016 | Schlake |
| 2016/0304883 A1 | 10/2016 | Grund |
| 2016/0361411 A1 | 12/2016 | Gindy |
| 2016/0376224 A1 | 12/2016 | Du |
| 2017/0029847 A1 | 2/2017 | Thess |
| 2017/0119904 A1 | 5/2017 | Ansell |
| 2017/0157268 A1 | 6/2017 | Ansell |
| 2017/0252430 A1 | 9/2017 | Fotin-Mleczek |
| 2017/0283367 A1 | 10/2017 | Ansell |
| 2017/0326225 A1 | 11/2017 | Rauch |
| 2018/0044687 A1 | 2/2018 | Thess |
| 2018/0125952 A1 | 5/2018 | Fotin-Mleczek |
| 2018/0126003 A1 | 5/2018 | Hoerr |
| 2018/0148727 A1 | 5/2018 | Grund |
| 2018/0214537 A1 | 8/2018 | Mutzke |
| 2018/0237786 A1 | 8/2018 | Schlake |
| 2018/0296663 A1 | 10/2018 | Hipp |
| 2018/0303925 A1 | 10/2018 | Weissman |
| 2018/0312545 A1 | 11/2018 | Baumhof |
| 2019/0022247 A1 | 1/2019 | Ansell |
| 2019/0024096 A1 | 1/2019 | Schmid |
| 2019/0160164 A1 | 5/2019 | Rauch |
| 2019/0270697 A1 | 9/2019 | Ansell |
| 2019/0274968 A1 | 9/2019 | Weissman |
| 2019/0314524 A1 | 10/2019 | Ansell |
| 2019/0359556 A1 | 11/2019 | Du |
| 2020/0046838 A1 | 2/2020 | Ansell |
| 2020/0121809 A1 | 4/2020 | Hope |
| 2020/0163878 A1 | 5/2020 | Baumhof |
| 2020/0172472 A1 | 6/2020 | Du |
| 2020/0283372 A1 | 9/2020 | Du |
| 2021/0107861 A1 | 4/2021 | Ansell |

FOREIGN PATENT DOCUMENTS

| | | |
|---|---|---|
| EP | 3289083 | 3/2018 |
| JP | 2001338416 | 12/2001 |
| JP | 5331118 | 12/2010 |
| WO | 1987007183 | 12/1987 |
| WO | 1997003939 | 2/1997 |
| WO | 1999005094 | 2/1999 |
| WO | 2000030444 | 6/2000 |
| WO | 2003053409 | 7/2003 |
| WO | 2005060934 | 7/2005 |
| WO | 2006138380 A2 | 12/2006 |
| WO | 2007024708 | 3/2007 |
| WO | 2011143230 | 11/2011 |
| WO | 2011153493 | 12/2011 |
| WO | 2012016184 | 2/2012 |
| WO | 2012068176 | 5/2012 |
| WO | 2013016058 | 1/2013 |
| WO | 2013086373 | 6/2013 |
| WO | 2013143555 | 10/2013 |
| WO | 2014028487 | 2/2014 |
| WO | 2014160243 | 10/2014 |
| WO | 2014160284 | 10/2014 |
| WO | 2015164674 A1 | 10/2015 |
| WO | 2015177752 A1 | 11/2015 |
| WO | 2015199952 | 12/2015 |
| WO | 2016145149 | 9/2016 |
| WO | 2016176330 | 11/2016 |
| WO | 2016210127 | 12/2016 |
| WO | 2017015463 | 1/2017 |
| WO | 2017021546 | 2/2017 |
| WO | 2017048770 | 3/2017 |
| WO | 2017049245 | 3/2017 |
| WO | 2017070624 A1 | 4/2017 |
| WO | 2017075531 A1 | 5/2017 |
| WO | 2017140905 | 8/2017 |
| WO | 2017173054 | 10/2017 |
| WO | 2017182634 | 10/2017 |
| WO | 2018191657 | 10/2018 |

OTHER PUBLICATIONS

Szebeni et al., "Complement activation as a bioequivalence issue relevant to the development of generic liposomes and other nanoparticulate drugs," Biochemical and Biophysical Research Communications 468:490-497, 2015.

Szebeni, "Complement activation-related pseudoallergy: A stress reaction in blood triggered by nanomedicines and biologicals," Molecular Immunology 61:163-173, 2014.

Tam et al., "Advances in Lipid Nanoparticles for siRNA Delivery," Pharmaceutics 5:498-507, 2013.

Tam et al., 2013, "Small molecule ligands for enhanced intracellular delivery of lipid nanoparticle formulations of siRNA." Nanomedicine, 9(5): 665-74.

Tomokazu Yoshimura et al., Journal of Oleo Science, (Jan. 1, 2013), vo. 62, No. 4, doi: 10.5650/jos.62.213, ISSN 1345-8957, pp. 213-221.

Torrecilla, J et al., "Lipid Nanoparticles as Carriers for RNAi against Viral infections: Current Status and Future Perspectives.", BioMed Research International., (Aug. 12, 2014), vol. 2014, No. 2014, pp. 1-18, XP055326069.

Vanderah et al, "Oligo(ethylene oxide) Self-Assembled Monolayers with Self-Limiting Packing Densities for the Inhibition of Nonspecific Protein Adsorption," Langmuir 25(9):5026-5030, 2009.

Wang et al., 2009, "Efficient Assembly and Secretion of Recombinant Subviral Particles of the Four Dengue Serotypes Using Native prM and E Proteins," PLoS One 4: e8325, 13 pages.

Weissman et al., 2000, "HIV Gag mRNA Transfection of Dendritic Cells (DC) Delivers Encoded Antigen to MHC Class I and II Molecules, Causes DC Maturation, and Induces a Potent Human In Vitro Primary Immune Response," J Immunol, 165: 4710-4717.

Weissman et al., 2013, "HPLC purification of in vitro transcribed long RNA," Methods Mol Biol, 969: 43-54.

Weissman, 2015, "mRNA transcript therapy," Expert Rev Vaccines, 14: 265-281.

Xue et al., "Lipid-Based Nanocarriers for RNA Delivery," Current Pharmaceutical Design 21:3140-3147, 2015.

"Zika virus isolate 05211 polyprotein gene, partial cds", Nucleotide, (Jun. 1, 2016), Database accession No. KU758869.1, URL: NCBI, XP055512677, 2 pages.

Abbink et al., 2016, "Protective Efficacy of Multiple Vaccine Platforms Against Zika Virus Challenge in Rhesus Monkeys," Science, 353, 1129-1132.

Akinc et al., "A combinatorial library of lipid-like materials for delivery of RNAi therapeutics," Nature Biotechnology 26(5):561-569, May 2008.

Akinc et al., 2010, "Targeted delivery of RNAi therapeutics with endogenous and exogenous ligand-based mechanisms." Mol Ther., 18(7): 1357-1364.

Alabi C.A, et al., PNAS, vol. 110, No. 32, doi: 1-.1073/PNAS. 1306529110, ISSN 0027-8424, pp. 12881-12886, Aug. 6, 2013.

(56) References Cited

OTHER PUBLICATIONS

Alexandros N. Alexidis, et al., Journal of Pharmacy and Pharmacology, (Mar. 28, 1995), vol. 47, No. 2, doi: 10.1111/j.2042-7158.1995.tb05765.X, ISSN 0022-3573, pp. 131-137.
Anderson et al., 2010, "Incorporation of pseudouridine into mRNA enhances translation by diminishing PKR activation." Nucleic Acids Res 38:5884-5892.
Anderson et al., 2011. Nucleoside modifications in RNA limit activation of 2'-5'-oligoadenylate synthetase and increase resistance to cleavage by RNase L. Nucleic Acids Research 39:9329-9338.
Andries et al., "N1-methylpseudouridine-incorporated mRNA outperforms pseudouridine-incorporated mRNA by providing enhanced protein expression and reduced immunogenicity in mammalian cell lines and mice," Journal of Controlled Release, vol. 217, Nov. 10, 2015, pp. 337-344.
Ansell et al., "Novel Lipids and Lipid Nanoparticle Formulations for Delivery of Nucleic Acids," U.S. Appl. No. 17/317,517, filed May 11, 2021.
Baronti et al, "Complete Coding Sequence of Zika Virus from a French Polynesia Outbreak in 2013," Genome Announc. 2014;2(3):e00500-14. Published Jun. 5, 2014. doi:10.1128/genomeA.00500-14, 2 pages.
Basha et al., 2011, "Influence of cationic lipid composition on gene silencing properties of lipid nanoparticle formulations of siRNA in antigen-presenting cells." Mol Ther, 19(12): 2186-2200.
Belliveau et al., 2012, "Microfluidic Synthesis of Highly Potent Limit-size Lipid Nanoparticles for In Vivo Delivery of siRNA." Mol Ther Nucleic Acids, 1: e37, 9 pages.
Bhattacharya et al., "Synthesis, Thermotropic Behavior, and Permeability Properties of Vesicular Membranes Composed of Cationic Mixed-Chain Surfactants," Langmuir 11:4748-4757, 1995.
Cattanach C.J, et al., Journal of the Chemical Society C: Organic, (Jan. 1, 1968), doi: 10.1039/j39680001235, ISSN 0022-4852, 9 pages.
Chen et al., "Influence of particle size on the in vivo potency of lipid nanoparticle formulations of siRNA," Journal of Controlled Release 235:236-244, 2016.
Cook CJ, et al., "Synthesis and characterization of cis-dioxomolybdenum(VI) complexes with sterically bulky tripodal tetradentate ligands," Onorganica Chimica Acta (Jan. 1, 1988), pp. 81-87.
D.N. Nguyen et al: "Lipid-derived nanoparticles for immunostimulatory RNA adjuvant delivery", Proceedings of the National Academy of Sciences of the United States of America, vol. 109, No. 14, Apr. 3, 2012 (Apr. 4, 2012), pp. E797-E803.
Dawes et al., "Research and development of Zika virus vaccines", npj Vaccines, (Jul. 28, 2016), vol. 1, No. 16007, pp. 1-7, XP055331389.
Dowd et al., 2016, "Rapid Development of a DNA Vaccine for Zika Virus," Science, 354, 237-240.
Durbin et al., "RNAs Containing Modified Nucleotides Fail to Trigger RIG-I Conformational Changes for Innate Immune Signaling," mBio 7(5):e00833-16, 2016 (11 pages).
Ernsting et al., "Factors controlling the pharmacokinetics, biodistribution and intratumoral penetration of nanoparticles," Journal of Controlled Release 172:782-794, 2013.
Falcone et al., "Both the 5' Untranslated Region and the Sequences Surrounding the Start Site Contribute to Efficient Initiation of Translation In Vitro," Molecular and Cellular Biology 11(5):2656-2664, 1991.
Frish, et al.; "A New Triantennary Galatose-Targeted PEGylated Gene Carrier, Characterization of Its Complex with DNA, and Transfection of Hepatoma Cells", Bioconjugate Chem., 2004, vol. 15, p. 754-764.
Han et al., "Synthesis and Properties of Di-Chain Esterquat Surfactants," J. Surfact Deterg. 18: 91-95, 2015.
Hekele et al., "Rapidly produced SAM® vaccine against H7N9 influenza is immunogenic in mice," Emerging Microbes and Infections 2:e52, 2013 (7 pages).
Jayaraman, M et al., "Maximizing the Potency of siRNA Lipid Nanoparticles for Hepatic Gene Silencing In Vivo.", Angewandte Chemie, (Jul. 10, 2012), vol. 51, No. 34, pp. 8529-8533, XP055063645.
Karikó et al., "Incorporation of Pseudouridine Into mRNA Yields Superior Nonimmunogenic Vector With Increased Translational Capacity and Biological Stability," Mol Ther, vol. 16, Issue 11, Nov. 2008, pp. 1833-1840.
Karikó et al., "Suppression of RNA Recognition by Toll-like Receptors: The Impact of Nucleoside Modification and the Evolutionary Origin of RNA," Immunity, Aug. 2005, vol. 23, 165-175.
Kariko et al., 2011. Generating the optimal mRNA for therapy: HPLC purification eliminates immune activation and improves translation of nucleosidemodified, protein-encoding mRNA. Nucleic Acids Research 39(21):e142, pp. 1-10.
Karikó et al., 2012, "Increased Erythropoiesis in Mice Injected with Submicrogram Quantities of Pseudouridine-containing mRNA Encoding Erythropoietin." Mol Ther 20:948-953.
Kathryn A Whitehead et al: "Synergistic Silencing: Combinations of Lipid-like Materials for Efficacious siRNA Delivery", Molecular Therapy, vol. 19, No. 9, Sep. 1, 2011 (Sep. 1, 2011), pp. 1688-1694.
Larocca et al., 2016, "Vaccine protection against Zika virus from Brazil," Nature, 536: 474-478.
Lazear et al., 2016, "A Mouse Model of Zika Virus Pathogenesis," Cell Host Microbe, 19: 720-730.
Lee et al., 2012, "Lipid nanoparticle siRNA systems for silencing the androgen receptor in human prostate cancer in vivo." Int J Cancer., 131(5): E781-90.
Leroueil et al., "Wide Varieties of Cationic Nanoparticles Induce Defects in Supported Lipid Bilayers," Nano Letters 8(2):420-424, 2008.
Leung et al., "Microfluidic Mixing: A General Method for Encapsulating Macromolecules in Lipid Nanoparticle Systems," J. Phys. Chem. B 119:8698-8706, 2015.
Leung et al., 2012, "Lipid Nanoparticles Containing siRNA Synthesized by Microfluidic Mixing Exhibit an Electron-Dense Nanostructured Core." J Phys Chem C Nanomater Interfaces, 116(34): 18440-18450.
Luis A Brito et al: "A Cationic Nanoemulsion for the Delivery of Next-generation RNA Vaccines", Molecular Therapy, vol. 22, No. 12, Jul. 16, 2014 (Jul. 16, 2014) pp. 2118-2129.
Maier et al., 2013, "Biodegradable lipids enabling rapidly eliminated lipid nanoparticles for systemic delivery of RNAi therapeutics." Mol Ther., 21(8): 1570-1578, XP055551712, ISSN: 1525-0016.
Masuda et al., "Envelope-type lipid nanoparticles incorporating a short PEG-lipid conjugate for improved control of intracellular trafficking and transgene transcription," Biomaterials 30:4806-4814, 2009.
Minor, 2015, "Live attenuated vaccines: Historical successes and current challenges," Virology, 479-480: 379-392.
Mui et al., 2013, "Influence of Polyethylene Glycol Lipid Desorption Rates on Pharmacokinetics and Pharmacodynamics of siRNA Lipid Nanoparticles." Mol Ther Nucleic Acids. 2, e139, 8 pages.
Muthumani et al. "In vivo protection against ZIKV infection and pathogenesis through passive antibody transfer and active immunisation with a prMEnv DNA vaccine," Npj Vaccines (2016) 1, 16021, 11 pages.
Pardi et al., "Expression kinetics of nucleoside-modified mRNA delivered in lipid nanoparticles to mice by various routes," Journal of Controlled Release vol. 217, Nov. 10, 2015, pp. 345-351.
Petsch et al., "Protective efficacy of in vitro synthesized, specific mRNA vaccines against influenza A virus infection," Nature Biotechnology 30:1210-1216, 2012.
Rajesh et al., "Dramatic Influence of the Orientation of Linker between Hydrophilic and Hydrophobic Lipid Moiety in Liposomal Gene Delivery," Journal of the American Chemical Society 129(37):11408-11420, 2007.
Sahin et al., "mRNA-based therapeutics—developing a new class of drugs," Nature Reviews Drug Discovery vol. 13, pp. 759-780(2014).

(56) References Cited

OTHER PUBLICATIONS

Schnee et al., "An mRNA Vaccine Encoding Rabies Virus Glycoprotein Induces Protection against Lethal Infection in Mice and Correlates of Protection in Adult and Newborn Pigs," PLoS Negl. Trop. Dis. 10(6):e0004746, 2016, 20 pages.

Schnirring L., "Zika mRNA vaccine enters clinical trial; Angola reports cases", CIDRAP—Center for Infectious Disease Research and Policy, (Jan. 10, 2017), p. 1, URL: http://www.cidrap.umn.edu/news-perspective/2017/01/zika-mrna-vaccine-enters- clinical-trial-angola-reports-cases, (Mar. 20, 2018), XP055512667.

COMPOSITIONS FOR INDUCING AN IMMUNE RESPONSE AGAINST ZIKA VIRUS

CROSS-REFERENCE TO RELATED APPLICATIONS

This application a Continuation of U.S. Pat. No. 11,241,490 issued Feb. 8, 2022 which was a U.S. national phase application filed under 35 U.S.C. § 371 claiming priority to International Patent Application No. PCT/US18/13270, filed Jan. 11, 2018, which is entitled to priority under 35 U.S.C. § 119 (e) to U.S. Provisional Patent Application No. 62/444,931 filed Jan. 11, 2017, the contents of which are incorporated by reference herein in their entirety.

STATEMENT REGARDING FEDERALLY SPONSORED RESEARCH OR DEVELOPMENT

This invention was made with government support under AI050484, AI058607, AI100645, and AI084860 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "046483-6154-01US_SequenceListing.txt"; created on Jul. 11, 2019, and 9,898 bytes in size, is hereby incorporated by reference.

BACKGROUND OF THE INVENTION

Zika virus (ZIKV), first identified in 1947 (Dick et al., 1952, Trans R Soc Trop Med Hyg, 46: 509-520), is a flavivirus that has recently been associated with microcephaly and other birth defects in newborns and Guillain-Barré syndrome in adults (Pierson and Graham, 2016, Cell, 625-631). Effective vaccines have been approved for other closely related flaviviruses, including yellow fever, Japanese encephalitis, and dengue viruses (Beck and Barrett, 2015, Expert Rev Vaccines, 14: 1479-1492; Jarmer et al., 2014, J Virol, 88: 13845-13857; Guy and Jackson, 2016, Nat Rev, Microbiol, 14: 45-54), but vaccine candidates for ZIKV have only recently been developed (Larocca et al., 2016, Nature, 536: 474-478; Abbink et al., 2016, Science, 353, 1129-1132; Dowd et al., 2016, Science, 354, 237-240). Larocca and colleagues generated a purified inactivated virus vaccine and a plasmid DNA vaccine that induced complete protection in mice from ZIKV infection (Larocca et al., 2016, Nature, 536: 474-478). The same laboratory also demonstrated that these vaccine platforms and a rhesus adenovirus serotype 52 vector (RhAd52) elicited complete protection against ZIKV in non-human primates (NHPs) (Abbink et al., 2016, Science, 353, 1129-1132). Most recently, Dowd and colleagues described two plasmid DNA vaccines that induced potent immune responses after two immunizations, which protected mice and NHPs from ZIKV infection (Dowd et al., 2016, Science, 354, 237-240). The ideal vaccine is safe and induces protective immunity after a single immunization, regardless of prior serologic history. Of the candidate Zika vaccines described to date, only the RhAd52 platform has been shown to confer protection after a single immunization in NHPs; however, the efficacy of this rhesus adenovirus vector in humans is currently undefined.

Additionally, pre-existing immunity to adenovirus serotypes can limit the efficacy of such vectors (Ledgerwood et al., 2010, Vaccine, 29: 304-313; Sumida et al., 2004, J Virol, 78: 2666-2673), and low neutralizing titers to rhesus adenoviruses, including RhAd52, have been detected in humans (Abbink et al., 2015, J Virol, 89: 1512-1522).

Thus, there is a need in the art for improved compositions and methods to treat and prevent ZIKV infection. The present invention satisfies this unmet need.

SUMMARY OF THE INVENTION

In one aspect, the present invention provides a composition for inducing an immune response against Zika virus (ZIKV) in a subject, the composition comprising at least one isolated nucleoside-modified RNA encoding at least one ZIKV antigen.

In one embodiment, the at least one isolated nucleoside-modified RNA comprises pseudouridine. In one embodiment, the at least one isolated nucleoside-modified RNA comprises 1-methyl-pseudouridine. In one embodiment, the at least one isolated nucleoside-modified RNA is a purified nucleoside-modified RNA.

In one embodiment, the at least one ZIKV antigen comprises at least one ZIKV antigen selected from the group consisting of envelope (E) protein, pre-membrane (prM) protein, membrane (M) protein, and capsid (C) protein. In one embodiment, the composition of claim 5, wherein the at least one ZIKV antigen comprises prM and E proteins. In one embodiment, the at least one ZIKV antigen comprises a signal peptide from MHC class II.

In one embodiment, the at least one ZIKV antigen comprises an amino acid sequence comprising SEQ ID NO: 2. In one embodiment, the at least one nucleoside-modified RNA comprises a nucleotide sequence comprising SEQ ID NO: 1. In one embodiment, the composition is a vaccine. In one embodiment, the composition further comprises an adjuvant. In one embodiment, the at least one nucleoside-modified RNA further encodes at least one adjuvant.

In one embodiment, the composition comprises a lipid nanoparticle (LNP). In one embodiment, the at least one nucleoside-modified RNA is encapsulated within the LNP. In one embodiment, the LNP comprises a compound having a structure of Formula (I):

$$\text{(I)}$$

or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In one embodiment, the LNP comprises a compound having a structure of Formula (II):

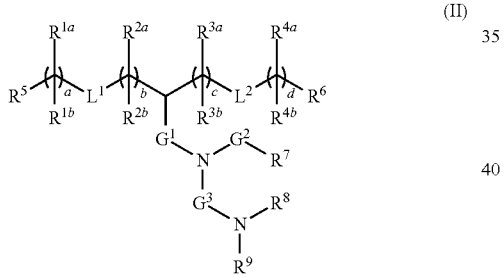

(II)

or a pharmaceutically acceptable salt, tautomer, prodrug or stereoisomer thereof, wherein:

$L^1$ and $L^2$ are each independently —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$, —OC(=O)NR$^a$—, —NR$^a$C(=O)O—, or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$ or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either: (a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In one embodiment, the LNP comprises a compound having a structure of Formula (III):

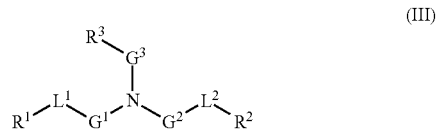

(III)

or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, OR$^5$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In one embodiment, the LNP comprises a compound having one of the following structures:
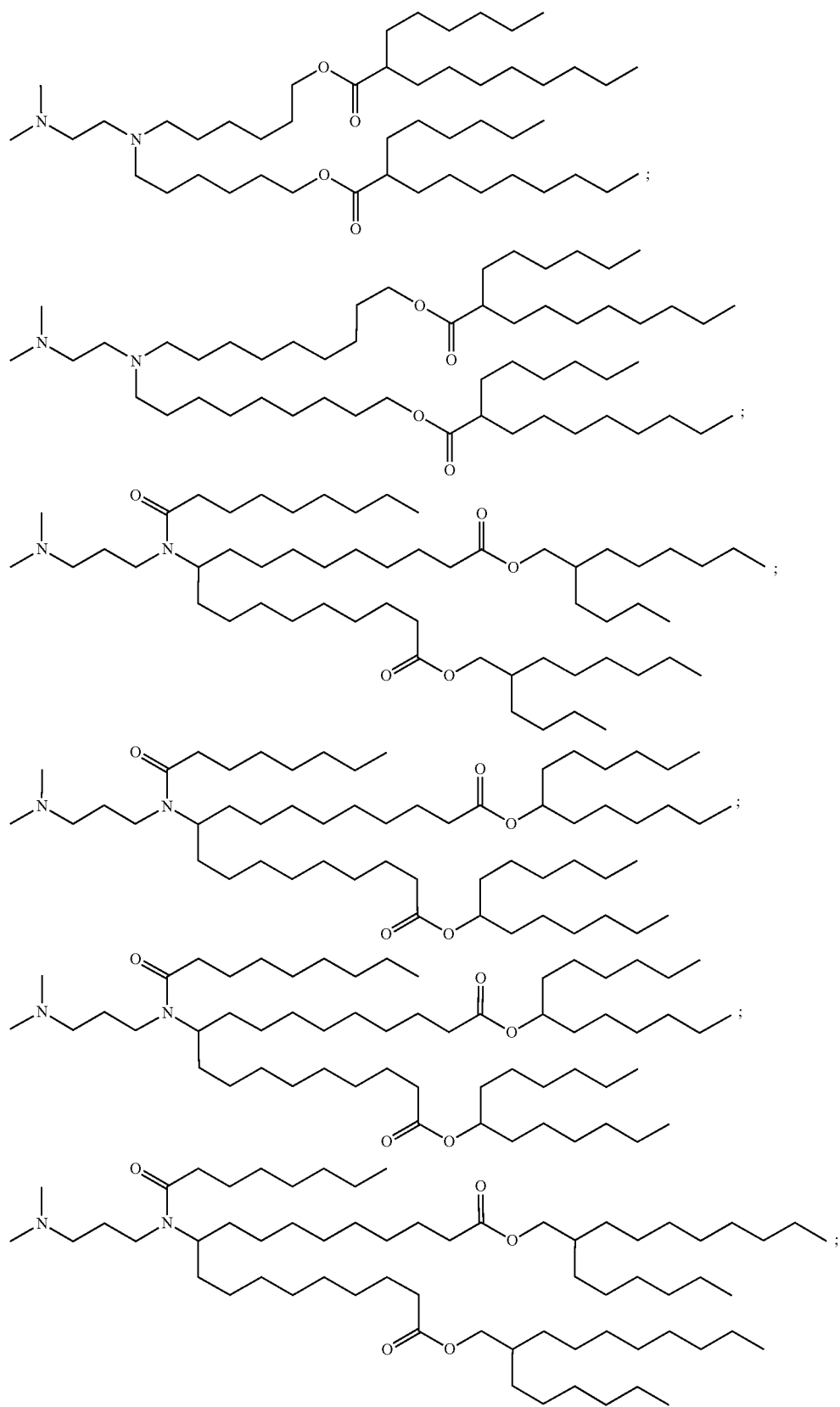

In one embodiment the LNP comprises a pegylated lipid having the following structure (IV):

(IV)

or a pharmaceutically acceptable salt, tautomer or stereoisomer thereof, wherein:

$R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60.

In one embodiment, the pegylated lipid has the following structure (IVa):

(IVa)

wherein n is an integer selected such that the average molecular weight of the pegylated lipid is about 2500 g/mol.

In one aspect, the present invention provides a method of inducing an adaptive immune response against Zika virus (ZIKV) in a subject. The method comprises administering to the subject an effective amount of a composition comprising at least one nucleoside-modified RNA encoding at least one ZIKV antigen.

In one embodiment, the composition is administered by a delivery route selected from the group consisting of intradermal, subcutaneous, inhalation, intranasal, and intramuscualar.

In one embodiment, the method comprises a single administration of the composition. In one embodiment, the method comprises more than one administration (i.e., at least two, at least three, at least four, at least five, at least six, at least seven, at least eight, at least nine, at least ten, or more) of the composition.

In one embodiment, the method treats or prevents an infection, disease, or disorder associated with ZIKV in the subject. In one embodiment, the method treats or prevents an infection, disease, or disorder associated with ZIKV in an unborn child of the subject.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A-FIG. 1D, C57BL/6 mice were immunized with 30 μg of nucleoside-modified ZIKV prM-E mRNA-LNPs (n=8) or control poly (C) RNA-LNPs (n=4). (FIG. 1A) At week 2, antigen-specific CD4+ T cells were detected by intracellular cytokine staining. The antibody response was monitored by (FIG. 1B) ELISA, (FIG. 1C) PRNT using ZIKV MR-766, and (FIG. 1D) RVP using ZIKV H/PF/2013. FIG. 1E-FIG. 1G, BALB/c mice were immunized similarly with ZIKV mRNA-LNPs (n=10) or poly(C) RNA-LNPs (n=5) and monitored by (FIG. 1E) ELISA, (FIG. 1F) PRNT using MR-766, and (FIG. 1G) RVP using H/PF/2013. Points represent individual mice; horizontal lines show the mean; dotted lines indicate the limit of detection. The controls in FIG. 1D and FIG. 1G is from the week 8 time point. * $P<0.05$ (unpaired t-test) in FIG. 1A; antibody responses in vaccine and control groups were compared at each time point by Mann-Whitney test, $P<0.01$ for all comparisons (FIG. 1B-FIG. 1G).

(FIG. 5A) The ZIKV mRNA encodes the signal peptide (SP) from MHC class II and prM and E glycoproteins from ZIKV H/PF/2013. (FIG. 5B) mRNA was transfected into 293T cells (n=3), human DC (n=2), or murine DC (n=2). E protein expression in cell lysate and supernatant was probed by Western blot, using luciferase mRNA-transfected cells as a negative control. (FIG. 5C) ZIKV mRNA supernatant from transfected 293T cells was characterized (n=3) by ultracentrifugation in the presence and absence of 0.5% Triton X-100, followed by Western blot of input (IN), pellet (P), and final supernatant (S) fractions.

Figures 1A, 1B, 1C, 1D:
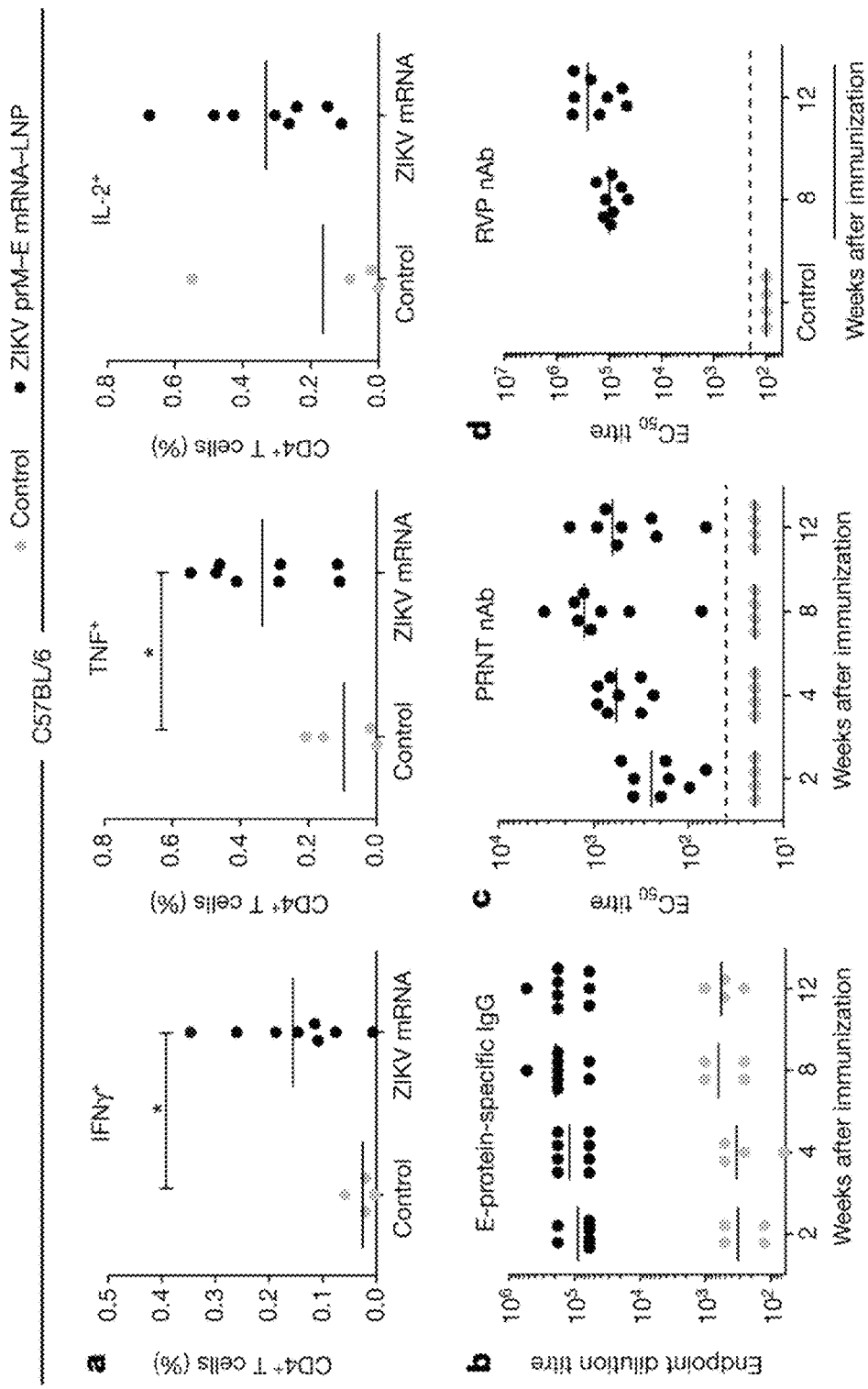
FIG. 1A through FIG. 1G depict the results of experiments demonstrating that nucleoside-modified ZIKV mRNA-LNP immunization elicits ZIKV-specific T helper and neutralizing antibody responses.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) RNA, and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Immunogen" refers to any substance introduced into the body in order to generate an immune response. That substance can a physical molecule, such as a protein, or can be encoded by a vector, such as DNA, mRNA, or a virus.

"Immune response," as the term is used herein, means a process involving the activation and/or induction of an effector function in, by way of non-limiting examples, a T cell, B cell, natural killer (NK) cell, and/or antigen-presenting cells (APC). Thus, an immune response, as would be understood by the skilled artisan, includes, but is not limited to, any detectable antigen-specific activation and/or induction of a helper T cell or cytotoxic T cell activity or response, production of antibodies, antigen presenting cell activity or infiltration, macrophage activity or infiltration, neutrophil activity or infiltration, and the like.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleosides (nucleobase bound to ribose or deoxyribose sugar via N-glycosidic linkage) are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In addition, the nucleotide sequence may contain modified nucleosides that are capable of being translation by translational machinery in a cell. For example, an mRNA where all of the uridines have been replaced with pseudouridine, 1-methyl psuedouridine, or another modified nucleoside.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA or RNA sequences are contiguous and, where necessary to join two protein coding regions, in the same reading frame.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

In certain instances, the polynucleotide or nucleic acid of the invention is a "nucleoside-modified nucleic acid," which refers to a nucleic acid comprising at least one modified nucleoside. A "modified nucleoside" refers to a nucleoside with a modification. For example, over one hundred different nucleoside modifications have been identified in RNA (Rozenski, et al., 1999, The RNA Modification Database: 1999 update. Nucl Acids Res 27: 196-197).

In certain embodiments, "pseudouridine" refers, in another embodiment, to $m^1acp^3\Psi$ (1-methyl-3-(3-amino-3-carboxypropyl) pseudouridine. In another embodiment, the term refers to $m^1\Psi$ (1-methylpseudouridine). In another embodiment, the term refers to $\Psi m$ (2'-O-methylpseudouridine). In another embodiment, the term refers to $m^5D$ (5-methyldihydrouridine). In another embodiment, the term refers to $m^3\Psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence. For example, the promoter that is recognized by bacteriophage RNA polymerase and is used to generate the mRNA by in vitro transcription.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more other species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, diminution, remission, or eradication of at least one sign or symptom of a disease or disorder.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for inducing an immune response against ZIKV in a subject. In certain embodiments, the present invention provides a composition comprising a nucleic acid molecule encoding a ZIKV antigen, where the ZIKV antigen induces an immune response against ZIKV in the subject. In some embodiments, the induced immune response is an adaptive immune response. For example, in certain embodiments, the composition comprises a vaccine comprising a nucleic acid molecule encoding a ZIKV antigen. In certain embodiments, the ZIKV antigen induces expression of a protective antibody. In certain embodiments, the ZIKV antigen provides an adjuvant function.

In one embodiment, the composition of the invention comprises in vitro transcribed (IVT) RNA. For example, in certain embodiments, the composition of the invention comprises IVT RNA which encodes a ZIKV antigen, where the ZIKV antigen induces an adaptive immune response. In certain embodiments, the ZIKV antigen is at least one of ZIKV envelope (E) protein, ZIKV pre-membrane (prM) protein, ZIKV membrane (M) protein, ZIKV capsid (C) protein, ZIKV NS1, ZIKV NS2A, ZIKV NS2B, ZIKV NS3, ZIKV NS4A, ZIKV NS4B, ZIKV NS5, or a fragment thereof.

In certain embodiments, the antigen-encoding nucleic acid of the present composition is a nucleoside-modified RNA. The present invention is based in part on the finding that nucleoside-modified RNA encoding a ZIKV antigen induces a robust and durable immune response against ZIKV. Further, the ZIKV antigen-encoding nucleoside-modified RNA was observed to induce antigen-specific antibody production. The nucleoside-modified RNA is demonstrated to induce adaptive immune responses that are comparable or superior to current ZIKV vaccine strategies.

In certain embodiments, the antigen-encoding nucleic acid of the present composition is a purified nucleoside-modified RNA. For example, in certain embodiments, the composition is purified such that is free of double-stranded contaminants.

In certain embodiments, the composition comprises a lipid nanoparticle (LNP). For example, in one embodiment, the composition comprises a ZIKV antigen-encoding nucleic acid molecule encapsulated within a LNP. In certain instances, the LNP enhances cellular uptake of the nucleic acid molecule.

In certain embodiments, the composition comprises an adjuvant. In certain embodiments, the composition comprises a nucleic acid molecule encoding an adjuvant. For example, in one embodiment, the composition comprises a nucleoside-modified RNA encoding an adjuvant. In one embodiment, the composition comprises a nucleoside-modified RNA encoding a ZIKV antigen and an adjuvant. In one embodiment, the composition comprises a first nucleoside-modified RNA, which encodes a ZIKV antigen, and a second nucleoside-modified RNA, which encodes an adjuvant. In one embodiment, the composition comprises a nucleoside-modified RNA encoding an adjuvant and a LNP, wherein the LNP has adjuvant activity.

In one embodiment, the present invention provides a method for inducing an immune response against ZIKV in a subject. In some embodiments, the method comprises administering to the subject a composition comprising one or more nucleoside-modified RNA encoding a ZIKV antigen, adjuvant, or a combination thereof.

In one embodiment, the method comprises the systemic administration of the composition into the subject, including for example intradermal administration or intradermal administration. In certain embodiments, the method comprises administering a plurality of doses to the subject. In another embodiment, the method comprises administering a single dose of the composition, where the single dose is effective in inducing an adaptive immune response. In one embodiment, the method provides a sustained or prolonged immune response.

Vaccine

In one embodiment, the present invention provides an immunogenic composition for inducing an immune response against ZIKV in a subject. For example, in one embodiment, the immunogenic composition is a vaccine. For a composition to be useful as a vaccine, the composition must induce an immune response to the ZIKV antigen in a cell, tissue or mammal (e.g., a human). In certain instances, the vaccine induces a protective immune response in the mammal. As used herein, an "immunogenic composition" may comprise an antigen (e.g., a peptide or polypeptide), a nucleic acid encoding an antigen, a cell expressing or presenting an antigen or cellular component, or a combination thereof. In particular embodiments, the composition comprises or encodes all or part of any peptide antigen described herein, or an immunogenically functional equivalent thereof. In other embodiments, the composition is in a mixture that comprises an additional immunostimulatory agent or nucleic acids encoding such an agent. Immunostimulatory agents include but are not limited to an additional antigen, an immunomodulator, an antigen presenting cell, lipid nanoparticle, or an adjuvant. In other embodiments, one or more of the additional agent(s) is covalently bonded to the antigen or an immunostimulatory agent, in any combination.

In the context of the present invention, the term "vaccine" refers to a composition that induces an immune response upon inoculation into animals. In some embodiments, the induced immune response provides protective immunity.

A vaccine of the present invention may vary in its composition of nucleic acid and/or cellular components. In a non-limiting example, a nucleic acid encoding a ZIKV antigen might also be formulated with an adjuvant. Of course, it will be understood that various compositions described herein may further comprise additional components. For example, one or more vaccine components may be comprised in a lipid, liposome, or lipid nanoparticle. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

The induction of the immunity by the expression of the ZIKV antigen can be detected by observing in vivo or in vitro the response of all or any part of the immune system in the host against the ZIKV antigen.

For example, a method for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen.

These antigen-stimulated cells then proliferate. This process is referred to herein as "activation" of T cells. Therefore, CTL induction by an epitope of a polypeptide or peptide or combinations thereof can be evaluated by presenting an epitope of a polypeptide or peptide or combinations thereof to a T cell by APC, and detecting the induction of CTL. Furthermore, APCs have the effect of activating B cells, CD4+ T cells, CD8+ T cells, macrophages, eosinophils and NK cells.

A method for evaluating the inducing action of CTL using dendritic cells (DCs) as APC is well known in the art. DC is a representative APC having a robust CTL inducing action among APCs. In the methods of the invention, the epitope of a polypeptide or peptide or combinations thereof is initially expressed by the DC and then this DC is contacted with T cells. Detection of T cells having cytotoxic effects against the cells of interest after the contact with DC shows that the epitope of a polypeptide or peptide or combinations thereof has an activity of inducing the cytotoxic T cells. Furthermore, the induced immune response can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The antigens confirmed to possess CTL-inducing activity by these methods are antigens having DC activation effect and subsequent CTL-inducing activity. Furthermore, CTLs that have acquired cytotoxicity due to presentation of the antigen by APC can be also used as vaccines against antigen-associated disorders.

The induction of immunity by expression of the ZIKV antigen can be further confirmed by observing the induction of antibody production against the ZIKV antigen. For example, when antibodies against an antigen are induced in a laboratory animal immunized with the composition encoding the antigen, and when antigen-associated pathology is suppressed by those antibodies, the composition is determined to induce immunity.

The induction of immunity by expression of the ZIKV antigen can be further confirmed by observing the induction of CD4+ T cells. CD4+ T cells can also lyse target cells, but mainly supply help in the induction of other types of immune responses, including CTL and antibody generation. The type of CD4+ T cell help can be characterized, as Th1, Th2, Th9, Th17, T regulatory, or T follicular helper ($T_{fh}$) cells. Each subtype of CD4+ T cell supplies help to certain types of immune responses. In one embodiment, the composition selectively induces T follicular helper cells, which drive potent antibody responses.

The therapeutic compounds or compositions of the invention may be administered prophylactically (i.e., to prevent a disease or disorder) or therapeutically (i.e., to treat a disease or disorder) to subjects suffering from, or at risk of (or susceptible to) developing the disease or disorder. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity, which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Antigen

The present invention provides a composition that induces an immune response in a subject. In one embodiment, the composition comprises a ZIKV antigen. In one embodiment, the composition comprises a nucleic acid sequence, which encodes a ZIKV antigen. For example, in certain embodiments, the composition comprises a nucleoside-modified RNA encoding a ZIKV antigen. In certain embodiments, the composition comprises a purified, nucleoside-modified RNA encoding a ZIKV antigen. The antigen may include, but is not limited to a polypeptide, peptide or protein that induces an immune response in a subject.

In one embodiment, the antigen comprises a polypeptide or peptide associated with ZIKV, such that the antigen induces an immune response against the antigen, and therefore ZIKV. In one embodiment, the antigen comprises a fragment of a polypeptide or peptide associated with ZIKV, such that the antigen induces an immune response against ZIKV.

In certain embodiments, the ZIKV antigen is at least one of ZIKV envelope (E) protein, ZIKV pre-membrane (prM) protein, ZIKV membrane (M) protein, ZIKV capsid (C) protein, ZIKV NS1, ZIKV NS2A, ZIKV NS2B, ZIKV NS3, ZIKV NS4A, ZIKV NS4B, ZIKV NS5, or a fragment thereof.

In one embodiment, the antigen comprises a protein comprising a signal peptide (SP) from MHC class II. In one embodiment, the antigen comprises SP from MHC class II, prM of ZKIV, and E of ZIKV.

In one embodiment, the composition comprises a nucleic acid sequence encoding SP-prM-E, wherein the nucleic acid sequence comprises:

ATGGCCATAAGTGGAGTCCCGGTGCTAGGAT-TCTTCATCATAGC CGTGCTGATGAGCGCGCAG-GAATCATGGGCCGCCGAGGTGACGA-GACGGGG
GAGCGCATACTA-CATGTACTTGGACAGAAACGACGCCGGG-GAGGCCATATCC TTCCCAACCACATTGGGGAT-GAACAAGTGTTACATACAGATCATGGACCTGG
GACACATGTGCGACGCCACCATGAGC-TACGAATGCCCTATGCTGGACGAGGG GGTG-GAACCA-
GACGACGTCGACTGCTGGTGCAACACGACGTC AACTTGGGTG GTGTACGGAACCTGCCAC-CACAAAAAGGCGAAGCACGGAGATCGA-
GACGG GCCGTGACGCTCCCTCCCACTC-CACGAGGAAGCTGCAAACGCGGTCGCAAA
CCTGGTTGGAATCAAGAGAATA-CACAAAGCACTTGATCAGAGTCGAAAACTG
GATATTCAGGAACCCTGGCTTCGCGT-TAGCAGCAGCCGCCATCGCTTGGCTGT TGG-GAAGCTCAACGAGCCAAAAAGT-
CATATACTTGGTCATGATACTGCTGAT

CGCCCCGGCATACAGCATCAGGTGCATAGGAGTCAGCAACAGGGACTTCGTG GAAGGGATGTCAGGCGGGACCTGGGTGGACGTGGTCTTGGAACACGGAGGG TGCGTCACCGTAATGGCACAGGACAAACCGACGGTCG ACATAGAGCTGGTTA CAACAACAGTCAGCAACATGGCGGAGGTAAGATCCTACTGCTACGAGGCATC AATATCGGACATGGCGTCGGACAGCCGCTGCCCAACACAAGGCGAAGCCTAC CTGGACAAGCAATCAGACACGCAATACGTCTGCAAAAGAACGTTAGTGGACA GAGGCTGGGGAAACGGATGCGGACTGTTCGGCAAAGGGAGCCTGGTGACAT GCGCCAAGTTCGCATGCTCAAGAAAATGACCGGGAAGAGCATCCAGCCAG AGAACCTGGAGTACCGGATAATGCTGTCAGTGCACGGCTCCCAGCACAGCGG GATGATCGTGAACGACACAGGACACGAAACGGACGAGAAC AGAGCGAAGGT GGAGATAACGCCCAACTCACCAAGAGCCGAAGCCACCCTGGGGGGCTTCGG AAGCCTAGGACTGGACTGCGAACCGAGGACAGGCCTCGACTTCTCAGACTTG TACTACTTGACGATGAACAACAAGCACTGGTTGGTGCACAAGGAGTGGTTCC ACGACATCCATTACCTTGGCACGCCGGGGCAGACACCGGAACGCCACACTG GAACAACAAAGAAGCACTGGTAGAGTTCAAGGACGCACACGCCAAAAGGCA AACGGTCGTGGTCCTAGGGAGCCAAGAAGGGAGCAGTGCACACGGCCCTGGC CGGAGCGCTGGAGGCCGAGATGGACGGGGCAAAGGGAAGGCTGTCCTCCGG CCACTTGAAATGCCGCCTGAAAATGGACAAACTGAGATTGAAGGGCGTGTCA TACTCCTTGTGCACCGCAGCGTTCACATTCACCAAGATCCCGGCGGAAACAC TGCACGGGACAGTCACAGTGGAGGTACAGTACGCAGGGACAGACGGACCGT GCAAGGTGCCAGCGCAGATGGCGGTGGACATGCAAACCCTGACCCCAGTCG GGAGGTTGATAACCGCGAACCCCGTAATCACGGAAAGCACCGAGAACTCGA AGATGATGCTGGAACTCGATCCACCATTCGGGGACTCGTACATCGTCATAGG AGTCGGGGAGAAGAAGATCACCCACCACTGGCACAGGAGCGGCAGCACCAT CGGAAAAGCATTCGAAGCCACGGTGAGAGGGGCCAAGAGAATGGCAGTCTT GGGAGACACAGCCTGGGACTTCGGATCAGTCGGAGGCGCGCTCAACTCATTG GGCAAGGGCATCCACCAAATCTTCGGAGCAGCTTTCAAATCATTGTTCGGAG GAATGTCCTGGTTCTCACAAATCCTCATCGGAACGTTGCTGATGTGGTTGGGG CTGAACACAAAGAACGGATCGATCTCCCTGATGTGCTTGGCCTTAGGGGGAG TGTTGATCTTCTTATCCACAGCGGTCTCCGCGTAA (SEQ ID NO: 1). In one embodiment, the composition comprises nucleoside-modified SEQ ID NO: 1, wherein one or more residues are replaced with a modified nucleoside as described elsewhere herein.

In one embodiment, the composition comprises a nucleic acid sequence encoding SP-prM-E having an amino acid sequence comprising:

(SEQ ID NO: 2)
MAISGVPVLGFFIIAVLMSAQESWAAEVTRRGSAYYMYLDRNDA

GEAISFPTTLGMNKCYIQIMDLGHMCDATMSYECPMLDEGVEPDDVDCW

CNTTSTWVVYGTCHHKKGEARRSRRAVTLPSHSTRKLQTRSQTWLESRE

YTKHLIRVENWIFRNPGFALAAAAIAWLLGSSTSQKVIYLVMILLIAPA

YSIRCIGVSNRDFVEGMSGGTWVDVVLEHGGCVTVMAQDKPTVDIELVT

TTVSNMAEVRSYCYEASISDMASDSRCPTQGEAYLDKQSDTQYVCKRTL

VDRGWGNGCGLFGKGSLVTCAKFACSKKMTGKSIQPENLEYRIMLSVHG

SQHSGMIVNDTGHETDENRAKVEITPNSPRAEATLGGFGSLGLDCEPRT

GLDFSDLYYLTMNNKHWLVHKEWFHDIPLPWHAGADTGTPHWNNKEALV

EFKDAHAKRQTVVVLGSQEGAVHTALAGALEAEMDGAKGRLSSGHLKCR

LKMDKLRLKGVSYSLCTAAFTFTKIPAETLHGTVTVEVQYAGTDGPCKV

PAQMAVDMQTLTPVGRLITANPVITESTENSKMMLELDPPFGDSYIVIG

VGEKKITHEIWHRSGSTIGKAFEATVRGAKRMAVLGDTAWDFGSVGGAL

NSLGKGIHQIFGAAFKSLFGGMSWFSQILIGTLLMWLGLNTKNGSISLM

CLALGGVLIFLSTAVSA

The ZIKV antigen may be of any type or strain of ZIKV. For example, in one embodiment, the ZIKV antigen is a protein, or fragment thereof, of a ZIKV strain including, but not limited to, H/PF/2013 (GenBank: KJ776791), PRV-ABC59, MEX I-44, VEN/UF-2/2016, SZ01/2016/China, SEN/1984/41671-DAK, KHM/2010/FSS13025, SEN/1984/41662-DAK, SEN/1984/41525-DAK, PHL/2012/CPC-0740, THA/2014/SV0127-14, COL/UF-1/2016, CN/SZ02/2016, GZ02/2016, HND/2016/HU-ME167-PLA, USA/2016/FL-038-URI, USA/2016/FL-030-URI, USA/2016/FL-01-MOS, USA/2016/FL-02-MOS, USA/2016/FL-03-MOS, and DOM/2016/BB-0115-SER.

In certain embodiments, the ZIKV antigen comprises an amino acid sequence that is substantially homologous to the amino acid sequence of a ZIKV antigen described herein and retains the immunogenic function of the original amino acid sequence. For example, in certain embodiments, the amino acid sequence of the ZIKV antigen has a degree of identity with respect to the original amino acid sequence of at least 60%, of at least 65%, of at least 70%, of at least 75%, of at least 80%, of at least 85%, of at least 90%, of at least 91%, of at least 92%, of at least 93%, of at least 94%, of at least 95%, of at least 96%, of at least 97%, of at least 98%, of at least 99%, or of at least 99.5%

In one embodiment, the ZIKV antigen is encoded by a nucleic acid sequence of a nucleic acid molecule. In certain embodiments, the nucleic acid sequence comprises DNA, RNA, cDNA, a variant thereof, a fragment thereof, or a combination thereof. In one embodiment, the nucleic acid sequence comprises a modified nucleic acid sequence. For example, in one embodiment the ZIKV antigen-encoding nucleic acid sequence comprises nucleoside-modified RNA, as described in detail elsewhere herein. In certain instances, the nucleic acid sequence comprises include additional sequences that encode linker or tag sequences that are linked to the antigen by a peptide bond.

Adjuvant

In one embodiment, the composition comprises an adjuvant. In one embodiment, the composition comprises a nucleic acid molecule encoding an adjuvant. In one embodiment, the adjuvant-encoding nucleic acid molecule is IVT RNA. In one embodiment, the adjuvant-encoding nucleic acid molecule is nucleoside-modified RNA.

Exemplary adjuvants include, but are not limited to, alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86. Other genes which may be useful adjuvants include those encoding: MCP-I, MIP-Ia, MIP-Ip, IL-8, RANTES, L-selectin, P-selectin, E-selectin, CD34, GlyCAM-1, MadCAM-1, LFA-I, VLA-I, Mac-1, pl50.95, PECAM, ICAM-I, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-I, DR3, TRAMP, Apo-3, AIR, LARD, NGRF, DR4, DR5, KILLER, TRAIL-R2, TRICK2, DR6, Caspase ICE, Fos, c-jun, Sp-I, Ap-I, Ap-2, p38, p65Rel, MyD88, IRAK, TRAF6, IkB, Inactive NIK, SAP K, SAP-I, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, TAP2, anti-CTLA4-sc, anti-LAG3-Ig, anti-TIM3-Ig, and functional fragments thereof.

In certain embodiments, the composition comprises a lipid nanoparticle, where the lipid nanoparticle acts as an adjuvant.

Nucleic Acids

In one embodiment, the invention includes a nucleoside-modified nucleic acid molecule. In one embodiment, the nucleoside-modified nucleic acid molecule encodes a ZIKV antigen. In one embodiment, the nucleoside-modified nucleic acid molecule encodes a plurality of antigens, including one or more ZIKV antigens. In certain embodiments, the nucleoside-modified nucleic acid molecule encodes a ZIKV antigen that induces an adaptive immune response against the ZIKV antigen. In one embodiment, the invention includes a nucleoside-modified nucleic acid molecule encoding an adjuvant.

The nucleotide sequences encoding a ZIKV antigen or adjuvant, as described herein, can alternatively comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences recited herein and encode a ZIKV antigen or adjuvant of interest.

As used herein, a nucleotide sequence is "substantially homologous" to any of the nucleotide sequences described herein when its nucleotide sequence has a degree of identity with respect to the nucleotide sequence of at least 60%, of at least 65%, of at least 70%, of at least 65%, of at least 80%, of at least 85%, of at least 90%, of at least 95%, of at least 96%, of at least 97%, of at least 98%, or of at least 99%. A nucleotide sequence that is substantially homologous to a nucleotide sequence encoding an antigen can typically be isolated from a producer organism of the antigen based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art.

Further, the scope of the invention includes nucleotide sequences that encode amino acid sequences that are substantially homologous to the amino acid sequences recited herein and preserve the immunogenic function of the original amino acid sequence.

As used herein, an amino acid sequence is "substantially homologous" to any of the amino acid sequences described herein when its amino acid sequence has a degree of identity with respect to the amino acid sequence of at least 60%, of at least 65%, of at least 70%, of at least 65%, of at least 80%, of at least 85%, of at least 90%, of at least 95%, of at least 96%, of at least 97%, of at least 98%, or of at least 99%. The identity between two amino acid sequences can be determined by using the BLASTN algorithm (BLAST Manual, Altschul, S., et al., NCBI NLM NIH Bethesda, Md. 20894, Altschul, S., et al., J. Mol. Biol. 215: 403-410 (1990)).

In one embodiment, the invention relates to a construct, comprising a nucleotide sequence encoding a ZIKV antigen. In one embodiment, the construct comprises a plurality of nucleotide sequences encoding a plurality of ZIKV antigens. For example, in certain embodiments, the construct encodes 1 or more, 2 or more, 5 or more, or all 10 ZIKV antigens. In one embodiment, the invention relates to a construct, comprising a nucleotide sequence encoding an adjuvant. In one embodiment, the construct comprises a first nucleotide sequence encoding a ZIKV antigen and a second nucleotide sequence encoding an adjuvant.

In one embodiment, the composition comprises a plurality of constructs, each construct encoding one or more ZIKV antigens. In certain embodiments, the composition comprises 1 or more, 2 or more, 3 or more, 4 or more, 5 or more, 6 or more, 7 or more, 8 or more, 9 or more, 10 or more, 15 or more, or 20 or more constructs. In one embodiment, the composition comprises a first construct, comprising a nucleotide sequence encoding a ZIKV antigen; and a second construct, comprising a nucleotide sequence encoding an adjuvant.

In another particular embodiment, the construct is operatively bound to a translational control element. The construct can incorporate an operatively bound regulatory sequence for the expression of the nucleotide sequence of the invention, thus forming an expression cassette.

Vectors

The nucleic acid sequences coding for the ZIKV antigen or adjuvant can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The nucleic acid can be cloned into a number of types of vectors. For example, the nucleic acid can be cloned into a vector including, but not limited to a plasmid, a phagemid, a phage derivative, an animal virus, a PCR-generated linear DNA sequence, and a cosmid. Vectors of particular interest include expression vectors, replication vectors, probe generation vectors, sequencing vectors and vectors optimized for in vitro transcription.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, carbohydrates, peptides, cationic polymers, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/RNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the mRNA sequence in the host cell, a variety of assays may be performed. Such assays include, for example, "molecular biological" assays well known to those of skill in the art, such as Northern blotting and RT-PCR; "biochemical" assays, such as detecting the presence or absence of a particular peptide, e.g., by immunogenic means (ELISAs and Western blots) or by assays described herein to identify agents falling within the scope of the invention.

In Vitro Transcribed RNA

In one embodiment, the composition of the invention comprises in vitro transcribed (IVT) RNA encoding a ZIKV antigen. In one embodiment, the composition of the invention comprises IVT RNA encoding a plurality of ZIKV antigens. In one embodiment, the composition of the invention comprises IVT RNA encoding an adjuvant. In one embodiment, the composition of the invention comprises IVT RNA encoding one or more ZIKV antigens and one or more adjuvants.

In one embodiment, an IVT RNA can be introduced to a cell as a form of transient transfection. The RNA is produced by in vitro transcription using a plasmid DNA template generated synthetically. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. In one embodiment, the desired template for in vitro transcription is a ZIKV antigen capable of inducing an adaptive immune response. In one embodiment, the desired template for in vitro transcription is an adjuvant capable of enhancing an adaptive immune response.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. In another embodiment, the DNA to be used for PCR is a gene from a pathogenic or commensal organism, including bacteria, viruses, parasites, and fungi. In another embodiment, the DNA to be used for PCR is from a pathogenic or commensal organism, including bacteria, viruses, parasites, and fungi, including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that induce or enhance an adaptive immune response in an organism. In certain instances, the genes are useful for a short term treatment. In certain instances, the genes have limited safety concerns regarding dosage of the expressed gene.

In various embodiments, a plasmid is used to generate a template for in vitro transcription of mRNA, which is used for transfection.

Chemical structures with the ability to promote stability and/or translation efficiency may also be used. In certain embodiments, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 RNA polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product, which is not suitable for expression in eukaryotic cells. The transcription of plasmid DNA linearized at the end of the 3' UTR results in normal sized mRNA, which is effective in eukaryotic transfection when it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However, polyA/T sequence integrated into plasmid DNA can cause plasmid instability, which can be ameliorated through the use of recombination incompetent bacterial cells for plasmid propagation.

Poly(A) tails of RNAs can be further extended following in vitro transcription with the use of a poly(A) polymerase, such as E. coli polyA polymerase (E-PAP) or yeast polyA polymerase. In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to mRNA molecules. In one embodiment, RNAs produced by the methods to include a 5' cap1 structure. Such cap1 structure can be generated using Vaccinia capping enzyme and 2'-O-methyltransferase enzymes (CellScript, Madison, WI). Alternatively, 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001). In certain embodiments RNA of the invention is introduced to a cell with a method comprising the use of TransIT®-mRNA transfection Kit (Mirus, Madison WI), which, in some instances, provides high efficiency, low toxicity, transfection.

Nucleoside-Modified RNA

In one embodiment, the composition of the present invention comprises a nucleoside-modified nucleic acid encoding a ZIKV antigen as described herein. In one embodiment, the composition of the present invention comprises a nucleoside-modified nucleic acid encoding a plurality of antigens, including one or more ZIKV antigens. In one embodiment, the composition of the present invention comprises a nucleoside-modified nucleic acid encoding an adjuvant as described herein. In one embodiment, the composition of the present invention comprises a nucleoside-modified nucleic acid encoding one or more ZIKV antigens and one or more adjuvants.

For example, in one embodiment, the composition comprises a nucleoside-modified RNA. In one embodiment, the composition comprises a nucleoside-modified mRNA. Nucleoside-modified mRNA have particular advantages over non-modified mRNA, including for example, increased stability, low or absent innate immunogenicity, and enhanced translation. Nucleoside-modified mRNA useful in the present invention is further described in U.S. Pat. Nos. 8,278,036, 8,691,966, and 8,835,108, each of which is incorporated by reference herein in its entirety.

In certain embodiments, nucleoside-modified mRNA does not activate any pathophysiologic pathways, translates very efficiently and almost immediately following delivery, and serve as templates for continuous protein production in vivo lasting for several days (Karikó et al., 2008, Mol Ther 16:1833-1840; Karikó et al., 2012, Mol Ther 20:948-953). The amount of mRNA required to exert a physiological effect is small and that makes it applicable for human therapy. For example, as described herein, nucleoside-modified mRNA encoding a ZIKV antigen has demonstrated the ability to antigen-specific antibody production. For example, in certain instances, antigen encoded by nucleoside-modified mRNA induces greater production of antigen-specific antibody production as compared to antigen encoded by non-modified mRNA.

In certain instances, expressing a protein by delivering the encoding mRNA has many benefits over methods that use protein, plasmid DNA or viral vectors. During mRNA transfection, the coding sequence of the desired protein is the only substance delivered to cells, thus avoiding all the side effects associated with plasmid backbones, viral genes, and viral proteins. More importantly, unlike DNA- and viral-based vectors, the mRNA does not carry the risk of being incorporated into the genome and protein production starts immediately after mRNA delivery. For example, high levels of circulating proteins have been measured within 15 to 30 minutes of in vivo injection of the encoding mRNA. In certain embodiments, using mRNA rather than the protein also has many advantages. Half-lives of proteins in the circulation are often short, thus protein treatment would need frequent dosing, while mRNA provides a template for continuous protein production for several days. Purification of proteins is problematic and they can contain aggregates and other impurities that cause adverse effects (Kromminga and Schellekens, 2005, Ann NY Acad Sci 1050:257-265).

In certain embodiments, the nucleoside-modified RNA comprises the naturally occurring modified-nucleoside pseudouridine. In certain embodiments, inclusion of pseudouridine makes the mRNA more stable, non-immunogenic, and highly translatable (Karikó et al., 2008, Mol Ther 16:1833-1840; Anderson et al., 2010, Nucleic Acids Res 38:5884-5892; Anderson et al., 2011, Nucleic Acids Research 39:9329-9338; Karikó et al., 2011, Nucleic Acids Research 39:e142; Karikó et al., 2012, Mol Ther 20:948-953; Karikó et al., 2005, Immunity 23:165-175).

It has been demonstrated that the presence of modified nucleosides, including pseudouridines in RNA suppress their innate immunogenicity (Karikó et al., 2005, Immunity 23:165-175). Further, protein-encoding, in vitro-transcribed RNA containing pseudouridine can be translated more efficiently than RNA containing no or other modified nucleosides (Karikó et al., 2008, Mol Ther 16:1833-1840). Subsequently, it is shown that the presence of pseudouridine improves the stability of RNA (Anderson et al., 2011, Nucleic Acids Research 39:9329-9338) and abates both activation of PKR and inhibition of translation (Anderson et al., 2010, Nucleic Acids Res 38:5884-5892).

In certain embodiments, the nucleoside-modified nucleic acid molecule is a purified nucleoside-modified nucleic acid molecule. For example, in certain embodiments, the composition is purified to remove double-stranded contaminants. In certain instances, a preparative high performance liquid chromatography (HPLC) purification procedure is used to obtain pseudouridine-containing RNA that has superior translational potential and no innate immunogenicity (Karikó et al., 2011, Nucleic Acids Research 39:e142). Administering HPLC-purified, pseudourine-containing RNA coding for erythropoietin into mice and macaques resulted in a significant increase of serum EPO levels (Karikó et al., 2012, Mol Ther 20:948-953), thus confirming that pseudouridine-containing mRNA is suitable for in vivo protein therapy. In certain embodiments, the nucleoside-modified nucleic acid molecule is purified using non-HPLC methods. In certain instances, the nucleoside-modified nucleic acid molecule is purified using chromatography methods, including but not limited to HPLC and fast protein liquid chromatography (FPLC). An exemplary FPLC-based purification procedure is described in Weissman et al., 2013, Methods Mol Biol, 969: 43-54. Exemplary purification procedures are also described in U.S. Patent Application Publication No. US2016/0032316, which is hereby incorporated by reference in its entirety.

The present invention encompasses RNA, oligoribonucleotide, and polyribonucleotide molecules comprising pseudouridine or a modified nucleoside. In certain embodiments, the composition comprises an isolated nucleic acid encoding an antigen, wherein the nucleic acid comprises a pseudouridine or a modified nucleoside. In certain embodiments, the composition comprises a vector, comprising an isolated nucleic acid encoding an antigen, adjuvant, or combination thereof, wherein the nucleic acid comprises a pseudouridine or a modified nucleoside.

In one embodiment, the nucleoside-modified RNA of the invention is IVT RNA, as described elsewhere herein. For example, in certain embodiments, the nucleoside-modified RNA is synthesized by T7 phage RNA polymerase. In another embodiment, the nucleoside-modified mRNA is synthesized by SP6 phage RNA polymerase. In another embodiment, the nucleoside-modified RNA is synthesized by T3 phage RNA polymerase.

In one embodiment, the modified nucleoside is $m^1acp^3\Psi$ (1-methyl-3-(3-amino-3-carboxypropyl) pseudouridine. In another embodiment, the modified nucleoside is $m^1\Psi$ (1-methylpseudouridine). In another embodiment, the modified nucleoside is $\Psi m$ (2'-O-methylpseudouridine). In another embodiment, the modified nucleoside is $m^5D$ (5-methyldihydrouridine). In another embodiment, the modified nucleoside is $m^3\Psi$ (3-methylpseudouridine). In another embodiment, the modified nucleoside is a pseudouridine moiety that is not further modified. In another embodiment, the modified nucleoside is a monophosphate, diphosphate, or triphosphate of any of the above pseudouridines. In another embodiment, the modified nucleoside is any other pseudouridine-like nucleoside known in the art.

In another embodiment, the nucleoside that is modified in the nucleoside-modified RNA the present invention is uridine (U). In another embodiment, the modified nucleoside is cytidine (C). In another embodiment, the modified nucleoside is adenosine (A). In another embodiment, the modified nucleoside is guanosine (G).

In another embodiment, the modified nucleoside of the present invention is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is $\Psi$ (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$- glycinylcarbamoyladenosine); t⁶A (N⁶-threonylcarbamoyladenosine); ms²t⁶A (2-methylthio-N⁶-threonyl carbamoyladenosine); m⁶t⁶A (N⁶-methyl-N⁶-threonylcarbamoyladenosine); hn⁶A(N⁶-hydroxynorvalylcarbamoyladenosine); ms²hn⁶A (2-methylthio-N⁶-hydroxynorvalyl carbamoyladenosine); Ar(p) (2'-O-ribosyladenosine (phosphate)); I (inosine); m¹I (1-methylinosine); m¹Im (1,2'-O-dimethylinosine); m³C (3-methylcytidine); Cm (2'-O-methylcytidine); s²C (2-thiocytidine); ac⁴C (N⁴-acetylcytidine); f⁵C (5-formylcytidine); m⁵Cm (5,2'-O-dimethylcytidine); ac⁴Cm (N⁴-acetyl-2'-O-methylcytidine); k²C (lysidine); m¹G (1-methylguanosine); m²G (N²-methylguanosine); m⁷G (7-methylguanosine); Gm (2'-O-methylguanosine); m²₂G (N²,N²-dimethylguanosine); m²Gm (N²,2'-O-dimethylguanosine); m²₂Gm (N²,N²,2'-O-trimethylguanosine); Gr(p) (2'-O-ribosylguanosine (phosphate)); yW (wybutosine); o₂yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQ₀ (7-cyano-7-deazaguanosine); preQi (7-aminomethyl-7-deazaguanosine); G⁺ (archaeosine); D (dihydrouridine); m⁵Um (5,2'-O-dimethyluridine); s⁴U (4-thiouridine); m⁵s²U (5-methyl-2-thiouridine); s²Um (2-thio-2'-O-methyluridine); acp³U (3-(3-amino-3-carboxypropyl)uridine); ho⁵U (5-hydroxyuridine); mo⁵U (5-methoxyuridine); cmo⁵U (uridine 5-oxyacetic acid); mcmo⁵U (uridine 5-oxyacetic acid methyl ester); chm⁵U (5-(carboxyhydroxymethyl)uridine)); mchm⁵U (5-(carboxyhydroxymethyl)uridine methyl ester); mcm⁵U (5-methoxycarbonylmethyluridine); mcm²Um (5-methoxycarbonylmethyl-2'-O-methyluridine); mcm²s²U (5-methoxycarbonylmethyl-2-thiouridine); nm⁵s²U (5-aminomethyl-2-thiouridine); mnm⁵U (5-methylaminomethyluridine); mnm⁵s²U (5-methylaminomethyl-2-thiouridine); mnm⁵se²U (5-methylaminomethyl-2-selenouridine); nCm⁵U (5-carbamoylmethyluridine); nCm⁵Um (5-carbamoylmethyl-2'-O-methyluridine); cmnm⁵U (5-carboxymethylaminomethyluridine); cmnm⁵Um (5-carboxymethylaminomethyl-2'-O-methyluridine); cmnm⁵s²U (5-carboxymethylaminomethyl-2-thiouridine); m⁶²A (N⁶,N⁶-dimethyladenosine); Im (2'-O-methylinosine); m⁴C (N⁴-methylcytidine); m⁴Cm (N⁴,2'-O-dimethylcytidine); hm⁵C (5-hydroxymethylcytidine); m³U (3-methyluridine); cm⁵U (5-carboxymethyluridine); m⁶Am (N⁶,2'-O-dimethyladenosine); m⁶²Am (N⁶,N⁶,O-2'-trimethyladenosine); m²,7G (N²,7-dimethylguanosine); m²,²,⁷G (N²,N²,⁷-trimethylguanosine); m³Um (3,2'-O-dimethyluridine); m⁵D (5-methyldihydrouridine); f⁵Cm (5-formyl-2'-O-methylcytidine); m¹Gm (1,2'-O-dimethylguanosine); m¹Am (1,2'-O-dimethyladenosine); τm⁵U (5-taurinomethyluridine); τm⁵s²U (5-taurinomethyl-2-thiouridine)); imG-14 (4-demethylwyosine); imG2 (isowyosine); or ac⁶A (N⁶-acetyladenosine).

In another embodiment, a nucleoside-modified RNA of the present invention comprises a combination of 2 or more of the above modifications. In another embodiment, the nucleoside-modified RNA comprises a combination of 3 or more of the above modifications. In another embodiment, the nucleoside-modified RNA comprises a combination of more than 3 of the above modifications.

In various embodiments, between 0.1% and 100% of the residues in the nucleoside-modified of the present invention are modified (e.g., either by the presence of pseudouridine or another modified nucleoside base). In one embodiment, the fraction of modified residues is 0.1%. In another embodiment, the fraction of modified residues is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.7%. In another embodiment, the fraction is 0.8%. In another embodiment, the fraction is 0.9%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 7%. In another embodiment, the fraction is 8%. In another embodiment, the fraction is 9%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 55%. In another embodiment, the fraction is 60%. In another embodiment, the fraction is 65%. In another embodiment, the fraction is 70%. In another embodiment, the fraction is 75%. In another embodiment, the fraction is 80%. In another embodiment, the fraction is 85%. In another embodiment, the fraction is 90%. In another embodiment, the fraction is 91%. In another embodiment, the fraction is 92%. In another embodiment, the fraction is 93%. In another embodiment, the fraction is 94%. In another embodiment, the fraction is 95%. In another embodiment, the fraction is 96%. In another embodiment, the fraction is 97%. In another embodiment, the fraction is 98%. In another embodiment, the fraction is 99%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, 0.1% of the residues of a given nucleoside (i.e., uridine, cytidine, guanosine, or adenosine) are modified. In another embodiment, the fraction of modified residues is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.7%. In another embodiment, the fraction is 0.8%. In another embodiment, the fraction is 0.9%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 7%. In another embodiment, the fraction is 8%. In another embodiment, the fraction is 9%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 55%. In another embodiment, the fraction is 60%. In another embodiment, the fraction is 65%. In another embodiment, the fraction is 70%. In another embodiment, the fraction is 75%. In another embodiment, the fraction is 80%. In another embodiment, the fraction is 85%. In another embodiment, the fraction is 90%. In another embodiment, the fraction is 91%. In another embodiment, the fraction is 92%. In another embodiment, the fraction is 93%. In another embodiment, the fraction is 94%. In another embodiment, the fraction is 95%. In another embodiment, the fraction is 96%. In another embodiment, the fraction is 97%. In another embodiment, the fraction is 98%. In another embodiment, the fraction is 99%. In another embodiment, the fraction is 100%. In another embodiment, the fraction of the given nucleotide that is modified is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, a nucleoside-modified RNA of the present invention is translated in the cell more efficiently than an unmodified RNA molecule with the same sequence. In another embodiment, the nucleoside-modified RNA exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 4-fold factor. In another embodiment, translation is enhanced by a 5-fold factor. In another embodiment, translation is enhanced by a 6-fold factor. In another embodiment, translation is enhanced by a 7-fold factor. In another embodiment, translation is enhanced by a 8-fold factor. In another embodiment, translation is enhanced by a 9-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts.

In another embodiment, the nucleoside-modified antigen-encoding RNA of the present invention induces a significantly more robust adaptive immune response as compared with an unmodified in vitro-synthesized RNA molecule of the same sequence. In another embodiment, the modified RNA molecule induces an adaptive immune response that is 2-fold greater than its unmodified counterpart. In another embodiment, the adaptive immune response is increased by a 3-fold factor. In another embodiment, the adaptive immune response is increased by a 4-fold factor. In another embodiment the adaptive immune response is increased by a 5-fold factor. In another embodiment, the adaptive immune response is increased by a 6-fold factor. In another embodiment, the adaptive immune response is increased by a 7-fold factor. In another embodiment, the adaptive immune response is increased by a 8-fold factor. In another embodiment, the adaptive immune response is increased by a 9-fold factor. In another embodiment, the adaptive immune response is increased by a 10-fold factor. In another embodiment, the adaptive immune response is increased by a 15-fold factor. In another embodiment, the adaptive immune response is increased by a 20-fold factor. In another embodiment, the adaptive immune response is increased by a 50-fold factor. In another embodiment, the adaptive immune response is increased by a 100-fold factor. In another embodiment, the adaptive immune response is increased by a 200-fold factor. In another embodiment, the adaptive immune response is increased by a 500-fold factor. In another embodiment, the adaptive immune response is increased by a 1000-fold factor. In another embodiment, the adaptive immune response is increased by a 2000-fold factor. In another embodiment, the adaptive immune response is increased by another fold difference.

In another embodiment, "induces significantly more robust adaptive immune response" refers to a detectable increase in an adaptive immune response. In another embodiment, the term refers to a fold increase in the adaptive immune response (e.g., 1 of the fold increases enumerated above). In another embodiment, the term refers to an increase such that the nucleoside-modified RNA can be administered at a lower dose or frequency than an unmodified RNA molecule while still inducing a similarly effective adaptive immune response. In another embodiment, the increase is such that the nucleoside-modified RNA can be administered using a single dose to induce an effective adaptive immune response.

In another embodiment, the nucleoside-modified RNA of the present invention exhibits significantly less innate immunogenicity than an unmodified in vitro-synthesized RNA molecule of the same sequence. In another embodiment, the modified RNA molecule exhibits an innate immune response that is 2-fold less than its unmodified counterpart. In another embodiment, innate immunogenicity is reduced by a 3-fold factor. In another embodiment, innate immunogenicity is reduced by a 4-fold factor. In another embodiment, innate immunogenicity is reduced by a 5-fold factor. In another embodiment, innate immunogenicity is reduced by a 6-fold factor. In another embodiment, innate immunogenicity is reduced by a 7-fold factor. In another embodiment, innate immunogenicity is reduced by a 8-fold factor. In another embodiment, innate immunogenicity is reduced by a 9-fold factor. In another embodiment, innate immunogenicity is reduced by a 10-fold factor. In another embodiment, innate immunogenicity is reduced by a 15-fold factor. In another embodiment, innate immunogenicity is reduced by a 20-fold factor. In another embodiment, innate immunogenicity is reduced by a 50-fold factor. In another embodiment, innate immunogenicity is reduced by a 100-fold factor. In another embodiment, innate immunogenicity is reduced by a 200-fold factor. In another embodiment, innate immunogenicity is reduced by a 500-fold factor. In another embodiment, innate immunogenicity is reduced by a 1000-fold factor. In another embodiment, innate immunogenicity is reduced by a 2000-fold factor. In another embodiment, innate immunogenicity is reduced by another fold difference.

In another embodiment, "exhibits significantly less innate immunogenicity" refers to a detectable decrease in innate immunogenicity. In another embodiment, the term refers to a fold decrease in innate immunogenicity (e.g., 1 of the fold decreases enumerated above). In another embodiment, the term refers to a decrease such that an effective amount of the nucleoside-modified RNA can be administered without triggering a detectable innate immune response. In another embodiment, the term refers to a decrease such that the nucleoside-modified RNA can be repeatedly administered without eliciting an innate immune response sufficient to detectably reduce production of the protein encoded by the modified RNA. In another embodiment, the decrease is such that the nucleoside-modified RNA can be repeatedly administered without eliciting an innate immune response sufficient to eliminate detectable production of the protein encoded by the modified RNA.

Lipid Nanoparticle

In one embodiment, delivery of nucleoside-modified RNA comprises any suitable delivery method, including exemplary RNA transfection methods described elsewhere herein. In certain embodiments, delivery of a nucleoside-modified RNA to a subject comprises mixing the nucleoside-modified RNA with a transfection reagent prior to the step of contacting. In another embodiment, a method of present invention further comprises administering nucleoside-modified RNA together with the transfection reagent. In another embodiment, the transfection reagent is a cationic lipid reagent. In another embodiment, the transfection reagent is a cationic polymer reagent.

In another embodiment, the transfection reagent is a lipid-based transfection reagent. In another embodiment, the transfection reagent is a protein-based transfection reagent. In another embodiment, the transfection reagent is a carbohydrate-based transfection reagent. In another embodiment, the transfection reagent is a cationic lipid-based transfection reagent. In another embodiment, the transfection reagent is a cationic polymer-based transfection reagent. In another embodiment, the transfection reagent is a polyethyleneimine based transfection reagent. In another embodiment, the transfection reagent is calcium phosphate. In another embodiment, the transfection reagent is Lipofectin®, Lipofectamine®, or TransIT®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids, which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In one embodiment, the composition comprises a lipid nanoparticle (LNP) and one or more nucleic acid molecules described herein. For example, in one embodiment, the composition comprises an LNP and one or more nucleoside-modified RNA molecules encoding one or more antigens, adjuvants, or a combination thereof.

The term "lipid nanoparticle" refers to a particle having at least one dimension on the order of nanometers (e.g., 1-1,000 nm), which includes one or more lipids, for example a lipid of Formula (I), (II) or (III). In some embodiments, lipid nanoparticles are included in a formulation comprising a nucleoside-modified RNA as described herein. In some embodiments, such lipid nanoparticles comprise a cationic lipid (e.g., a lipid of Formula (I), (II) or (III)) and one or more excipient selected from neutral lipids, charged lipids, steroids and polymer conjugated lipids (e.g., a pegylated lipid such as a pegylated lipid of structure (IV), such as compound Iva). In some embodiments, the nucleoside-modified RNA is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, the nucleoside-modified RNA, when present in the lipid nanoparticles, is resistant in aqueous solution to degradation with a nuclease.

The LNP may comprise any lipid capable of forming a particle to which the one or more nucleic acid molecules are attached, or in which the one or more nucleic acid molecules are encapsulated. The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the LNP comprises one or more cationic lipids, and one or more stabilizing lipids. Stabilizing lipids include neutral lipids and pegylated lipids.

In one embodiment, the LNP comprises a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

In certain embodiments, the cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl)cholesterol (DC-Chol), N-(1-(2,3-dioleoyloxy)propyl)-N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Suitable amino lipids useful in the invention include those described in WO 2012/016184, incorporated herein by reference in its entirety. Representative amino lipids include, but are not limited to, 1,2-dilinoleyoxy-3-(dimethylamino) acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

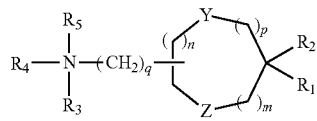

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In one embodiment, $R_1$ and $R^2$ are each linoleyl, and the amino lipid is a dilinoleyl amino lipid. In one embodiment, the amino lipid is a dilinoleyl amino lipid.

A representative useful dilinoleyl amino lipid has the formula:

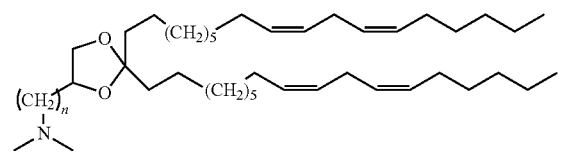

DLin-K-DMA wherein n is 0, 1, 2, 3, or 4.

In one embodiment, the cationic lipid is a DLin-K-DMA. In one embodiment, the cationic lipid is DLin-KC2-DMA (DLin-K-DMA above, wherein n is 2).

In one embodiment, the cationic lipid component of the LNPs has the structure of Formula (I):

(I)

or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In certain embodiments of Formula (I), at least one of $R^1$, $R^{2a}$, $R^{3a}$ or $R^{4a}$ is $C_1$-$C_{12}$ alkyl, or at least one of $L^1$ or $L^2$ is —O(C=O)— or —(C=O)O—. In other embodiments, $R^{1a}$ and $R^{1b}$ are not isopropyl when a is 6 or n-butyl when a is 8.

In still further embodiments of Formula (I), at least one of $R^1$, $R^{2a}$, $R^{3a}$ or $R^{4a}$ is $C_1$-$C_{12}$ alkyl, or at least one of $L^1$ or $L^2$ is —O(C=O)— or —(C=O)O—; and $R^{1a}$ and $R^{1b}$ are not isopropyl when a is 6 or n-butyl when a is 8.

In other embodiments of Formula (I), $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula (I), any one of $L^1$ or $L^2$ may be —O(C=O)— or a carbon-carbon double bond. $L^1$ and $L^2$ may each be —O(C=O)— or may each be a carbon-carbon double bond.

In some embodiments of Formula (I), one of $L^1$ or $L^2$ is —O(C=O)—. In other embodiments, both $L^1$ and $L^2$ are —O(C=O)—.

In some embodiments of Formula (I), one of $L^1$ or $L^2$ is —(C=O)O—. In other embodiments, both $L^1$ and $L^2$ are —(C=O)O—.

In some other embodiments of Formula (I), one of $L^1$ or $L^2$ is a carbon-carbon double bond. In other embodiments, both $L^1$ and $L^2$ are a carbon-carbon double bond.

In still other embodiments of Formula (I), one of $L^1$ or $L^2$ is —O(C=O)— and the other of $L^1$ or $L^2$ is —(C=O)O—. In more embodiments, one of $L^1$ or $L^2$ is —O(C=O)— and the other of $L^1$ or $L^2$ is a carbon-carbon double bond. In yet more embodiments, one of $L^1$ or $L^2$ is —(C=O)O— and the other of $L^1$ or $L^2$ is a carbon-carbon double bond.

It is understood that "carbon-carbon" double bond, as used throughout the specification, refers to one of the following structures:

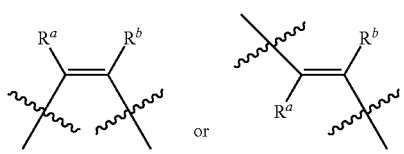

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula (I) have the following structure (Ia):

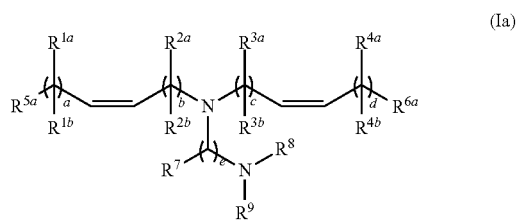

In other embodiments, the lipid compounds of Formula (I) have the following structure (Ib):

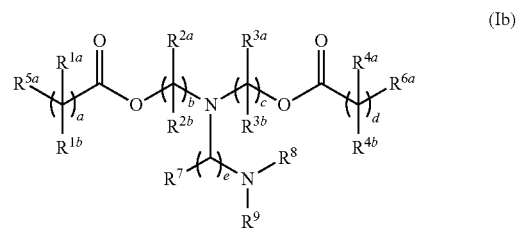

In yet other embodiments, the lipid compounds of Formula (I) have the following structure (Ic):

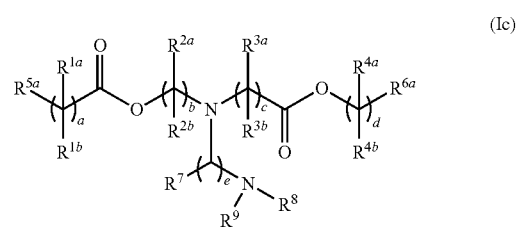

In certain embodiments of the lipid compound of Formula (I), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula (I), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula (I), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain other embodiments of Formula (I), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula (I), a and d are the same. In some other embodiments, b and c are the same. In some other specific embodiments, a and d are the same and b and c are the same.

The sum of a and b and the sum of c and d in Formula (I) are factors which may be varied to obtain a lipid of Formula (I) having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a, b, c and d are selected such the sum of a and b and the sum of c and d is 12 or greater.

In some embodiments of Formula (I), e is 1. In other embodiments, e is 2.

The substituents at $R^{1a}$, $R^{2a}$, $R^{3a}$ and $R^{4a}$ of Formula (I) are not particularly limited. In certain embodiments $R^{1a}$, $R^{2a}$, $R^{3a}$ and $R^{4a}$ are H at each occurrence. In certain other embodiments, at least one of $R^{1a}$, $R^{2a}$, $R^{3a}$ and $R^{4a}$ is $C_1$-$C_{12}$ alkyl. In certain other embodiments, at least one of $R^{1a}$, $R^{2a}$, $R^{3a}$ and $R^{4a}$ is $C_1$-$C_8$ alkyl. In certain other embodiments, at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (I), $R^{1a}$, Rib, $R^{4a}$ and $R^{4b}$ are $C_1$-$C_{12}$ alkyl at each occurrence.

In further embodiments of Formula (I), at least one of $R^{1b}$, $R^{2b}$, $R^{3b}$ and $R^{4b}$ is H or Rib, $R^{2b}$, $R^{3b}$ and $R^{4b}$ are H at each occurrence.

In certain embodiments of Formula (I), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (I) are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments, the cycloalkyl may be substituted or not substituted. In certain other embodiments, the cycloalkyl is substituted with $C_1$-$C_{12}$ alkyl, for example tert-butyl.

The substituents at $R^7$ are not particularly limited in the foregoing embodiments of Formula (I). In certain embodiments, at least one $R^7$ is H. In some other embodiments, $R^7$ is H at each occurrence. In certain other embodiments $R^7$ is $C_1$-$C_{12}$ alkyl.

In certain other of the foregoing embodiments of Formula (I), one of $R^8$ or $R^9$ is methyl. In other embodiments, both $R^8$ and $R^9$ are methyl.

In some different embodiments of Formula (I), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In various different embodiments, the lipid of Formula (I) has one of the structures set forth in Table 1 below.

TABLE 1

Representative Lipids of Formula (I)

| No. | Structure | Prep. Method |
|---|---|---|
| I-1 | 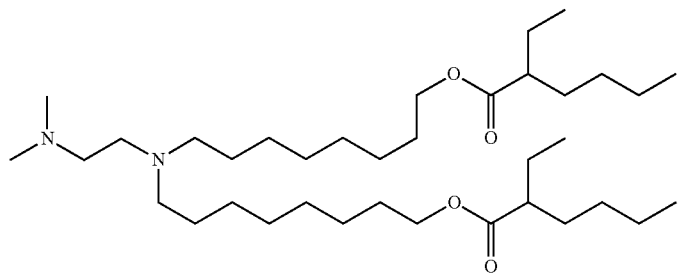 [SMILES: CCCCC(CC)C(=O)OCCCCCCCCN(CCCCCCCCOC(=O)C(CC)CCCC)CCN(C)C] | B |

TABLE 1-continued
Representative Lipids of Formula (I)
| No. | Structure | Prep. Method |
|---|---|---|
| I-2 | 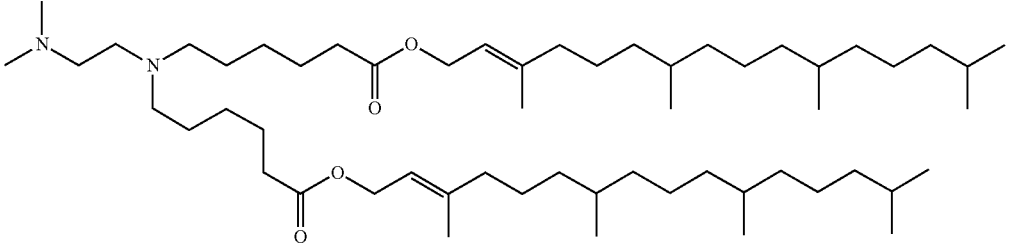 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | A |
| I-3 | 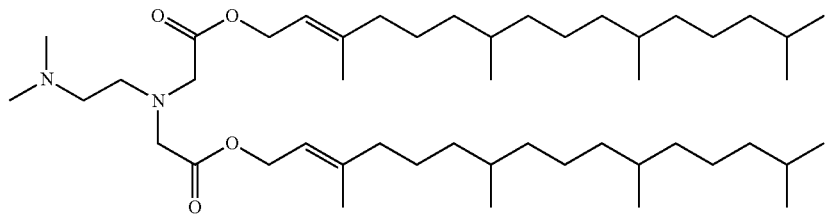 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | A |
| I-4 | 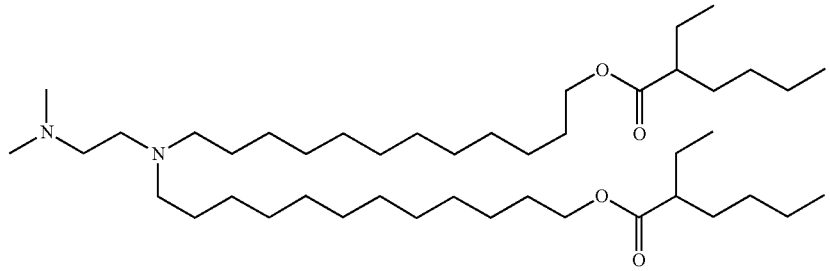 [SMILES: CCCCC(CC)C(=O)OCCCCCCCCCCCCN(CCCCCCCCCCCCOC(=O)C(CC)CCCC)CCN(C)C] | B |
| I-5 | 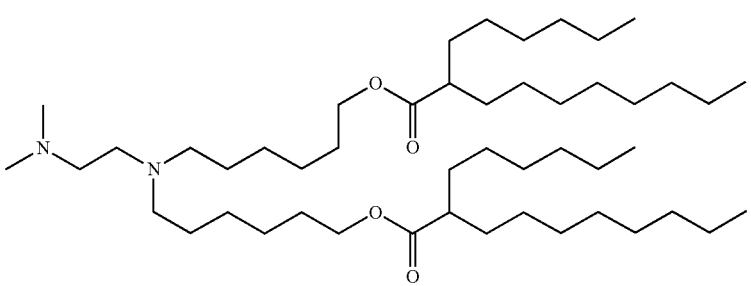 [SMILES: CCCCCCCCC(CCCCCC)C(=O)OCCCCCCN(CCCCCCOC(=O)C(CCCCCC)CCCCCCCC)CCN(C)C] | B |
| I-6 | 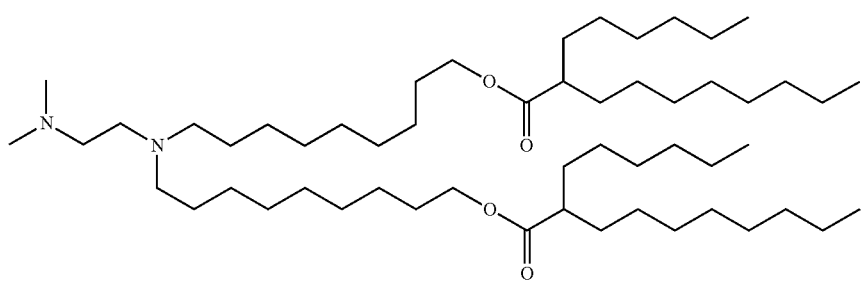 [SMILES: CCCCCCCCC(CCCCCC)C(=O)OCCCCCCCCCN(CCCCCCCCCOC(=O)C(CCCCCC)CCCCCCCC)CCN(C)C] | B |

TABLE 1-continued

Representative Lipids of Formula (I)

| No. | Structure | Prep. Method |
|---|---|---|
| I-7 | 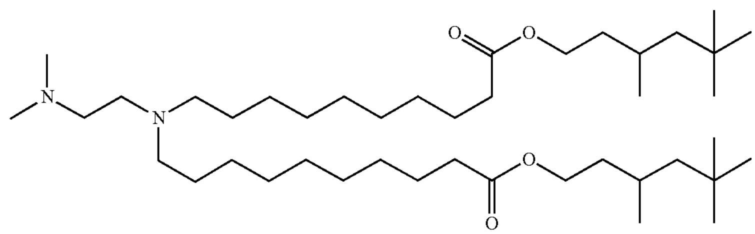 [SMILES: CC(CCOC(=O)CCCCCCCCCN(CCCCCCCCCC(=O)OCCC(C)CC(C)(C)C)CCN(C)C)CC(C)(C)C] | A |
| I-8 | 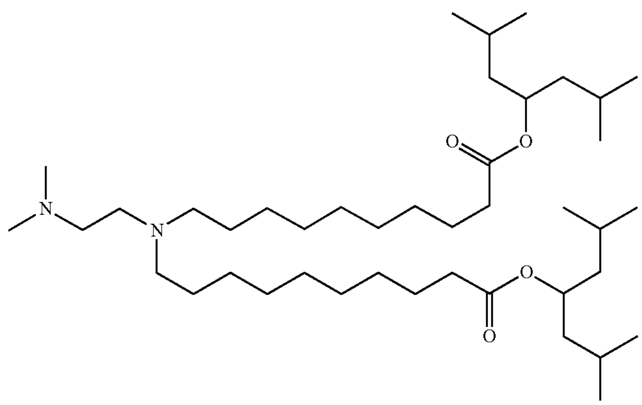 [SMILES: CC(C)CC(CC(C)C)OC(=O)CCCCCCCCCN(CCCCCCCCCC(=O)OC(CC(C)C)CC(C)C)CCN(C)C] | A |
| I-9 | 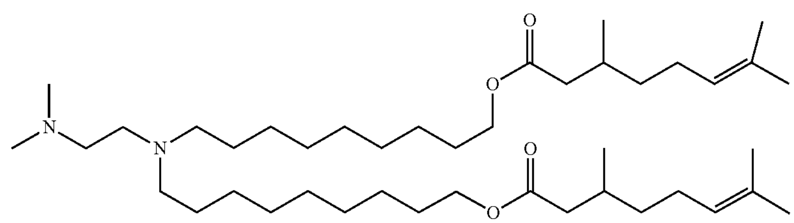 [SMILES: CC(C)=CCCC(C)CC(=O)OCCCCCCCCCN(CCCCCCCCCOC(=O)CC(C)CCC=C(C)C)CCN(C)C] | B |
| I-10 | 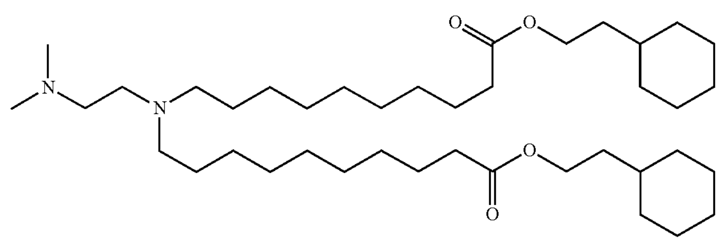 [SMILES: CN(C)CCN(CCCCCCCCCC(=O)OCCC1CCCCC1)CCCCCCCCCC(=O)OCCC1CCCCC1] | A |
| I-11 | 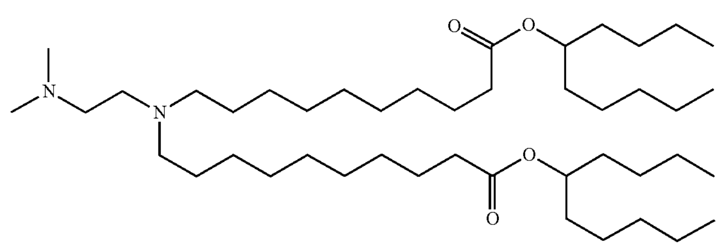 [SMILES: CCCCCC(CCCC)OC(=O)CCCCCCCCCN(CCCCCCCCCC(=O)OC(CCCC)CCCCC)CCN(C)C] | A |

TABLE 1-continued

Representative Lipids of Formula (I)

| No. | Structure | Prep. Method |
|---|---|---|
| I-12 | 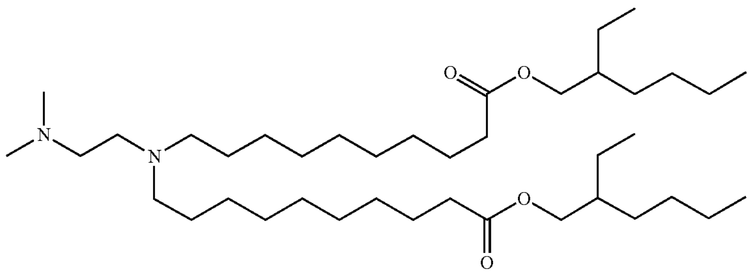 [SMILES: CCCCC(CC)COC(=O)CCCCCCCCCN(CCCCCCCCCC(=O)OCC(CC)CCCC)CCN(C)C] | A |
| I-13 | 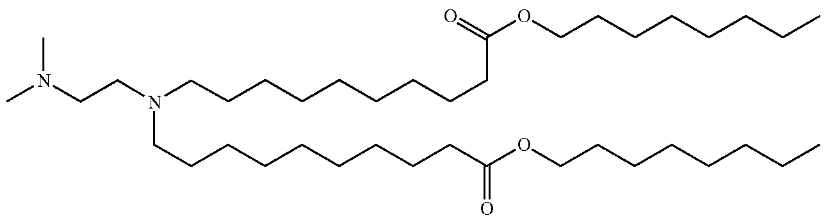 [SMILES: CCCCCCCCOC(=O)CCCCCCCCCN(CCCCCCCCCC(=O)OCCCCCCCC)CCN(C)C] | A |
| I-14 | 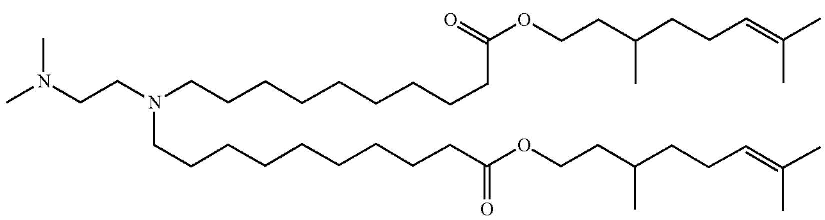 [SMILES: CC(C)=CCCC(C)CCOC(=O)CCCCCCCCCN(CCCCCCCCCC(=O)OCCC(C)CCC=C(C)C)CCN(C)C] | A |
| I-15 | 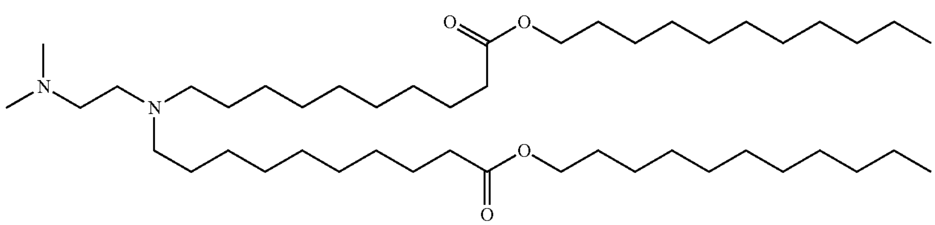 [SMILES: CCCCCCCCCCCOC(=O)CCCCCCCCCN(CCCCCCCCCC(=O)OCCCCCCCCCCC)CCN(C)C] | A |
| I-16 | 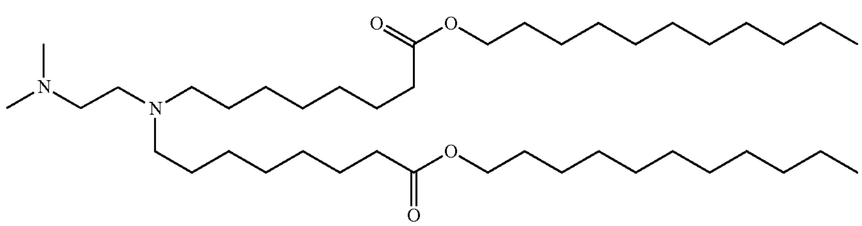 [SMILES: CCCCCCCCCCCOC(=O)CCCCCCCN(CCCCCCCC(=O)OCCCCCCCCCCC)CCN(C)C] | A |
| I-17 | 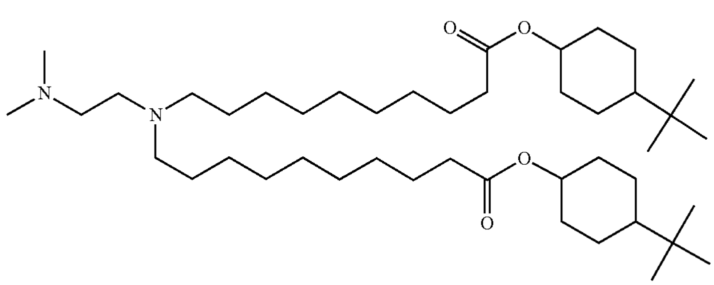 [SMILES: CN(C)CCN(CCCCCCCCCC(=O)OC1CCC(C(C)(C)C)CC1)CCCCCCCCCC(=O)OC1CCC(C(C)(C)C)CC1] | A |

TABLE 1-continued

Representative Lipids of Formula (I)

| No. | Structure | Prep. Method |
|---|---|---|
| I-18 | 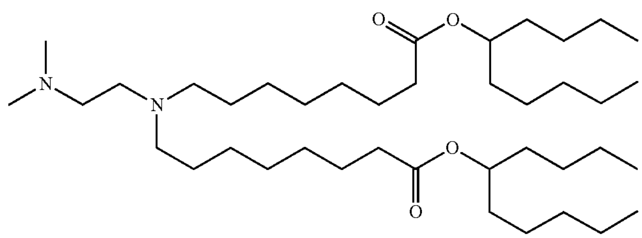 [SMILES: CCCCCC(CCCC)OC(=O)CCCCCCCN(CCCCCCCC(=O)OC(CCCC)CCCCC)CCN(C)C] | A |
| I-19 | 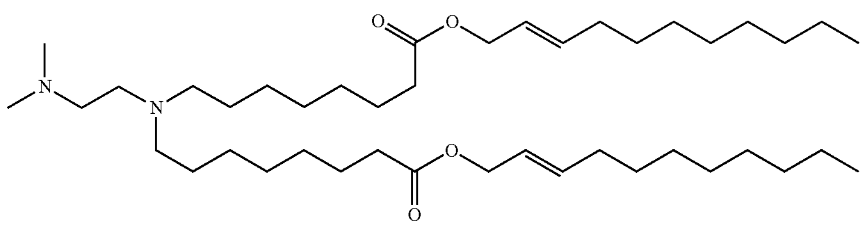 [SMILES: CCCCCCCC/C=C/COC(=O)CCCCCCCN(CCCCCCCC(=O)OC/C=C/CCCCCCCC)CCN(C)C] | A |
| I-20 | 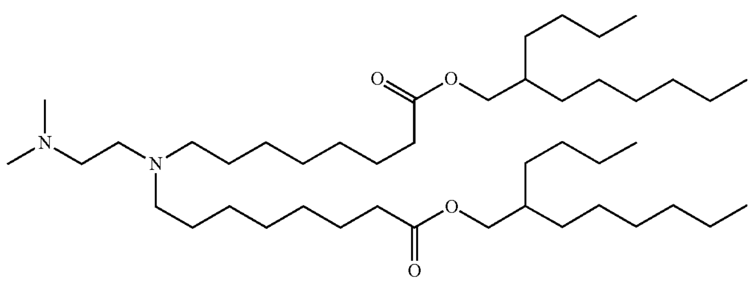 [SMILES: CCCCCCC(CCCC)COC(=O)CCCCCCCN(CCCCCCCC(=O)OCC(CCCC)CCCCCC)CCN(C)C] | A |
| I-21 | 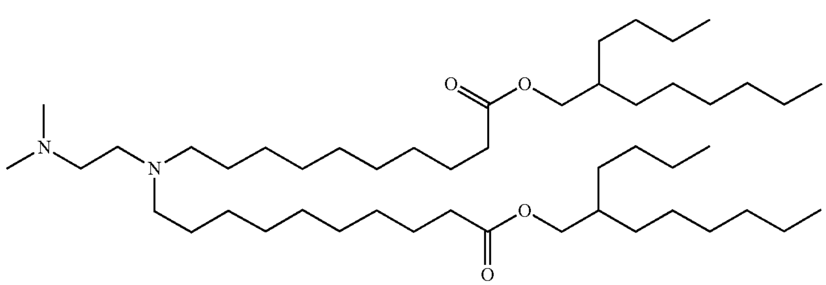 [SMILES: CCCCCCC(CCCC)COC(=O)CCCCCCCCCN(CCCCCCCCCC(=O)OCC(CCCC)CCCCCC)CCN(C)C] | A |
| I-22 | 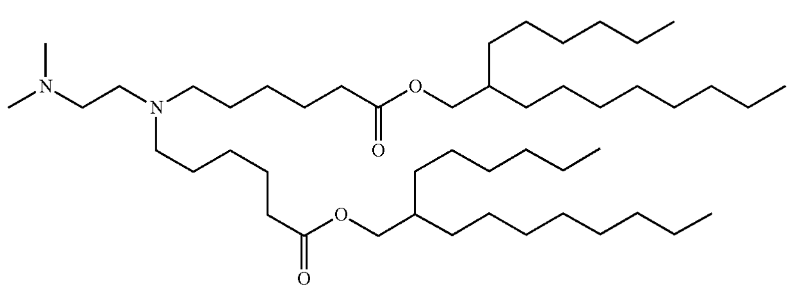 [SMILES: CCCCCCCCC(CCCCCC)COC(=O)CCCCCN(CCCCCC(=O)OCC(CCCCCC)CCCCCCCC)CCN(C)C] | A |

TABLE 1-continued

Representative Lipids of Formula (I)

| No. | Structure | Prep. Method |
|---|---|---|
| I-23 | 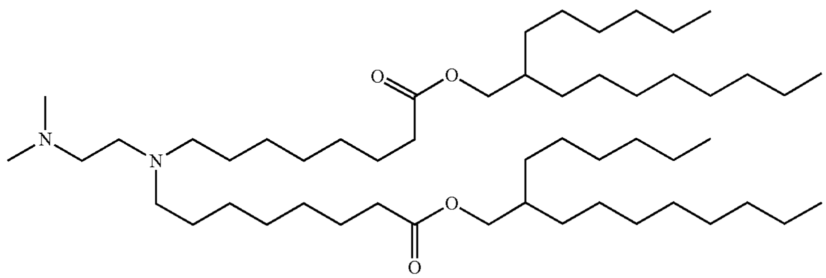 [SMILES: CCCCCCCCC(CCCCCC)COC(=O)CCCCCCCN(CCCCCCCC(=O)OCC(CCCCCC)CCCCCCCC)CCN(C)C] | A |
| I-24 | 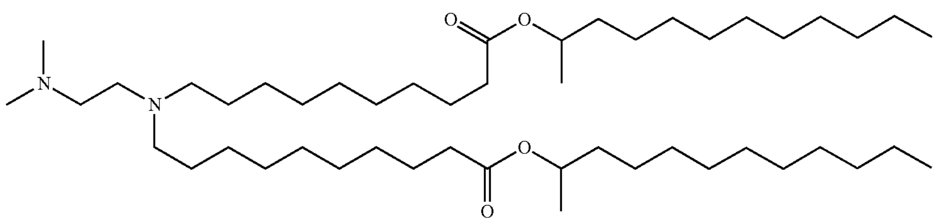 [SMILES: CCCCCCCCCCC(C)OC(=O)CCCCCCCCCN(CCCCCCCCCC(=O)OC(C)CCCCCCCCCC)CCN(C)C] | A |
| I-25 | 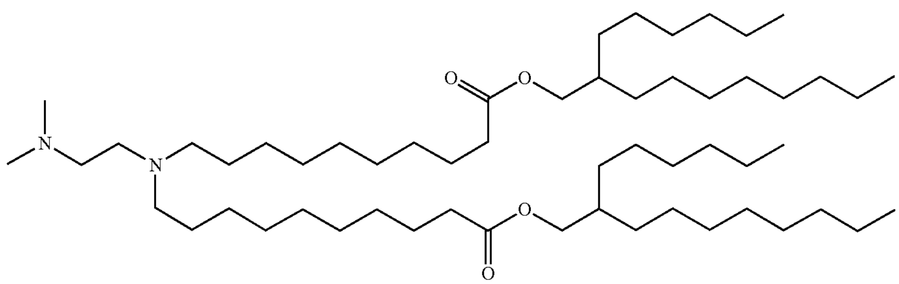 [SMILES: CCCCCCCCC(CCCCCC)COC(=O)CCCCCCCCCN(CCCCCCCCCC(=O)OCC(CCCCCC)CCCCCCCC)CCN(C)C] | A |
| I-26 | 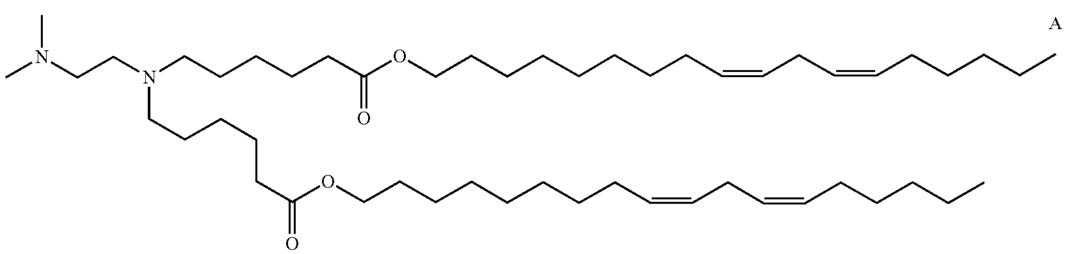 [SMILES: CCCCC/C=C\C/C=C\CCCCCCCCOC(=O)CCCCCN(CCCCCC(=O)OCCCCCCCC/C=C\C/C=C\CCCCC)CCN(C)C] | A |
| I-27 | 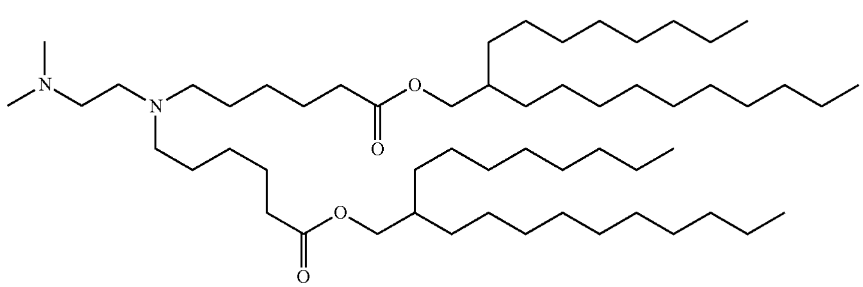 [SMILES: CCCCCCCCCCC(CCCCCCCC)COC(=O)CCCCCN(CCCCCC(=O)OCC(CCCCCCCC)CCCCCCCCCC)CCN(C)C] | A |

TABLE 1-continued

Representative Lipids of Formula (I)

| No. | Structure | Prep. Method |
|---|---|---|
| I-28 | 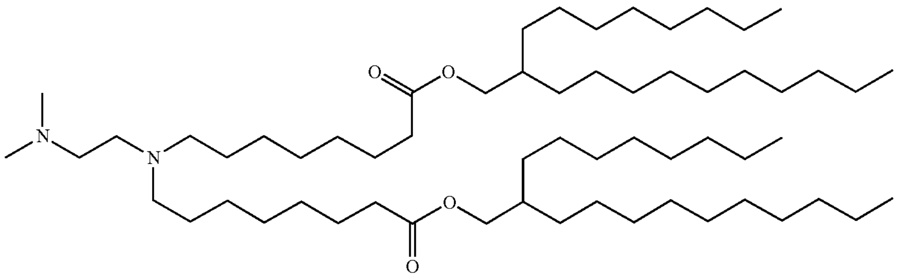 [SMILES: CCCCCCCCCCC(CCCCCCCC)COC(=O)CCCCCCCN(CCCCCCCC(=O)OCC(CCCCCCCC)CCCCCCCCCC)CCN(C)C] | A |
| I-29 | 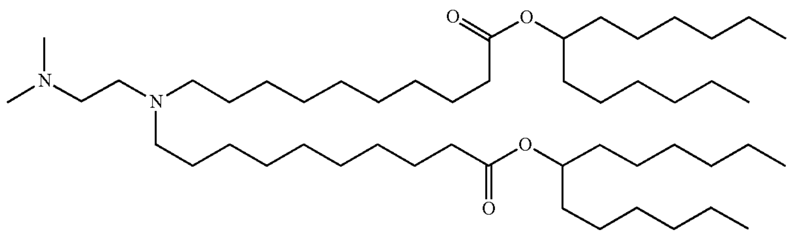 [SMILES: CCCCCCC(CCCCCC)OC(=O)CCCCCCCCCN(CCCCCCCCCC(=O)OC(CCCCCC)CCCCCC)CCN(C)C] | A |
| I-30 | 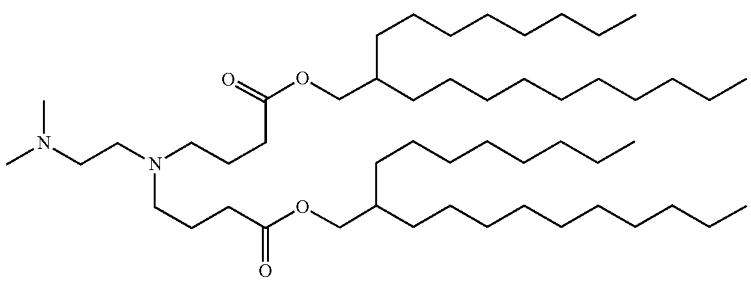 [SMILES: CCCCCCCCCCC(CCCCCCCC)COC(=O)CCCN(CCCC(=O)OCC(CCCCCCCC)CCCCCCCCCC)CCN(C)C] | A |
| I-31 | 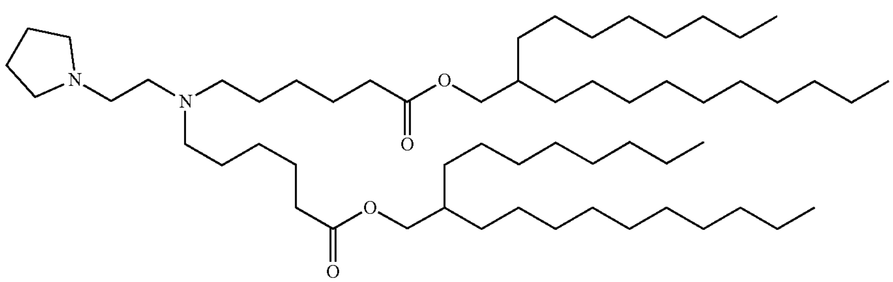 [SMILES: CCCCCCCCCCC(CCCCCCCC)COC(=O)CCCCCN(CCCCCC(=O)OCC(CCCCCCCC)CCCCCCCCCC)CCN1CCCC1] | C |
| I-32 | 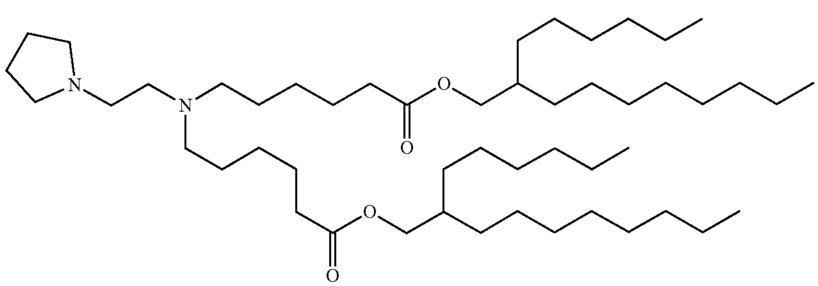 [SMILES: CCCCCCCCC(CCCCCC)COC(=O)CCCCCN(CCCCCC(=O)OCC(CCCCCC)CCCCCCCC)CCN1CCCC1] | C |

TABLE 1-continued

Representative Lipids of Formula (I)

| No. | Structure | Prep. Method |
|---|---|---|
| I-33 | 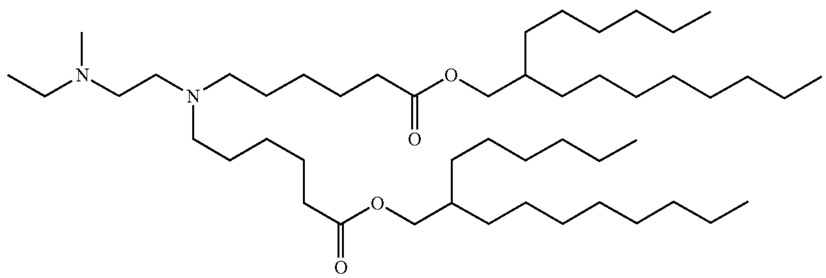 [SMILES: CCCCCCCCC(CCCCCC)COC(=O)CCCCCN(CCCCCC(=O)OCC(CCCCCC)CCCCCCCC)CCN(C)CC] | C |
| I-34 | 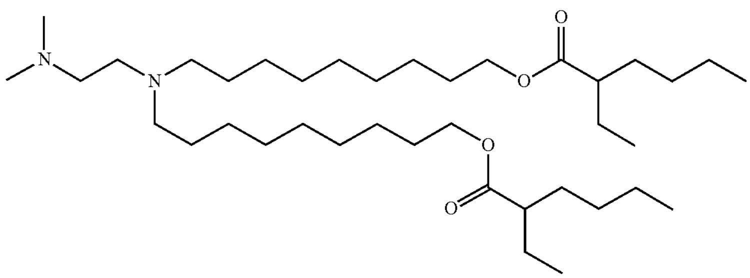 [SMILES: CCCCC(CC)C(=O)OCCCCCCCCCN(CCCCCCCCCOC(=O)C(CC)CCCC)CCN(C)C] | B |
| I-35 | 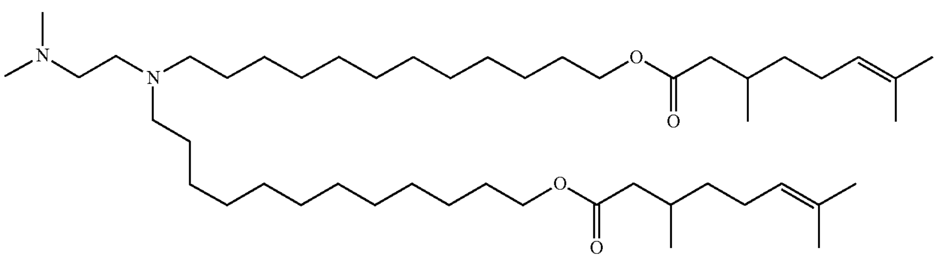 [SMILES: CC(C)=CCCC(C)CC(=O)OCCCCCCCCCCCCN(CCCCCCCCCCCCOC(=O)CC(C)CCC=C(C)C)CCN(C)C] | B |
| I-36 | 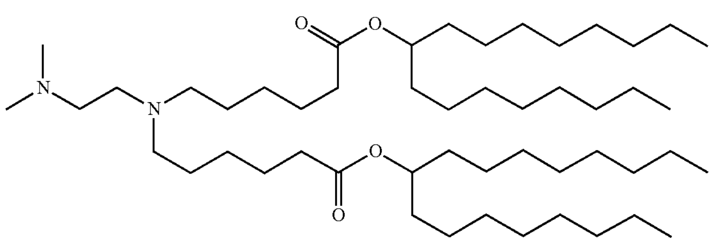 [SMILES: CCCCCCCCC(CCCCCCCC)OC(=O)CCCCCN(CCCCCC(=O)OC(CCCCCCCC)CCCCCCCC)CCN(C)C] | C |
| I-37 | 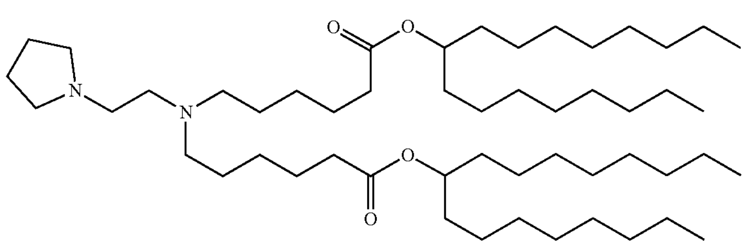 [SMILES: CCCCCCCCC(CCCCCCCC)OC(=O)CCCCCN(CCCCCC(=O)OC(CCCCCCCC)CCCCCCCC)CCN1CCCC1] | C |

TABLE 1-continued

Representative Lipids of Formula (I)

| No. | Structure | Prep. Method |
|---|---|---|
| I-38 | 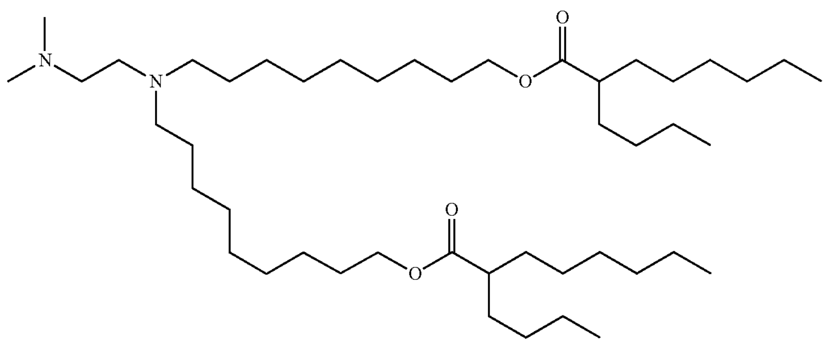 [SMILES: CCCCCCC(CCCC)C(=O)OCCCCCCCCCN(CCCCCCCCCOC(=O)C(CCCC)CCCCCC)CCN(C)C] | B |
| I-39 | 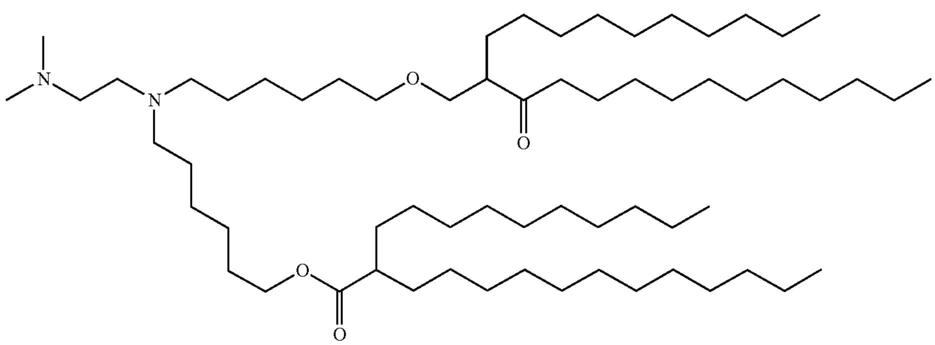 [SMILES: CCCCCCCCCCCCC(CCCCCCCCCC)C(=O)OCCCCCCN(CCCCCCOCC(CCCCCCCCCC)C(=O)CCCCCCCCCCC)CCN(C)C] | B |
| I-40 | 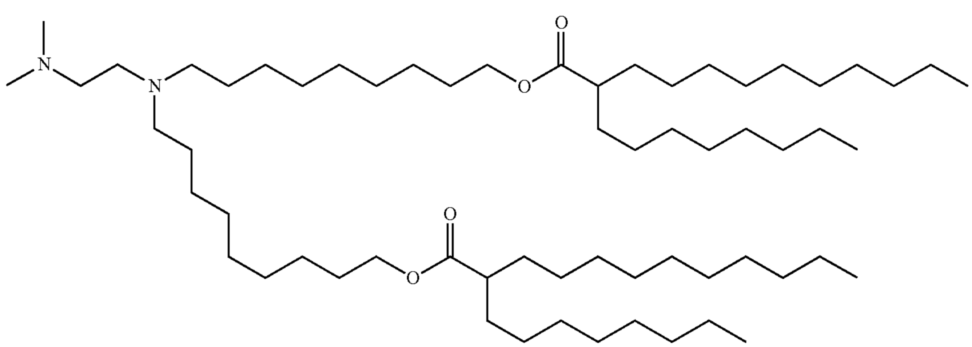 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | B |
| I-41 | 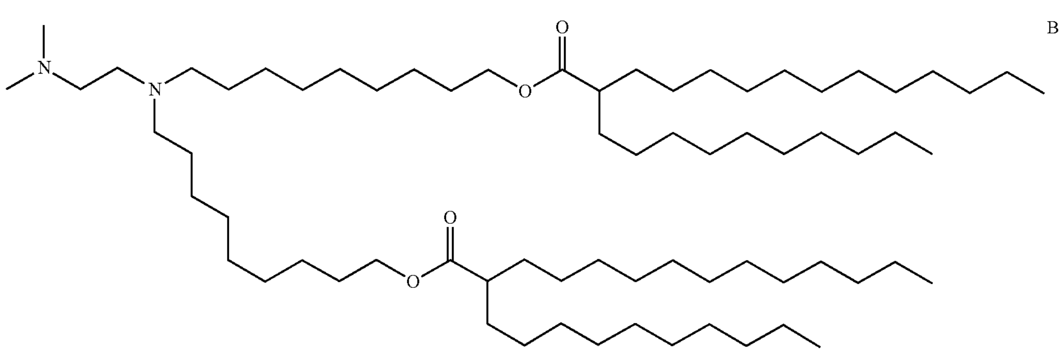 | B |

In some embodiments, the LNPs comprise a lipid of Formula (I), a nucleoside-modified RNA and one or more excipients selected from neutral lipids, steroids and pegylated lipids. In some embodiments the lipid of Formula (I) is compound 1-5. In some embodiments the lipid of Formula (I) is compound 1-6.

In some other embodiments, the cationic lipid component of the LNPs has the structure of Formula (II):

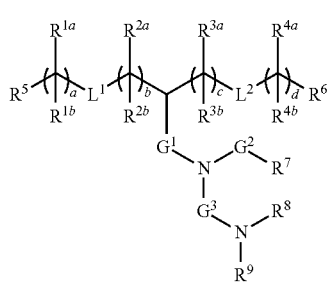

(II)

or a pharmaceutically acceptable salt, tautomer, prodrug or stereoisomer thereof, wherein:

$L^1$ and $L^2$ are each independently —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$, —OC(=O)NR$^a$—, —NR$^a$C(=O)O—, or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$ or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either:
(a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either:
(a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either:
(a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either:
(a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C=O)—, —(C=O)O— or a direct bond. In other embodiments, $G^1$ and $G^2$ are each independently —(C=O)— or a direct bond. In some different embodiments, $L^1$ and $L^2$ are each independently —O(C=O)—, —(C=O)O— or a direct bond; and $G^1$ and $G^2$ are each independently —(C=O)— or a direct bond.

In some different embodiments of Formula (II), $L^1$ and $L^2$ are each independently —C(=O)—, —O—, —S(O)$_x$—, —S—S—, —C(=O)S—, —SC(=O)—, —NR$^a$—, —NR$^a$C(=O)—, —C(=O)NR$^a$—, —NR$^a$C(=O)NR$^a$, —OC(=O)NR$^a$—, —NR$^a$C(=O)O—, —NR$^a$S(O)$_x$NR$^a$—, —NR$^a$S(O)$_x$— or —S(O)$_x$NR$^a$—.

In other of the foregoing embodiments of Formula (II), the lipid compound has one of the following structures (IIA) or (IIB):

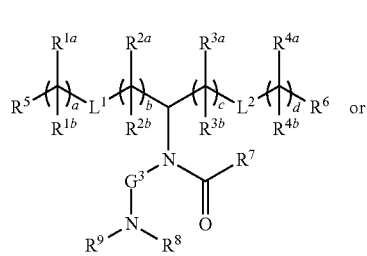

(IIA)

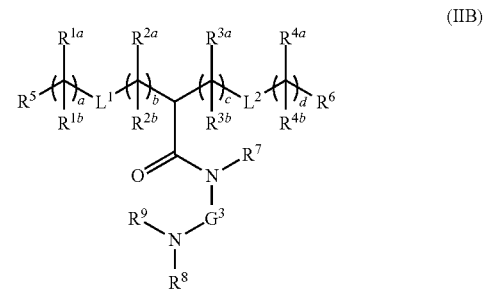

(IIB)

In some embodiments of Formula (II), the lipid compound has structure (IIA). In other embodiments, the lipid compound has structure (IIB).

In any of the foregoing embodiments of Formula (II), one of $L^1$ or $L^2$ is —O(C=O)—. For example, in some embodiments each of $L^1$ and $L^2$ are —O(C=O)—.

In some different embodiments of Formula (II), one of $L^1$ or $L^2$ is —(C=O)O—. For example, in some embodiments each of $L^1$ and $L^2$ is —(C=O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and Rib, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following structures (IIC) or (IID):

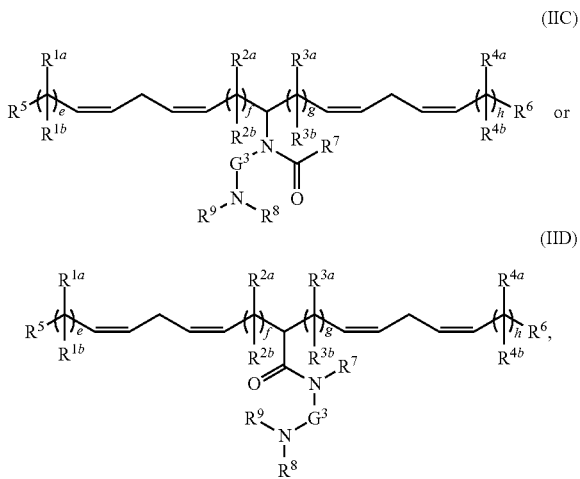

wherein e, f, g and h are each independently an integer from 1 to 12.

In some embodiments of Formula (II), the lipid compound has structure (IIC). In other embodiments, the lipid compound has structure (IID).

In various embodiments of structures (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments, at least one of $R^{1a}$, $R^{2a}$, $R^{3a}$ and $R^{4a}$ is $C_1$-$C_{12}$ alkyl. In certain other embodiments, at least one of $R^{1a}$, $R^{2a}$, $R^{3a}$ and $R^{4a}$ is $C_1$-$C_8$ alkyl. In certain other embodiments, at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_{12}$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments, each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C=O)$OR^b$, —O(C=O)$R^b$, —C(=O)$R^b$, —$OR^b$, —S(O)$_xR^b$, —S—$SR^b$, —C(=O)SR, —SC(=O)$R^b$, —$NR^aR^b$, —$NR^aC$(=O)$R^b$, —C(=O)$NR^aR^b$, —$NR^aC$(=O)$NR^aR^b$, —OC(=O)$NR^aR^b$, —$NR^aC$(O)$OR^b$, —$NR^aS$(O)$_xNR^aR^b$, —$NR^aS$(O)$_xR^b$ or —S(O)$_xNR^aR^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C=O)$OR^b$ or —O(C=O)$R^b$.

In various of the foregoing embodiments of Formula (II), $R^b$ is branched $C_1$-$C_{15}$ alkyl. For example, in some embodiments $R^b$ has one of the following structures:

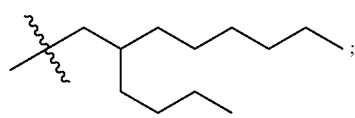

-continued

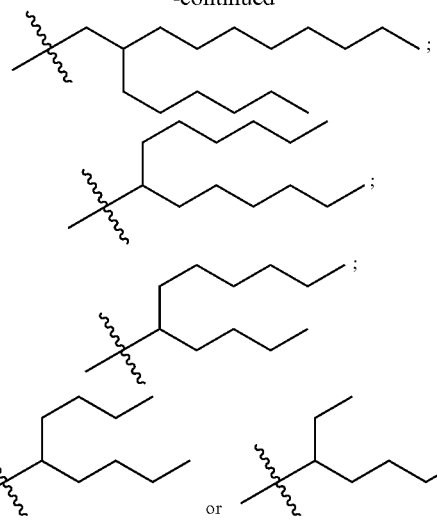

In certain other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In still other embodiments of the foregoing lipids of Formula (II), $G^3$ is $C_2$-$C_4$ alkylene, for example $C_3$ alkylene.

In various different embodiments, the lipid compound has one of the structures set forth in Table 2 below.

TABLE 2

Representative Lipids of Formula (II)

| No. | Structure | Prep. Method |
|---|---|---|
| II-1 | 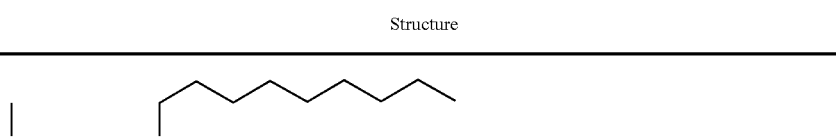 | D |
| II-2 | 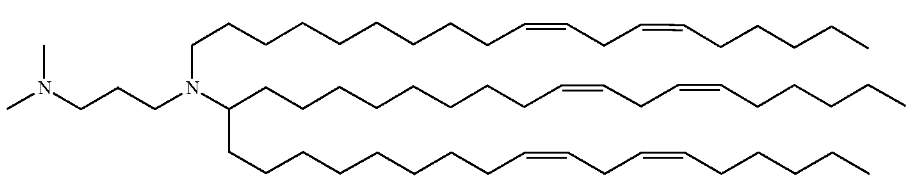 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | D |

TABLE 2-continued

Representative Lipids of Formula (II)

| No. | Structure | Prep. Method |
|---|---|---|
| II-3 | 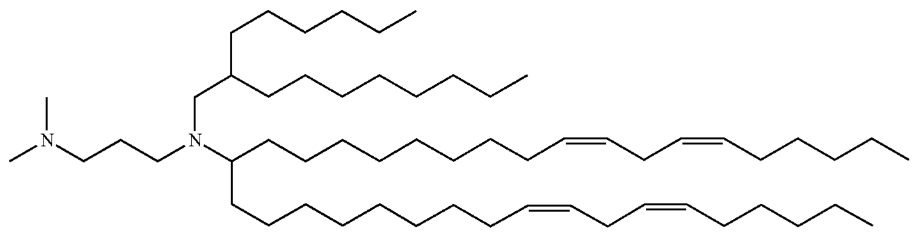 [SMILES: CCCCC/C=C\C/C=C\CCCCCCCCC(CCCCCCCC/C=C\C/C=C\CCCCC)N(CCCN(C)C)CC(CCCCCC)CCCCCCCC] | D |
| II-4 | 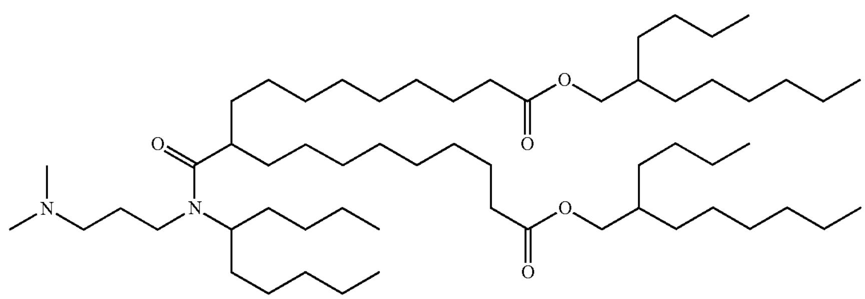 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | E |
| II-5 | 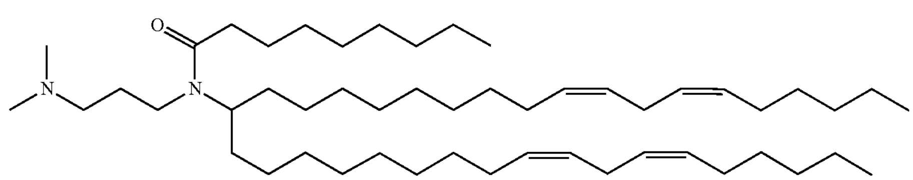 [SMILES: CCCCC/C=C\C/C=C\CCCCCCCCC(CCCCCCCC/C=C\C/C=C\CCCCC)N(CCCN(C)C)C(=O)CCCCCCCC] | D |
| II-6 | 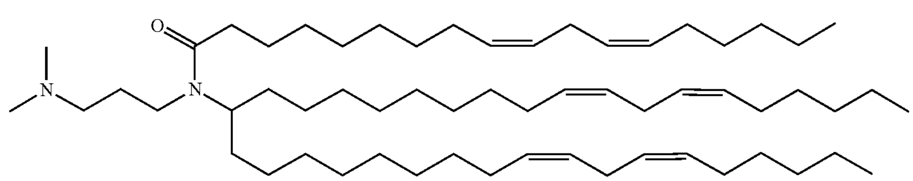 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | D |
| II-7 | 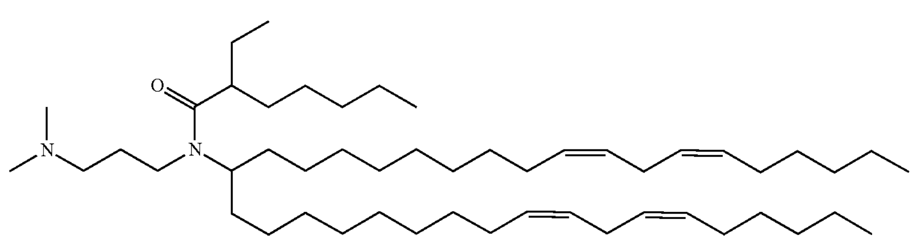 [SMILES: CCCCC/C=C\C/C=C\CCCCCCCCC(CCCCCCCC/C=C\C/C=C\CCCCC)N(CCCN(C)C)C(=O)C(CC)CCCCC] | D |
| II-8 | 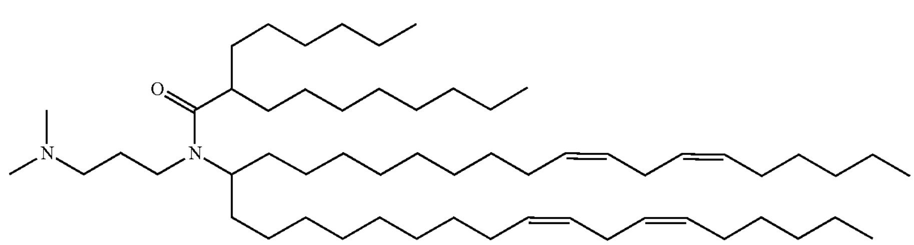 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | D |

TABLE 2-continued

Representative Lipids of Formula (II)

| No. | Structure | Prep. Method |
|---|---|---|
| II-9 | 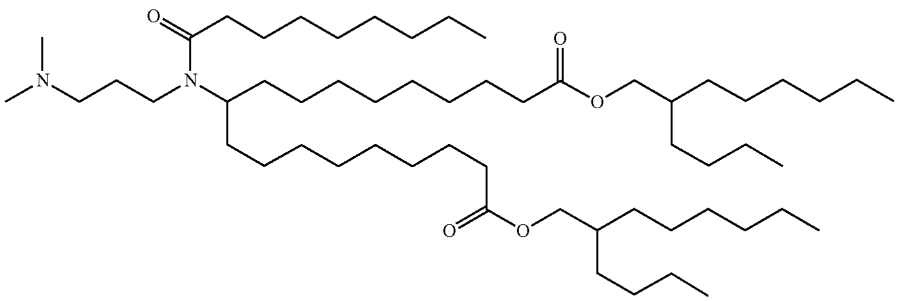 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | D |
| II-10 | 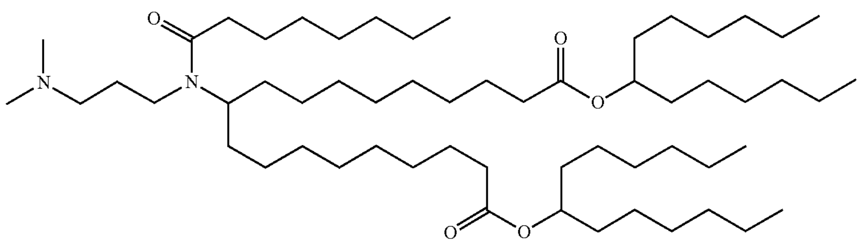 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | D |
| II-11 | 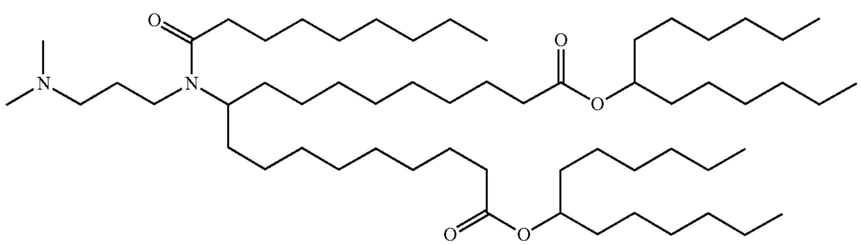 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | D |
| II-12 | 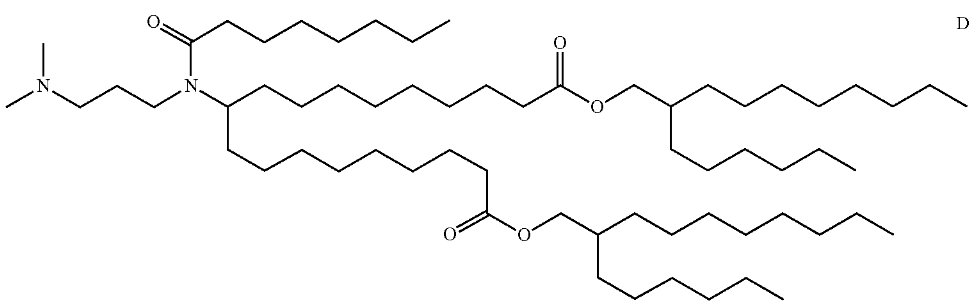 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | D |
| II-13 | 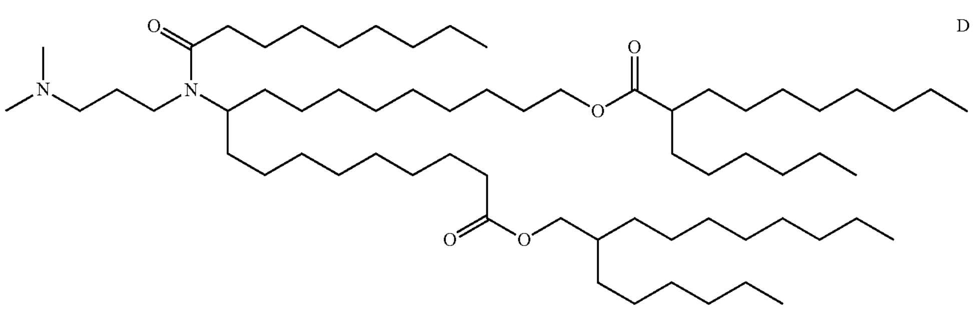 [SMILES: CCCCCCCCC(=O)N(CCCN(C)C)C(CCCCCCCCCOC(=O)C(CCCCCC)CCCCCCCC)CCCCCCCCC(=O)OCC(CCCCCC)CCCCCCCC] | D |

TABLE 2-continued
Representative Lipids of Formula (II)
| No. | Structure | Prep. Method |
|---|---|---|
| II-14 | 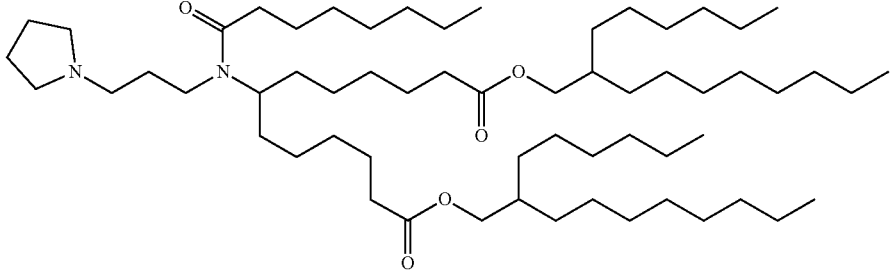 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | D |
| II-15 | 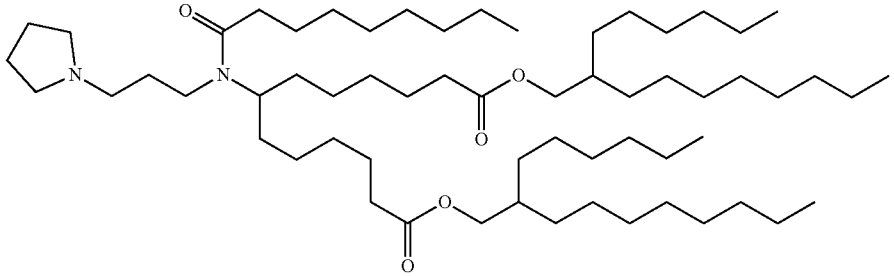 [SMILES: CCCCCCCCC(=O)N(CCCN1CCCC1)C(CCCCCC(=O)OCC(CCCCCC)CCCCCCCC)CCCCCC(=O)OCC(CCCCCC)CCCCCCCC] | D |
| II-16 | 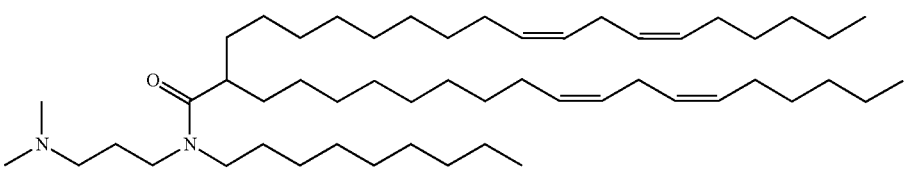 [SMILES: CCCCC/C=C\C/C=C\CCCCCCCCC(CCCCCCCC/C=C\C/C=C\CCCCC)C(=O)N(CCCCCCCCC)CCCN(C)C] | E |
| II-17 | 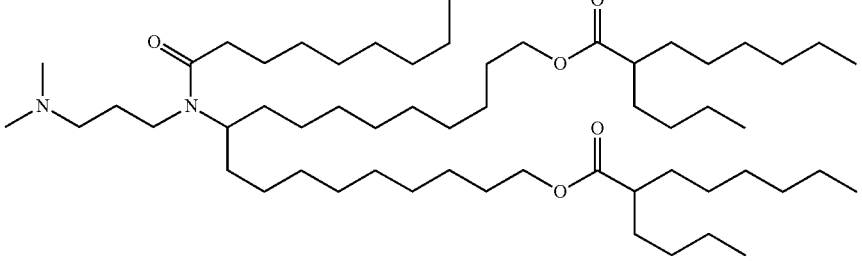 | D |
| II-18 | 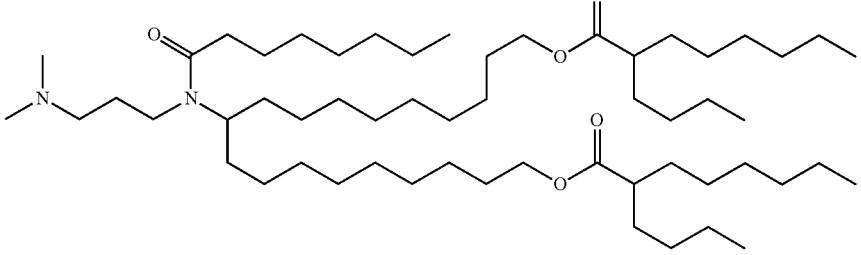 | D |

TABLE 2-continued

Representative Lipids of Formula (II)

| No. | Structure | Prep. Method |
|---|---|---|
| II-19 | 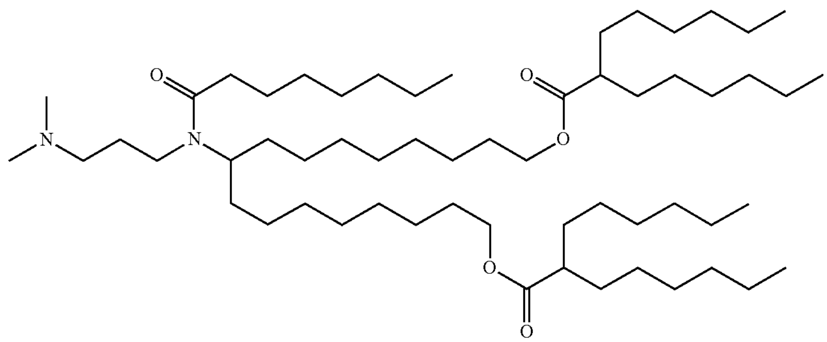 [SMILES: CCCCCCCC(=O)N(CCCN(C)C)C(CCCCCCCCOC(=O)C(CCCCCC)CCCCCC)CCCCCCCCOC(=O)C(CCCCCC)CCCCCC] | D |
| II-20 | 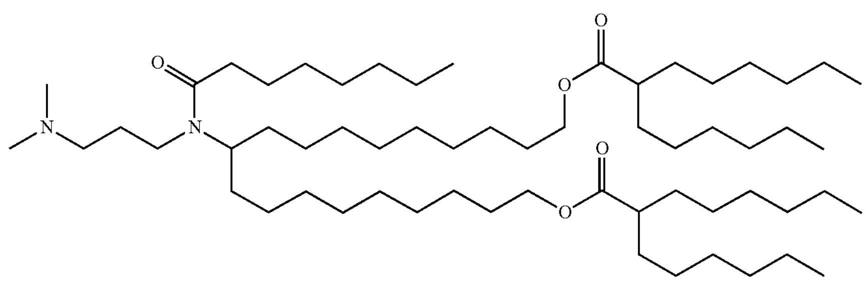 [SMILES: CCCCCCCC(=O)N(CCCN(C)C)C(CCCCCCCCCOC(=O)C(CCCCCC)CCCCCC)CCCCCCCCCOC(=O)C(CCCCCC)CCCCCC] | D |
| II-21 | 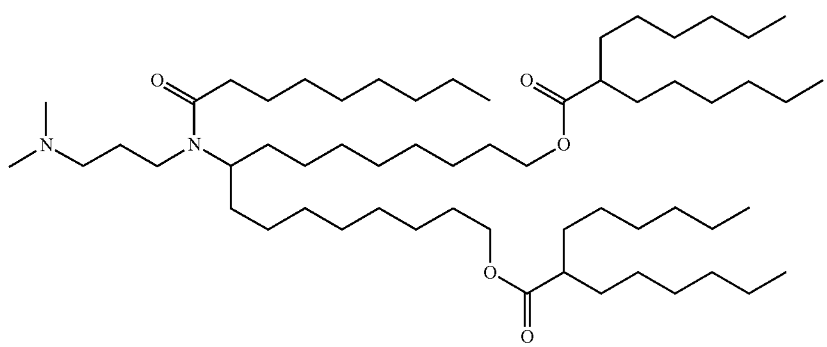 [SMILES: CCCCCCCCC(=O)N(CCCN(C)C)C(CCCCCCCCOC(=O)C(CCCCCC)CCCCCC)CCCCCCCCOC(=O)C(CCCCCC)CCCCCC] | D |
| II-22 | 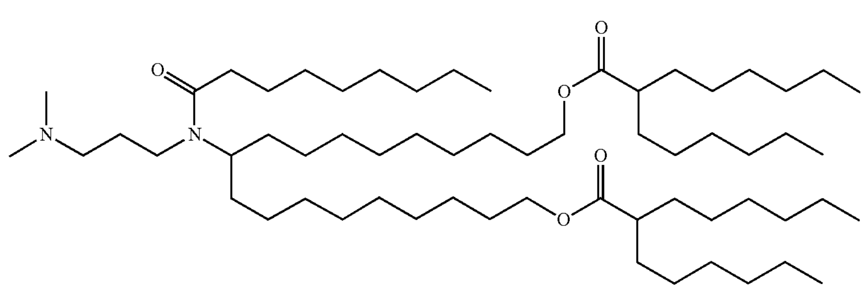 [SMILES: CCCCCCCCC(=O)N(CCCN(C)C)C(CCCCCCCCCOC(=O)C(CCCCCC)CCCCCC)CCCCCCCCCOC(=O)C(CCCCCC)CCCCCC] | D |

TABLE 2-continued

Representative Lipids of Formula (II)

| No. | Structure | Prep. Method |
|---|---|---|
| II-23 | 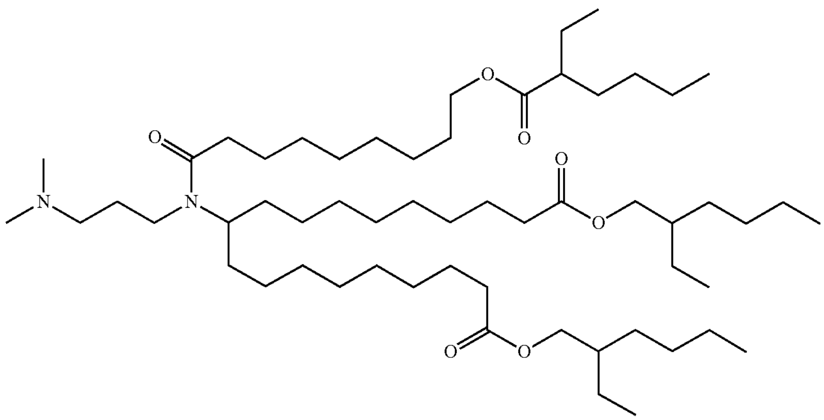 [SMILES: CCCCC(CC)COC(=O)CCCCCCCCC(CCCCCCCCC(=O)OCC(CC)CCCC)N(CCCN(C)C)C(=O)CCCCCCCCOC(=O)C(CC)CCCC] | D |
| II-24 | 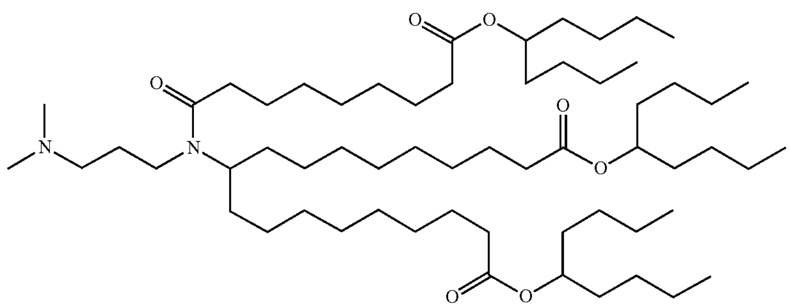 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] | D |
| II-25 | 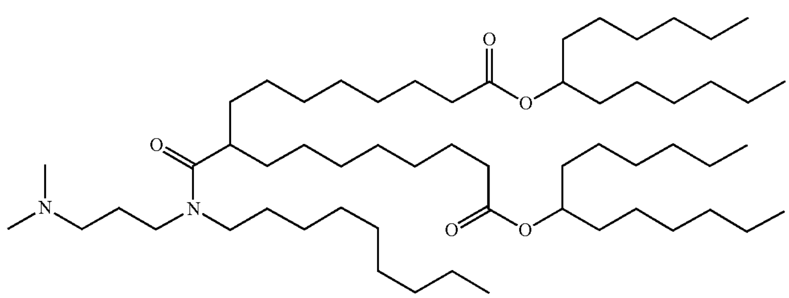 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | E |
| II-26 | 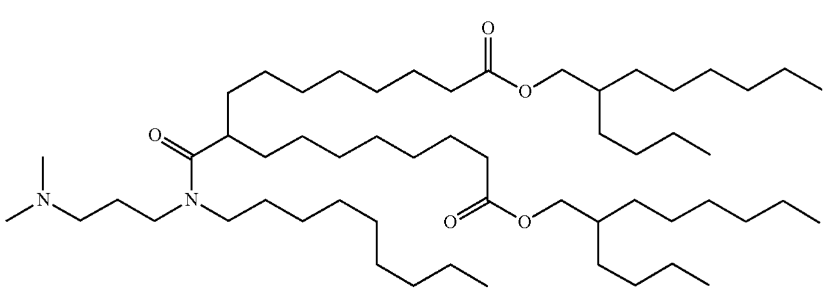 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | E |

TABLE 2-continued

Representative Lipids of Formula (II)

| No. | Structure | Prep. Method |
|---|---|---|
| II-27 | 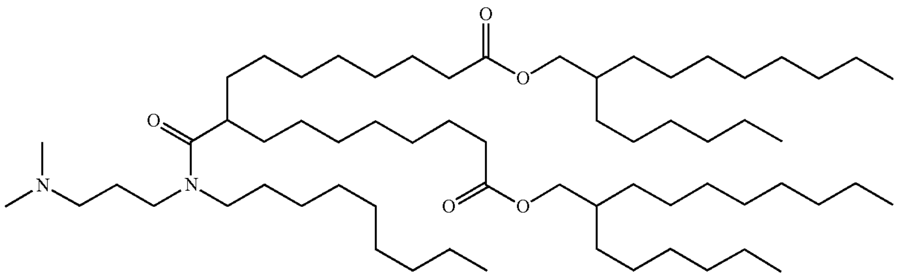 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | E |
| II-28 | 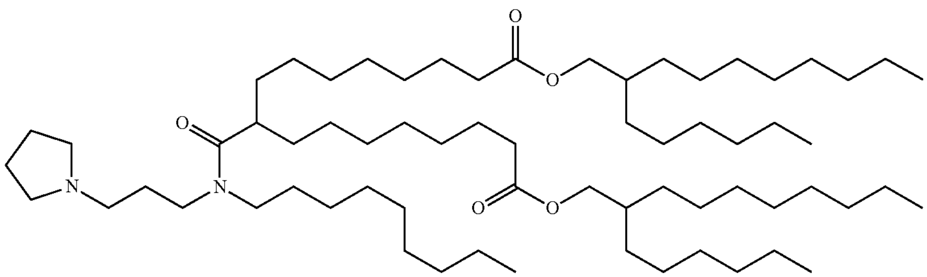 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | E |
| II-29 | 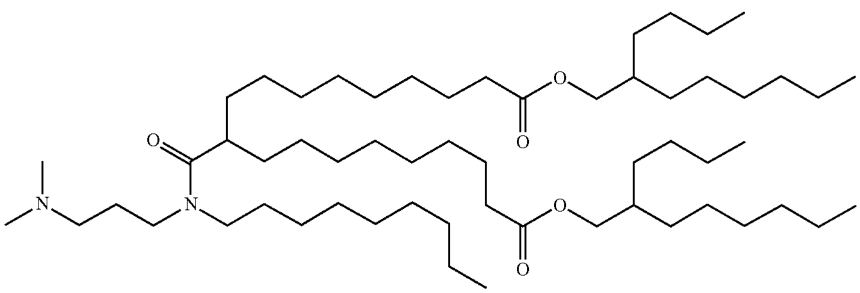 [SMILES: CCCCCCCCCN(CCCN(C)C)C(=O)C(CCCCCCCCC(=O)OCC(CCCC)CCCCCC)CCCCCCCCC(=O)OCC(CCCC)CCCCCC] | E |
| II-30 | 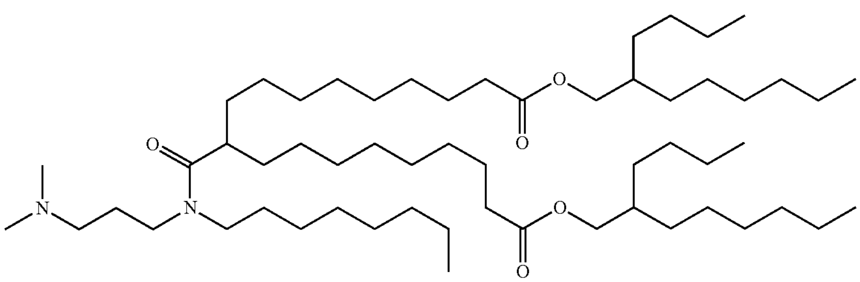 [SMILES: CCCCCCCCN(CCCN(C)C)C(=O)C(CCCCCCCCC(=O)OCC(CCCC)CCCCCC)CCCCCCCCC(=O)OCC(CCCC)CCCCCC] | E |
| II-31 | 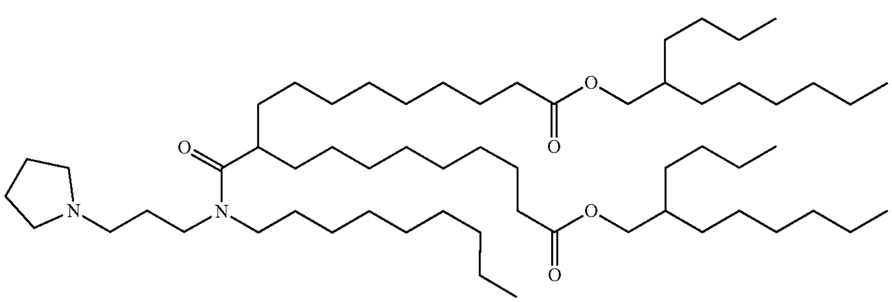 [SMILES: CCCCCCCCCN(CCCN1CCCC1)C(=O)C(CCCCCCCCC(=O)OCC(CCCC)CCCCCC)CCCCCCCCC(=O)OCC(CCCC)CCCCCC] | E |

TABLE 2-continued

Representative Lipids of Formula (II)

| No. | Structure | Prep. Method |
|---|---|---|
| II-32 | 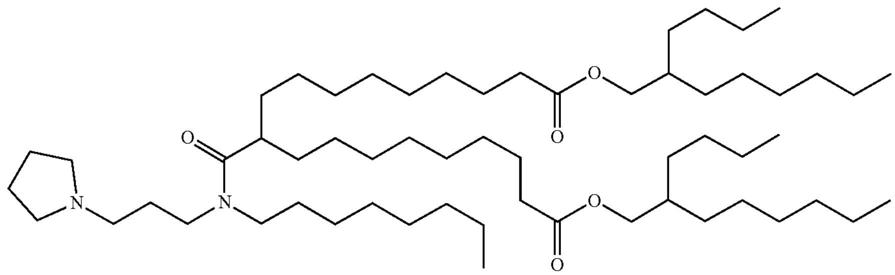 [SMILES: CCCCCCCCN(CCCN1CCCC1)C(=O)C(CCCCCCCCC(=O)OCC(CCCC)CCCCCC)CCCCCCCCC(=O)OCC(CCCC)CCCCCC] | E |
| II-33 | 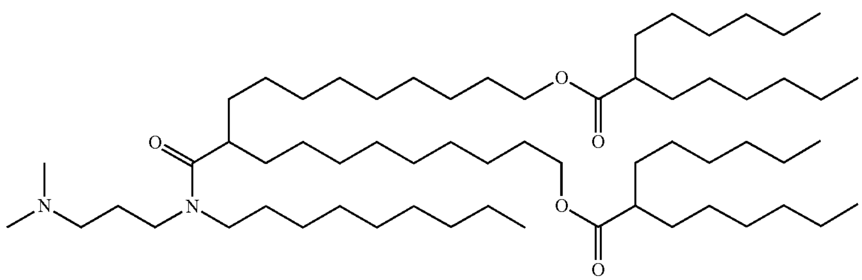 [SMILES: CCCCCCCCCN(CCCN(C)C)C(=O)C(CCCCCCCCCOC(=O)C(CCCCCC)CCCCCC)CCCCCCCCCOC(=O)C(CCCCCC)CCCCCC] | E |
| II-34 | 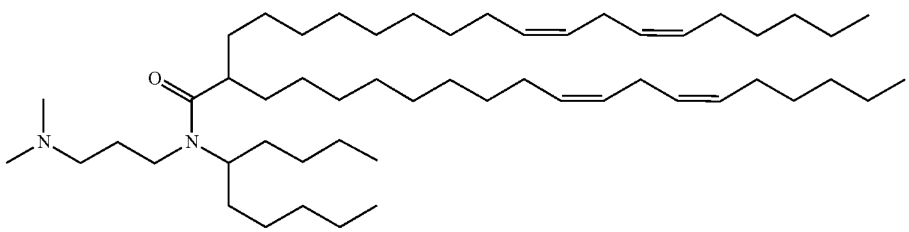 [SMILES: CCCCC/C=C\C/C=C\CCCCCCCCC(CCCCCCCC/C=C\C/C=C\CCCCC)C(=O)N(CCCN(C)C)C(CCCC)CCCCC] | E |

In some embodiments, the LNPs comprise a lipid of Formula (II), a nucleoside-modified RNA and one or more excipient selected from neutral lipids, steroids and pegylated lipids. In some embodiments, the lipid of Formula (II) is compound II-9. In some embodiments, the lipid of Formula (II) is compound II-10. In some embodiments, the lipid of Formula (II) is compound II-11. In some embodiments, the lipid of Formula (II) is compound II-12. In some embodiments, the lipid of Formula (II) is compound II-32.

In some other embodiments, the cationic lipid component of the LNPs has the structure of Formula (III):

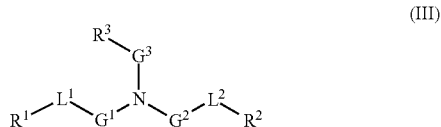

(III)

or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O) NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O) NR$^a$—, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, OR$^5$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following structures (IIIA) or (IIIB):

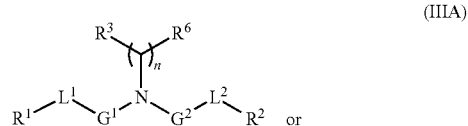

(IIIA)

-continued

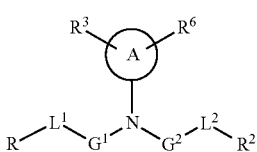
(IIIB)

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

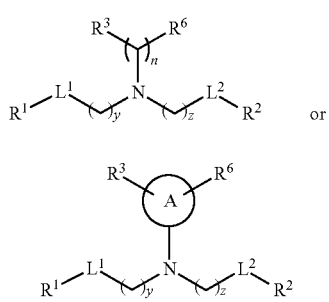

(IIIC)

or (IIID)

wherein y and z are each independently integers ranging from 1 to 12.

In any of the foregoing embodiments of Formula (III), one of $L^1$ or $L^2$ is —O(C=O)—. For example, in some embodiments each of $L^1$ and $L^2$ are —O(C=O)—. In some different embodiments of any of the foregoing, $L^1$ and $L^2$ are each independently —(C=O)O— or —O(C=O)—. For example, in some embodiments each of $L^1$ and $L^2$ is —(C=O)O—.

In some different embodiments of Formula (III), the lipid has one of the following structures (IIIE) or (IIIF):

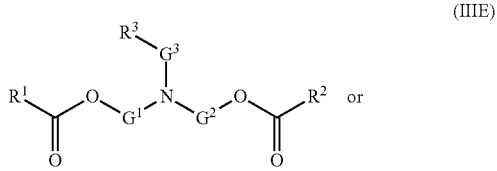

(IIIE)

or

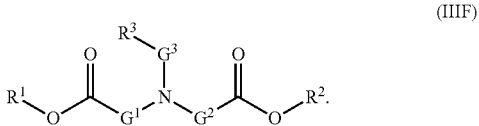

(IIIF)

In some of the foregoing embodiments of Formula (III), the lipid has one of the following structures (IIIG), (IIIH), (IIII), or (IIIJ):

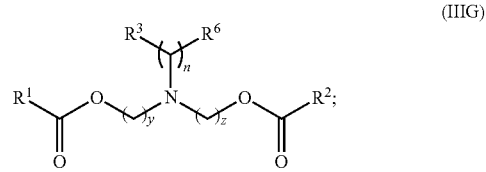
(IIIG)

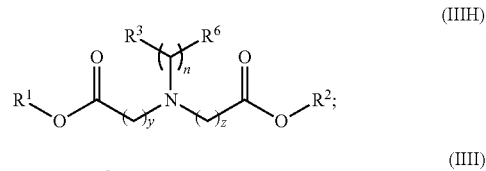
(IIIH)

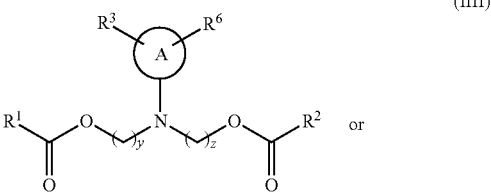
(IIII)

or

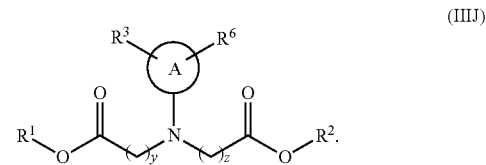
(IIIJ)

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, $G^3$ is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

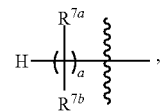

wherein:

R$^{7a}$ and R$^{7b}$ are, at each occurrence, independently H or C$_1$-C$_{12}$ alkyl; and a is an integer from 2 to 12, wherein R$^{7a}$, R$^{7b}$ and a are each selected such that R$^1$ and R$^2$ each independently comprise from 6 to 20 carbon atoms. For example, in some embodiments a is an integer ranging from 5 to 9 or from 8 to 12.

In some of the foregoing embodiments of Formula (III), at least one occurrence of R$^{7a}$ is H. For example, in some embodiments, R$^{7a}$ is H at each occurrence. In other different embodiments of the foregoing, at least one occurrence of R$^7$ is C$_1$-C$_8$ alkyl. For example, in some embodiments, C$_1$-C$_8$ alkyl is methyl, ethyl, n-propyl, iso-propyl, n-butyl, iso-butyl, tert-butyl, n-hexyl or n-octyl.

In different embodiments of Formula (III), R$^1$ or R$^2$, or both, has one of the following structures:

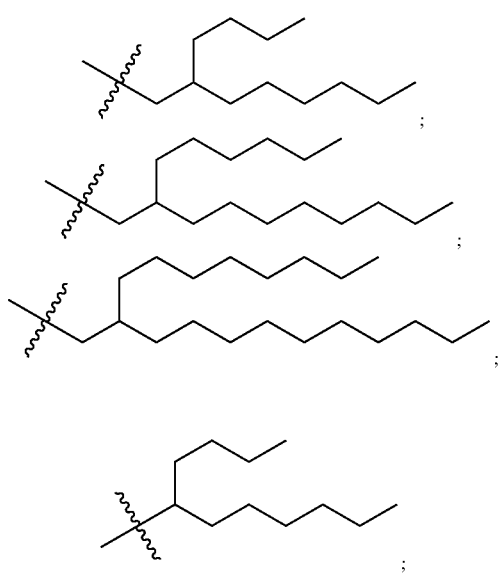

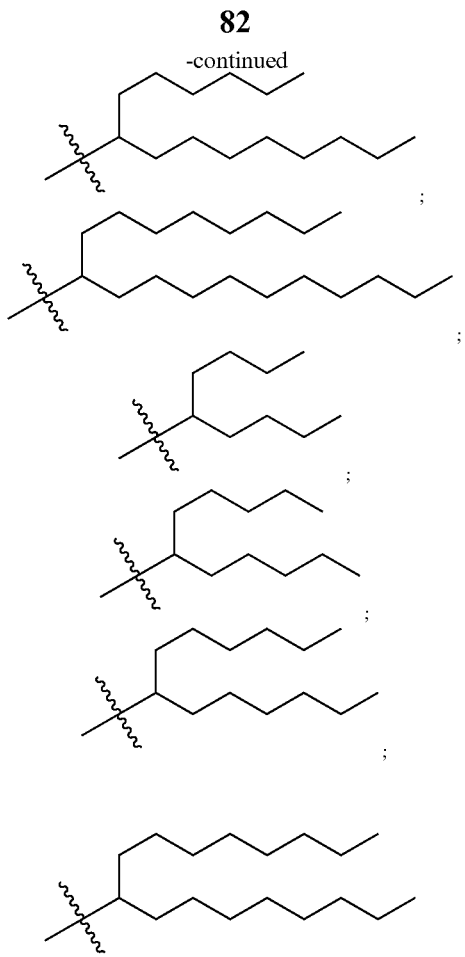

In some of the foregoing embodiments of Formula (III), R$^3$ is OH, CN, —C(=O)OR$^4$, —OC(=O)R$^4$ or —NHC(=O)R$^4$. In some embodiments, R$^4$ is methyl or ethyl.

In various different embodiments, the cationic lipid of Formula (III) has one of the structures set forth in Table 3 below.

TABLE 3

Representative Compounds of Formula (III)

| No. | Structure | Prep. Method |
|---|---|---|
| III-1 | 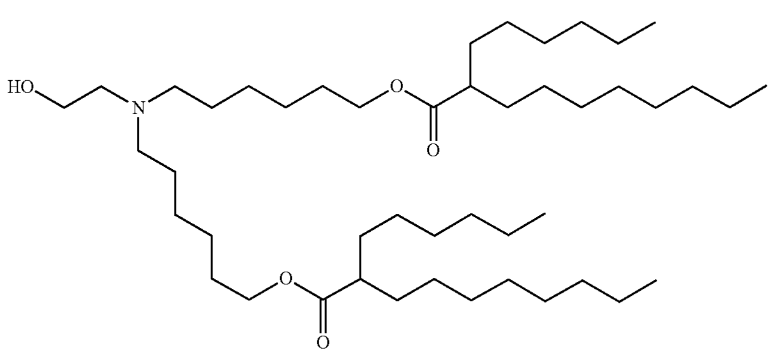 [SMILES: CCCCCCCCC(CCCCCC)C(=O)OCCCCCCN(CCO)CCCCCCOC(=O)C(CCCCCC)CCCCCCCC] | F |

TABLE 3-continued

Representative Compounds of Formula (III)

| No. | Structure | Prep. Method |
|---|---|---|
| III-2 | 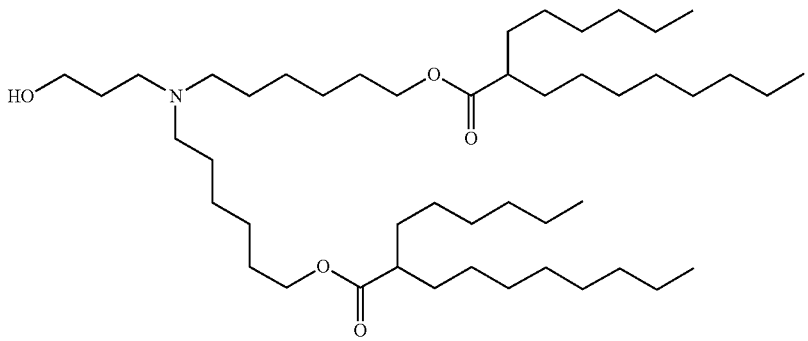 [SMILES: CCCCCCCCC(CCCCCC)C(=O)OCCCCCCN(CCCO)CCCCCCOC(=O)C(CCCCCC)CCCCCCCC] | F |
| III-3 | 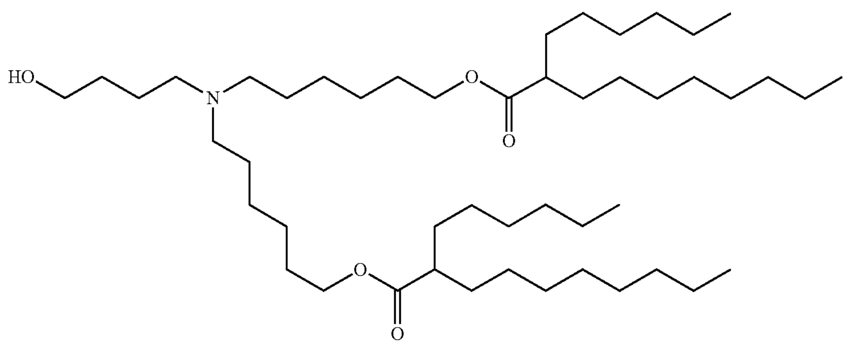 [SMILES: CCCCCCCCC(CCCCCC)C(=O)OCCCCCCN(CCCCO)CCCCCCOC(=O)C(CCCCCC)CCCCCCCC] | F |
| III-4 | 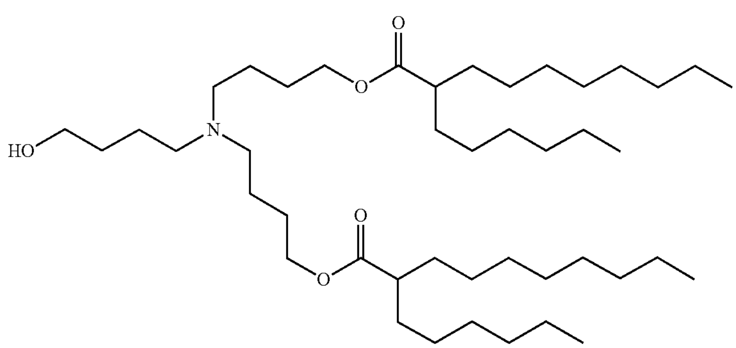 [SMILES: CCCCCCCCC(CCCCCC)C(=O)OCCCCN(CCCCO)CCCCOC(=O)C(CCCCCC)CCCCCCCC] | F |
| III-5 | 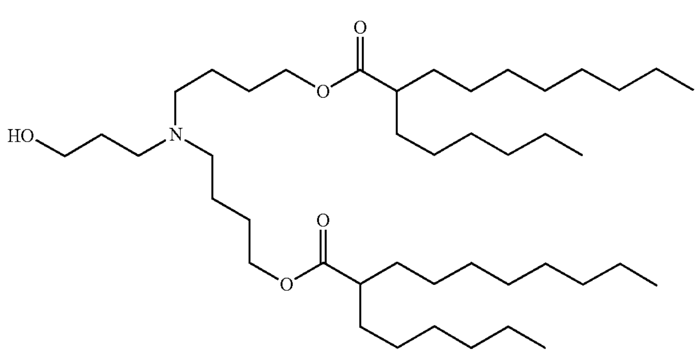 [SMILES: CCCCCCCCC(CCCCCC)C(=O)OCCCCN(CCCO)CCCCOC(=O)C(CCCCCC)CCCCCCCC] | F |

TABLE 3-continued

Representative Compounds of Formula (III)

| No. | Structure | Prep. Method |
|---|---|---|
| III-6 | 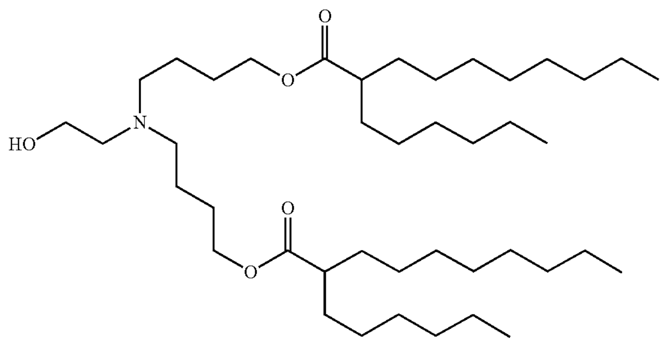 [SMILES: CCCCCCCCC(CCCCCC)C(=O)OCCCCN(CCO)CCCCOC(=O)C(CCCCCC)CCCCCCCC] | F |
| III-7 | 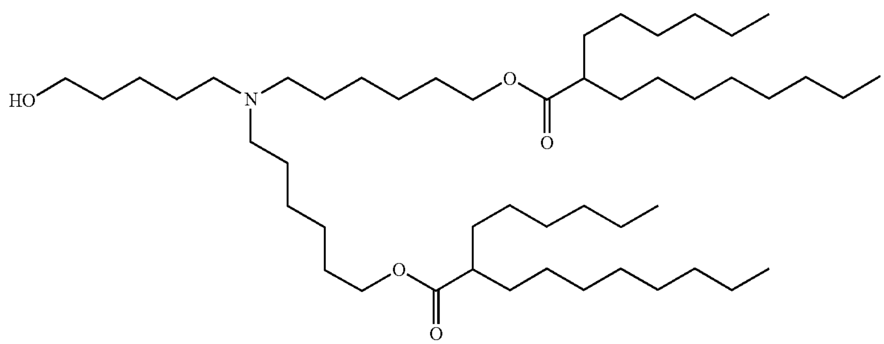 [SMILES: CCCCCCCCC(CCCCCC)C(=O)OCCCCCCN(CCCCCO)CCCCCCOC(=O)C(CCCCCC)CCCCCCCC] | F |
| III-8 | 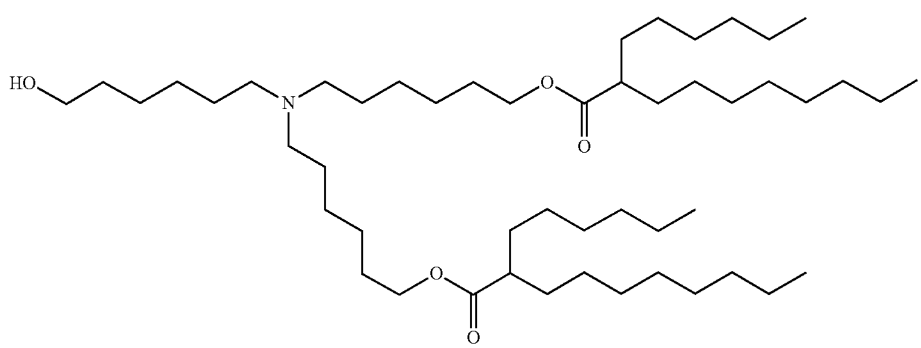 [SMILES: CCCCCCCCC(CCCCCC)C(=O)OCCCCCCN(CCCCCCO)CCCCCCOC(=O)C(CCCCCC)CCCCCCCC] | F |
| III-9 | 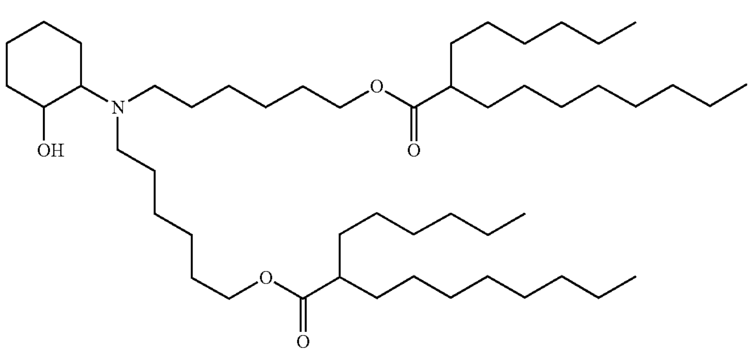 [SMILES: CCCCCCCCC(CCCCCC)C(=O)OCCCCCCN(CCCCCCOC(=O)C(CCCCCC)CCCCCCCC)C1CCCCC1O] | F |

TABLE 3-continued
Representative Compounds of Formula (III)
| No. | Structure | Prep. Method |
|---|---|---|
| III-10 | 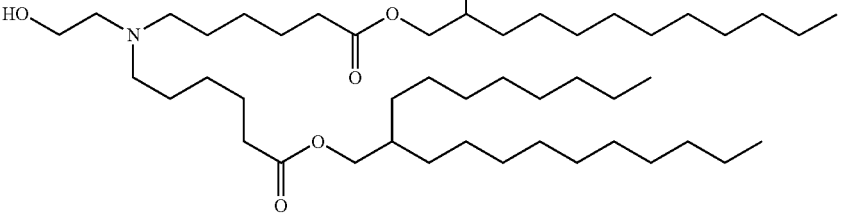 | F |
| III-11 | 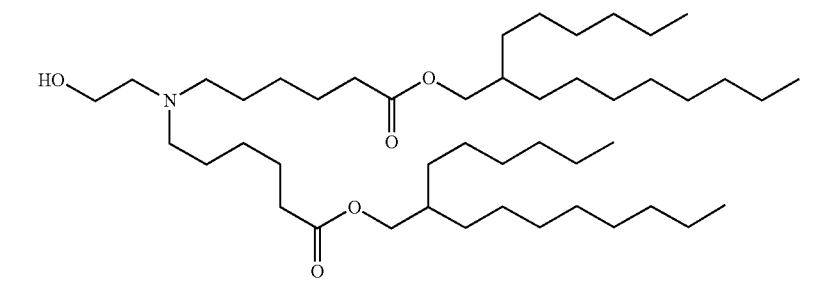 [SMILES: CCCCCCCCC(CCCCCC)COC(=O)CCCCCN(CCO)CCCCCC(=O)OCC(CCCCCC)CCCCCCCC] | F |
| III-12 | 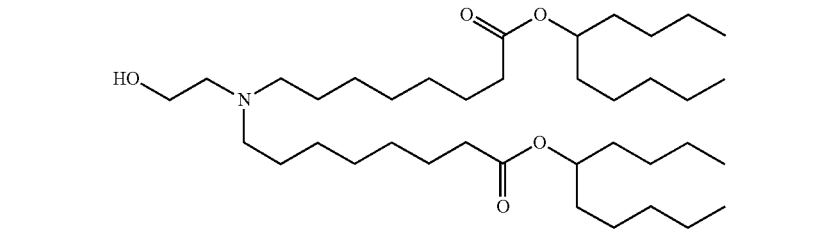 [SMILES: CCCCCC(CCCC)OC(=O)CCCCCCCN(CCO)CCCCCCCC(=O)OC(CCCC)CCCCC] | F |
| III-13 | 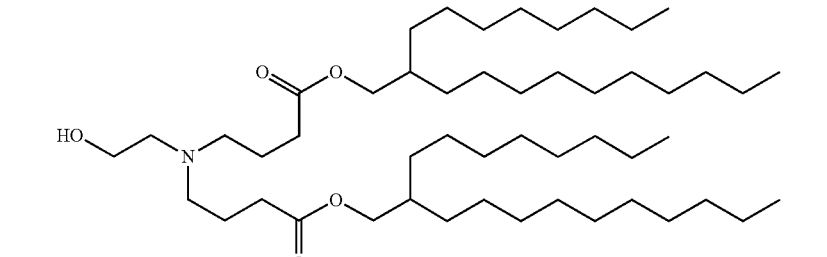 | F |
| III-14 | 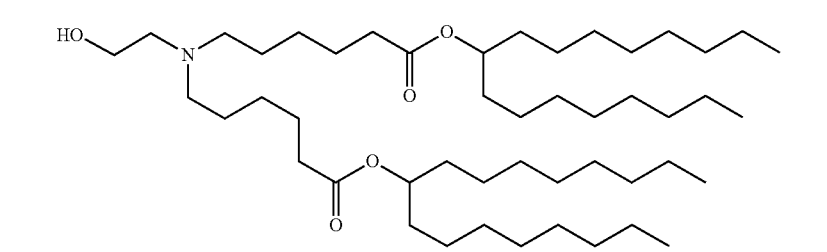 [SMILES: CCCCCCCCC(CCCCCCCC)OC(=O)CCCCCN(CCO)CCCCCC(=O)OC(CCCCCCCC)CCCCCCCC] | F |

TABLE 3-continued

Representative Compounds of Formula (III)

| No. | Structure | Prep. Method |
|---|---|---|
| III-15 | 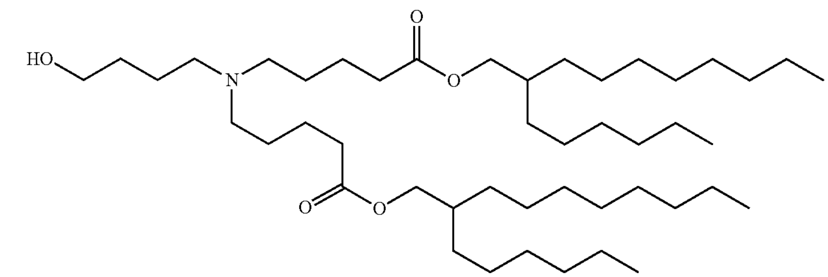 [SMILES: CCCCCCCCC(CCCCCC)COC(=O)CCCCN(CCCCO)CCCCC(=O)OCC(CCCCCC)CCCCCCCC] | F |
| III-16 | 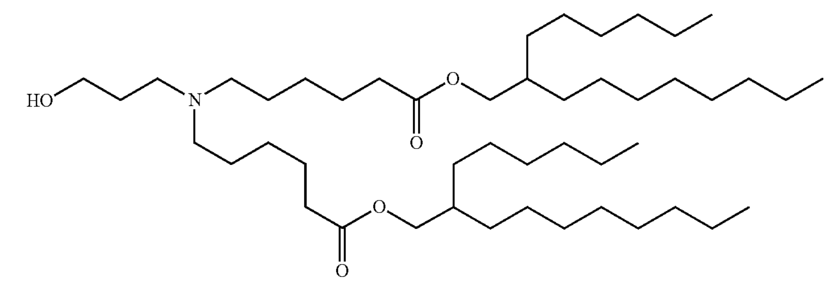 [SMILES: CCCCCCCCC(CCCCCC)COC(=O)CCCCCN(CCCO)CCCCCC(=O)OCC(CCCCCC)CCCCCCCC] | F |
| III-17 | 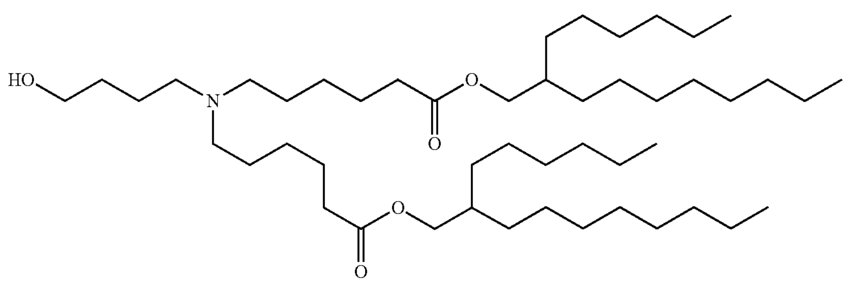 [SMILES: CCCCCCCCC(CCCCCC)COC(=O)CCCCCN(CCCCO)CCCCCC(=O)OCC(CCCCCC)CCCCCCCC] | F |
| III-18 | 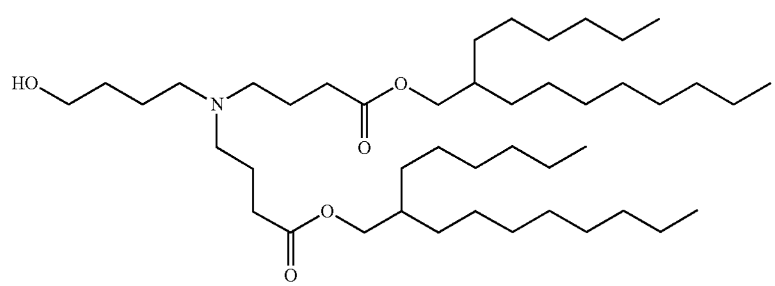 [SMILES: CCCCCCCCC(CCCCCC)COC(=O)CCCN(CCCCO)CCCC(=O)OCC(CCCCCC)CCCCCCCC] | F |
| III-19 | 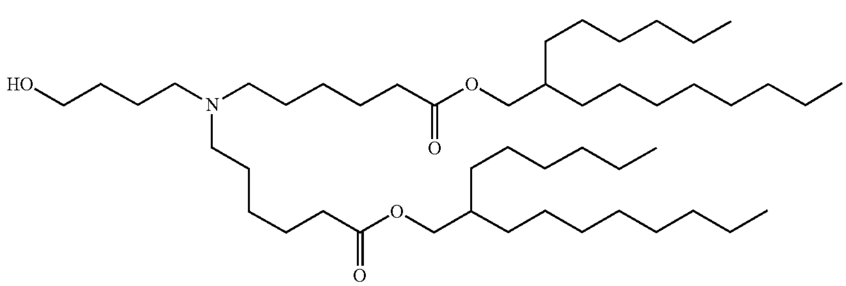 [SMILES: CCCCCCCCC(CCCCCC)COC(=O)CCCCCN(CCCCO)CCCCCC(=O)OCC(CCCCCC)CCCCCCCC] | F |

TABLE 3-continued

Representative Compounds of Formula (III)

| No. | Structure | Prep. Method |
|---|---|---|
| III-20 | 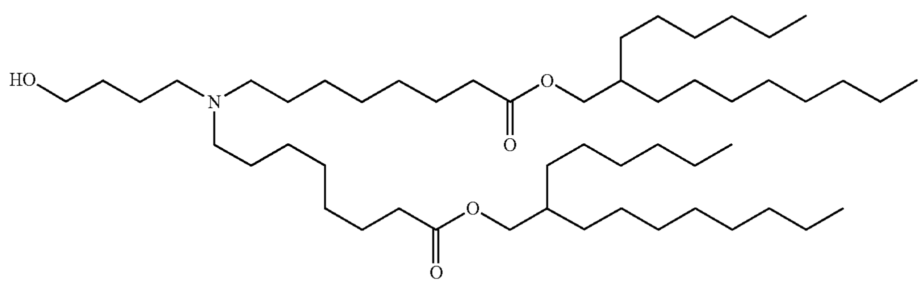 [SMILES: CCCCCCCCC(CCCCCC)COC(=O)CCCCCCCN(CCCCO)CCCCCCCC(=O)OCC(CCCCCC)CCCCCCCC] | F |
| III-21 | 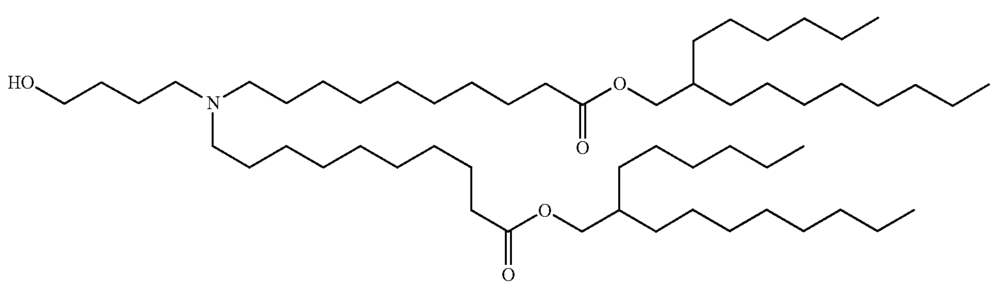 [SMILES: CCCCCCCCC(CCCCCC)COC(=O)CCCCCCCCCN(CCCCO)CCCCCCCCCC(=O)OCC(CCCCCC)CCCCCCCC] | F |
| III-22 | 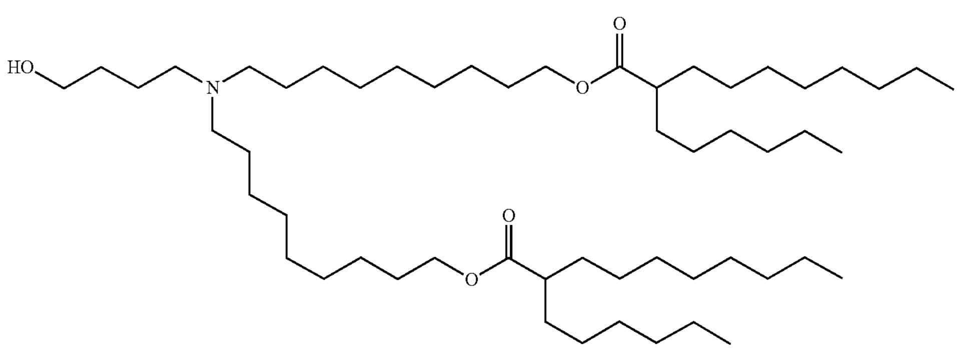 [SMILES: CCCCCCCCC(CCCCCC)C(=O)OCCCCCCCCCN(CCCCO)CCCCCCCCCOC(=O)C(CCCCCC)CCCCCCCC] | F |
| III-23 | 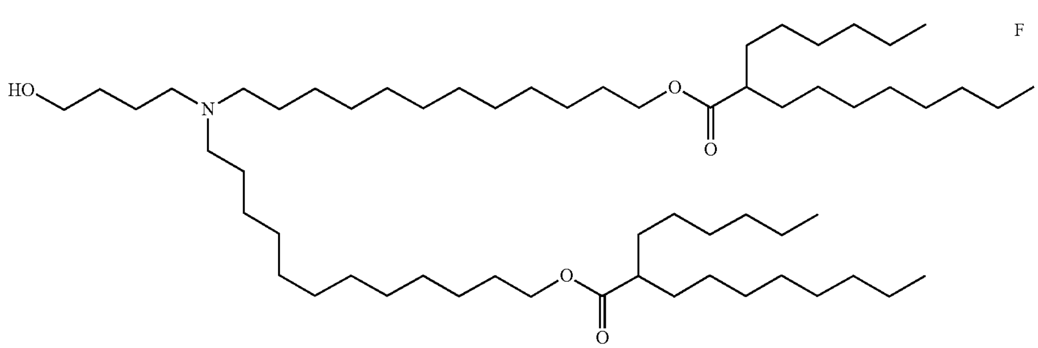 [SMILES: CCCCCCCCC(CCCCCC)C(=O)OCCCCCCCCCCCCN(CCCCO)CCCCCCCCCCCCOC(=O)C(CCCCCC)CCCCCCCC] | F |

TABLE 3-continued

Representative Compounds of Formula (III)

| No. | Structure | Prep. Method |
|---|---|---|
| III-24 | 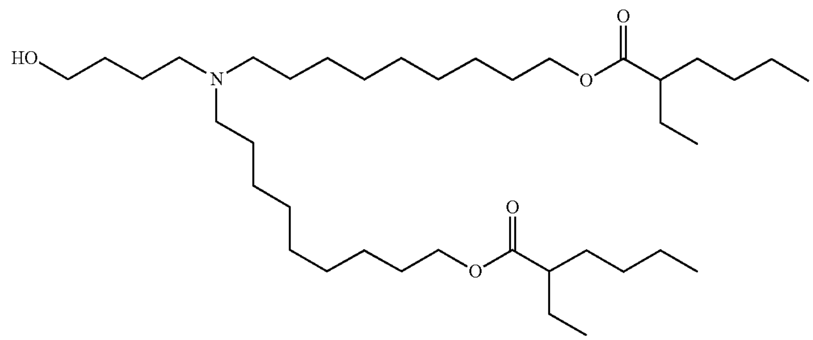 [SMILES: CCCCC(CC)C(=O)OCCCCCCCCCN(CCCCO)CCCCCCCCCOC(=O)C(CC)CCCC] | F |
| III-25 | 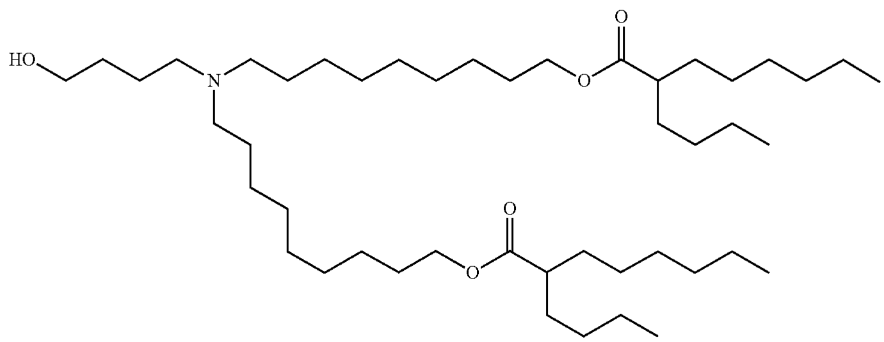 [SMILES: CCCCCCC(CCCC)C(=O)OCCCCCCCCCN(CCCCO)CCCCCCCCCOC(=O)C(CCCC)CCCCCC] | F |
| III-26 | 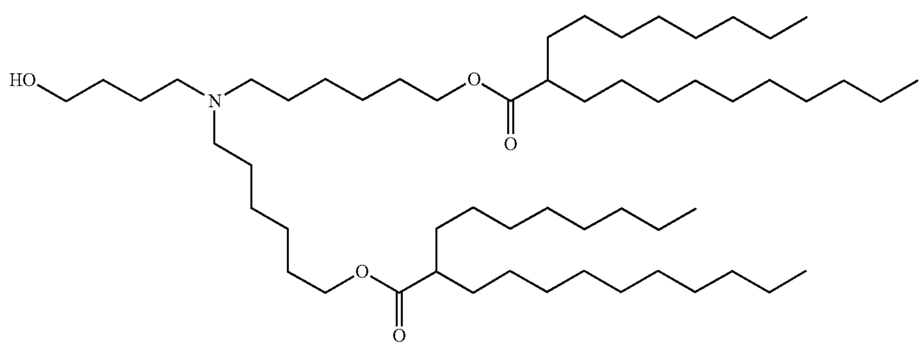 [SMILES: CCCCCCCCCCC(CCCCCCCC)C(=O)OCCCCCCN(CCCCO)CCCCCCOC(=O)C(CCCCCCCC)CCCCCCCCCC] | F |
| III-27 | 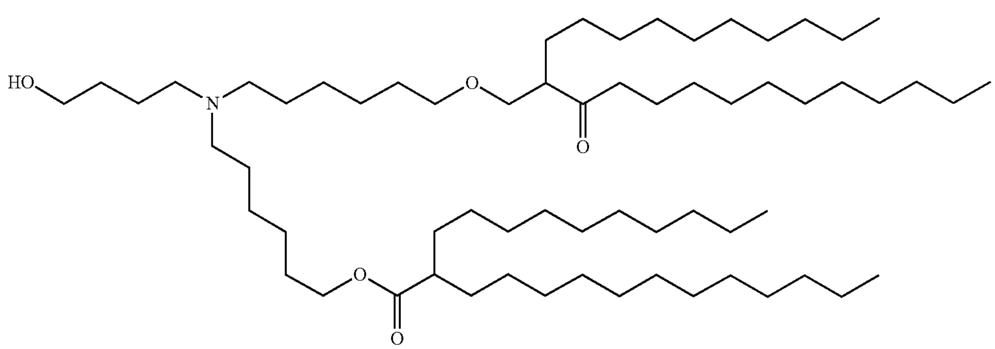 [SMILES: CCCCCCCCCCCCC(CCCCCCCCCC)C(=O)OCCCCCCN(CCCCO)CCCCCCOCC(CCCCCCCCCC)C(=O)CCCCCCCCCCC] | F |

TABLE 3-continued

Representative Compounds of Formula (III)

| No. | Structure | Prep. Method |
|---|---|---|
| III-28 | 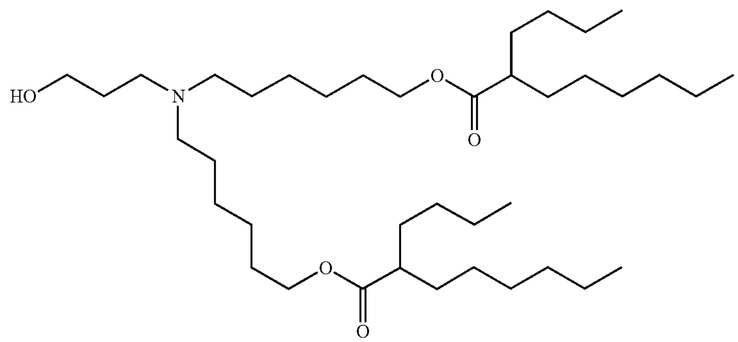 [SMILES: CCCCCCC(CCCC)C(=O)OCCCCCCN(CCCO)CCCCCCOC(=O)C(CCCC)CCCCCC] | F |
| III-29 | 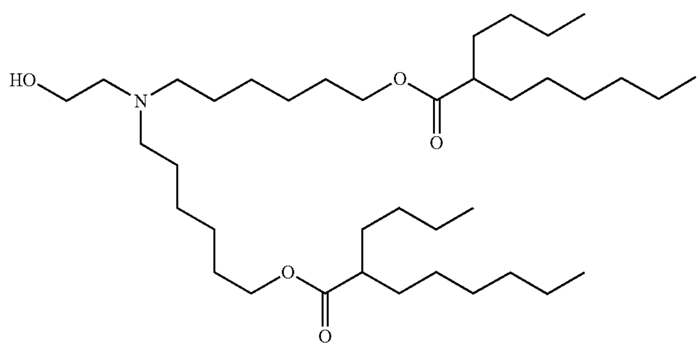 [SMILES: CCCCCCC(CCCC)C(=O)OCCCCCCN(CCO)CCCCCCOC(=O)C(CCCC)CCCCCC] | F |
| III-30 | 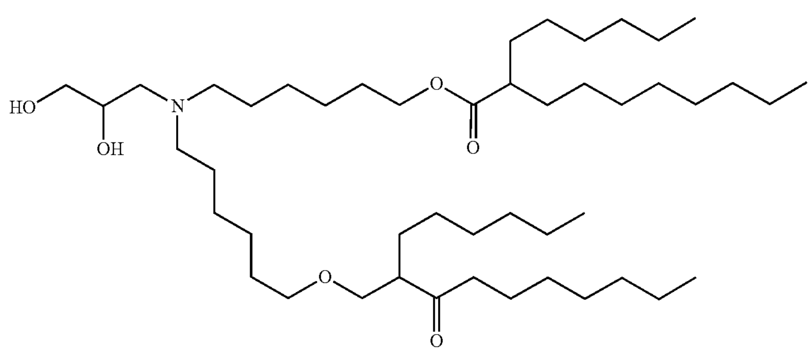 [SMILES: CCCCCCCCC(CCCCCC)C(=O)OCCCCCCN(CCCCCCOCC(CCCCCC)C(=O)CCCCCCC)CC(O)CO] | F |
| III-31 | 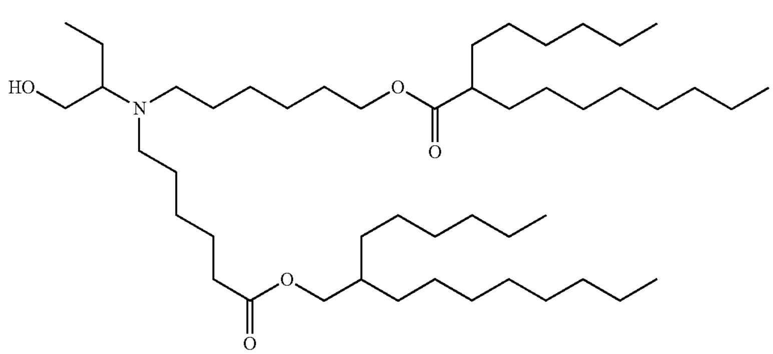 [SMILES: CCCCCCCCC(CCCCCC)COC(=O)CCCCCN(CCCCCCOC(=O)C(CCCCCC)CCCCCCCC)C(CC)CO] | F |

TABLE 3-continued

Representative Compounds of Formula (III)

| No. | Structure | Prep. Method |
|---|---|---|
| III-32 | 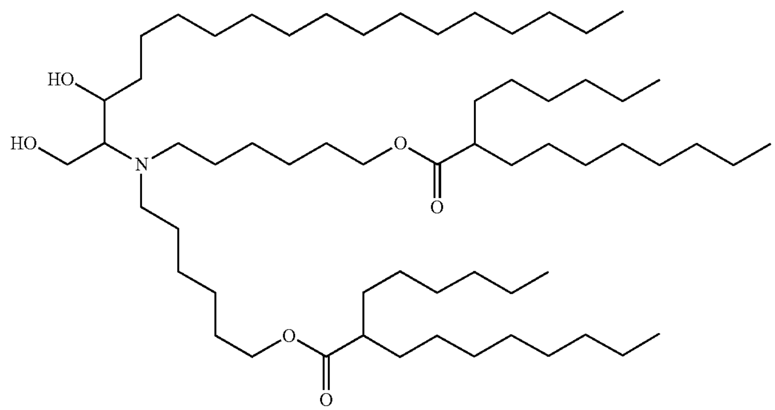 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | F |
| III-33 | 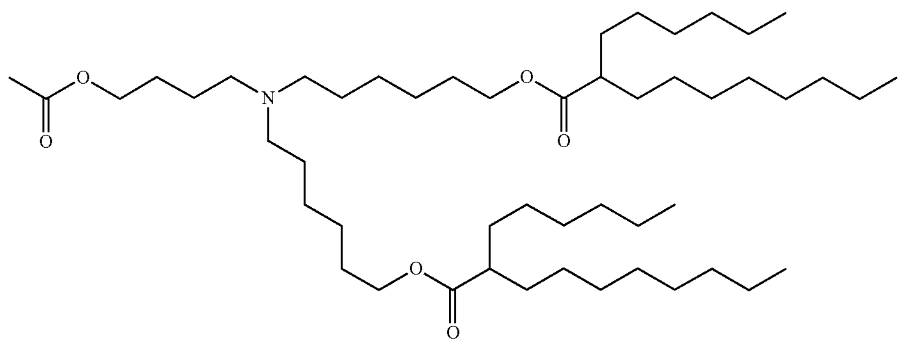 [SMILES: CCCCCCCCC(CCCCCC)C(=O)OCCCCCCN(CCCCCCOC(=O)C(CCCCCC)CCCCCCCC)CCCCOC(C)=O] | F |
| III-34 | 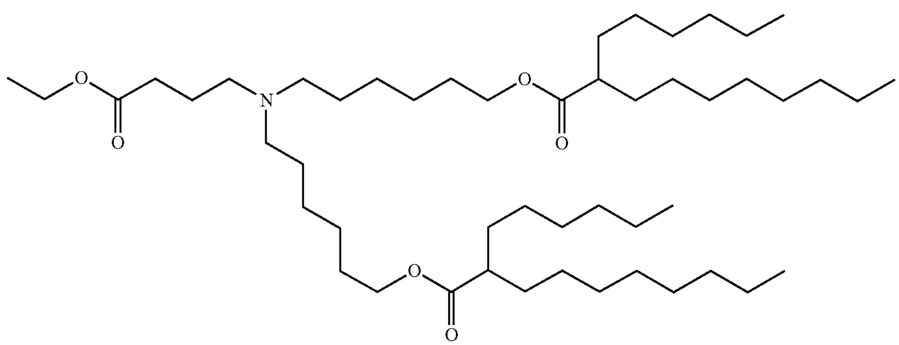 [SMILES: CCCCCCCCC(CCCCCC)C(=O)OCCCCCCN(CCCCCCOC(=O)C(CCCCCC)CCCCCCCC)CCCC(=O)OCC] | F |
| III-35 | 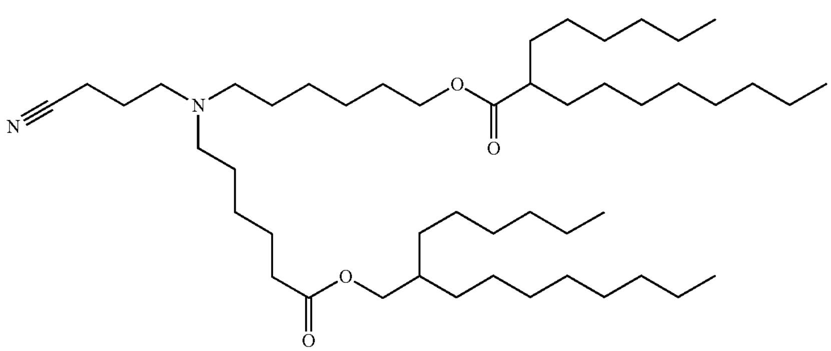 [SMILES: CCCCCCCCC(CCCCCC)COC(=O)CCCCCN(CCCC#N)CCCCCCOC(=O)C(CCCCCC)CCCCCCCC] | F |

TABLE 3-continued

Representative Compounds of Formula (III)

| No. | Structure | Prep. Method |
|---|---|---|
| III-36 | 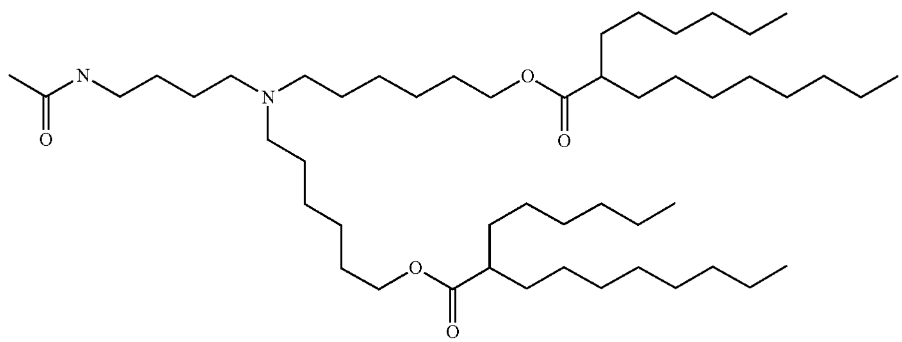 | F |

In some embodiments, the LNPs comprise a lipid of Formula (III), a nucleoside-modified RNA and one or more excipient selected from neutral lipids, steroids and pegylated lipids. In some embodiments, the lipid of Formula (III) is compound III-3. In some embodiments, the lipid of Formula (III) is compound III-7.

In certain embodiments, the cationic lipid is present in the LNP in an amount from about 30 to about 95 mole percent. In one embodiment, the cationic lipid is present in the LNP in an amount from about 30 to about 70 mole percent. In one embodiment, the cationic lipid is present in the LNP in an amount from about 40 to about 60 mole percent. In one embodiment, the cationic lipid is present in the LNP in an amount of about 50 mole percent. In one embodiment, the LNP comprises only cationic lipids.

In certain embodiments, the LNP comprises one or more additional lipids which stabilize the formation of particles during their formation.

Suitable stabilizing lipids include neutral lipids and anionic lipids.

The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid (e.g., lipid of Formula (I)) to the neutral lipid ranges from about 2:1 to about 8:1.

In various embodiments, the LNPs further comprise a steroid or steroid analogue. A "steroid" is a compound comprising the following carbon skeleton:

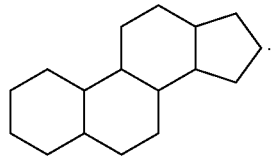 [SMILES: C1CCC2C(C1)CCC1C3CCCC3CCC21]

In certain embodiments, the steroid or steroid analogue is cholesterol. In some of these embodiments, the molar ratio of the cationic lipid (e.g., lipid of Formula (I)) to cholesterol ranges from about 2:1 to 1:1.

The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleoylphosphatidylglycerol (POPG), and other anionic modifying groups joined to neutral lipids.

In certain embodiments, the LNP comprises glycolipids (e.g., monosialoganglioside $GM_1$). In certain embodiments, the LNP comprises a sterol, such as cholesterol.

In some embodiments, the LNPs comprise a polymer conjugated lipid. The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-s-DMG) and the like.

In certain embodiments, the LNP comprises an additional, stabilizing-lipid which is a polyethylene glycol-lipid (pegylated lipid). Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG). In other embodiments, the LNPs comprise a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy (polyethoxy)ethyl-N-(2,3-di(tetradecanoxy)propyl)carbamate or 2,3-di(tetradecanoxy)propyl-N-(ω-methoxy(polyethoxy)ethyl)carbamate. In various embodiments, the molar ratio of the cationic lipid to the pegylated lipid ranges from about 100:1 to about 25:1.

In some embodiments, the LNPs comprise a pegylated lipid having the following structure (IV):

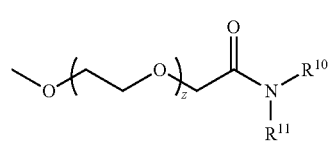

(IV)

or a pharmaceutically acceptable salt, tautomer or stereoisomer thereof, wherein:
  $R^{10}$ and $R^{11}$ are each independently a straight or branched, saturated or unsaturated alkyl chain containing from 10 to 30 carbon atoms, wherein the alkyl chain is optionally interrupted by one or more ester bonds; and
  z has mean value ranging from 30 to 60.

In some of the foregoing embodiments of the pegylated lipid (IV), $R^{10}$ and $R^{11}$ are not both n-octadecyl when z is 42. In some other embodiments, $R^{10}$ and $R^{11}$ are each independently a straight or branched, saturated or unsaturated alkyl chain containing from 10 to 18 carbon atoms. In some embodiments, $R^{10}$ and $R^{11}$ are each independently a straight or branched, saturated or unsaturated alkyl chain containing from 12 to 16 carbon atoms. In some embodiments, $R^{10}$ and $R^{11}$ are each independently a straight or branched, saturated or unsaturated alkyl chain containing 12 carbon atoms. In some embodiments, $R^{10}$ and $R^{11}$ are each independently a straight or branched, saturated or unsaturated alkyl chain containing 14 carbon atoms. In other embodiments, $R^{10}$ and $R^{11}$ are each independently a straight or branched, saturated or unsaturated alkyl chain containing 16 carbon atoms. In still more embodiments, $R^{10}$ and $R^{11}$ are each independently a straight or branched, saturated or unsaturated alkyl chain containing 18 carbon atoms. In still other embodiments, $R^{10}$ is a straight or branched, saturated or unsaturated alkyl chain containing 12 carbon atoms and $R^{11}$ is a straight or branched, saturated or unsaturated alkyl chain containing 14 carbon atoms.

In various embodiments, z spans a range that is selected such that the PEG portion of (II) has an average molecular weight of about 400 to about 6000 g/mol. In some embodiments, the average z is about 45.

In other embodiments, the pegylated lipid has one of the following structures:

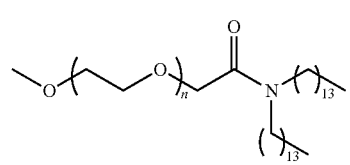

(IVa)

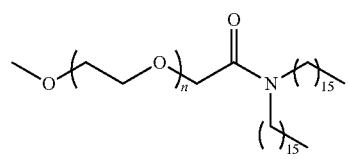

(IVb)

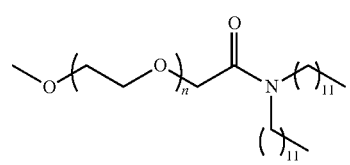

(IVc)

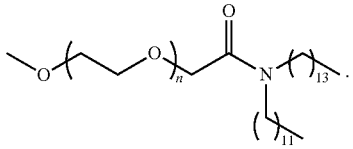

(IVd)

wherein n is an integer selected such that the average molecular weight of the pegylated lipid is about 2500 g/mol.

In certain embodiments, the additional lipid is present in the LNP in an amount from about 1 to about 10 mole percent. In one embodiment, the additional lipid is present in the LNP in an amount from about 1 to about 5 mole percent. In one embodiment, the additional lipid is present in the LNP in about 1 mole percent or about 1.5 mole percent.

In some embodiments, the LNPs comprise a lipid of Formula (I), a nucleoside-modified RNA, a neutral lipid, a steroid and a pegylated lipid. In some embodiments the lipid of Formula (I) is compound I-6. In different embodiments, the neutral lipid is DSPC. In other embodiments, the steroid is cholesterol. In still different embodiments, the pegylated lipid is compound IVa.

In certain embodiments, the LNP comprises one or more targeting moieties, which are capable of targeting the LNP to a cell or cell population. For example, in one embodiment, the targeting moiety is a ligand, which directs the LNP to a receptor found on a cell surface.

In certain embodiments, the LNP comprises one or more internalization domains. For example, in one embodiment, the LNP comprises one or more domains, which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

Other exemplary LNPs and their manufacture are described in the art, for example in U.S. Patent Application Publication No. US20120276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, each of which are incorporated by reference in their entirety.

The following Reaction Schemes illustrate methods to make lipids of Formula (I), (II) or (III).

GENERAL REACTION SCHEME 1

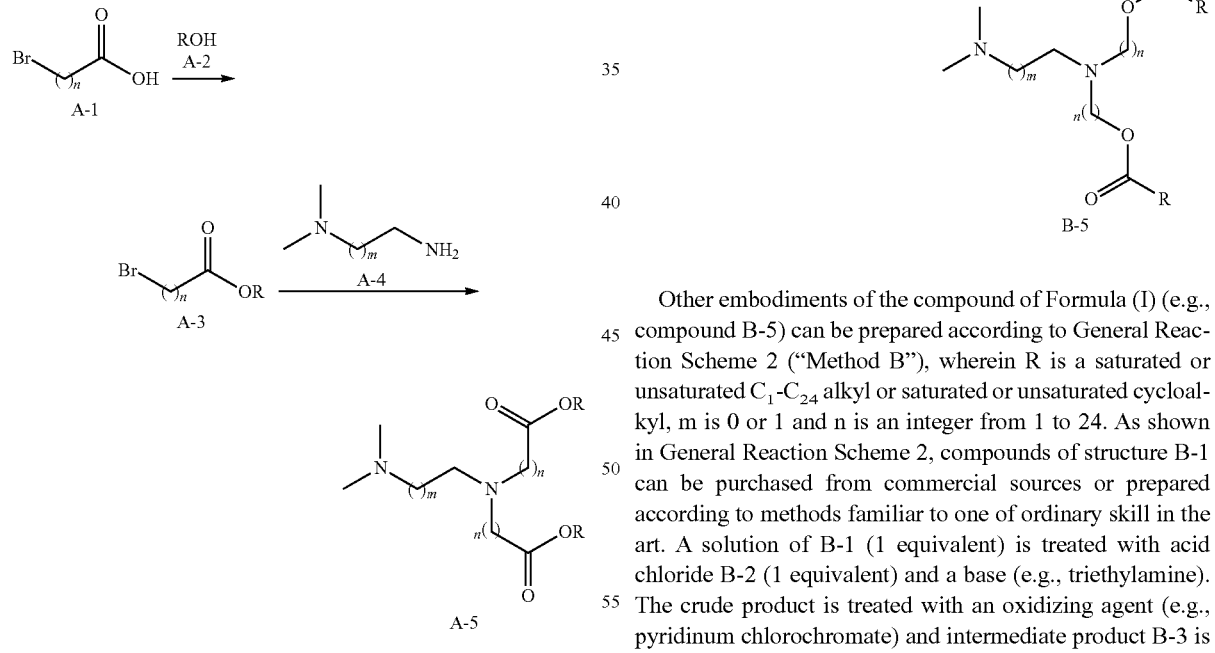

Embodiments of the lipid of Formula (I) (e.g., compound A-5) can be prepared according to General Reaction Scheme 1 ("Method A"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessarily workup and or purification step.

GENERAL REACTION SCHEME 2

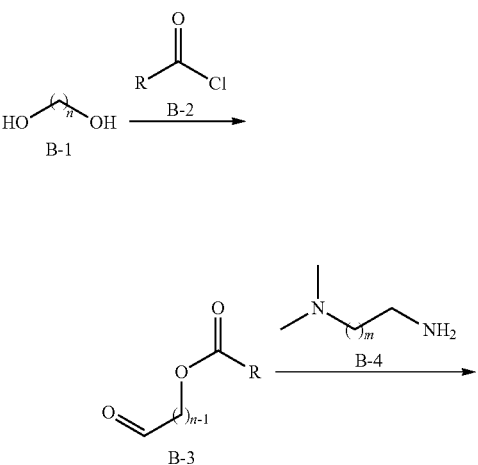

Other embodiments of the compound of Formula (I) (e.g., compound B-5) can be prepared according to General Reaction Scheme 2 ("Method B"), wherein R is a saturated or unsaturated $C_1$-$C_{24}$ alkyl or saturated or unsaturated cycloalkyl, m is 0 or 1 and n is an integer from 1 to 24. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinum chlorochromate) and intermediate product B-3 is recovered. A solution of crude B-3, an acid (e.g., acetic acid), and N,N-dimethylaminoamine B-4 is then treated with a reducing agent (e.g., sodium triacetoxyborohydride) to obtain B-5 after any necessary work up and/or purification.

It should be noted that although starting materials A-1 and B-1 are depicted above as including only saturated methylene carbons, starting materials which include carbon-carbon double bonds may also be employed for preparation of compounds which include carbon-carbon double bonds.

GENERAL REACTION SCHEME 3

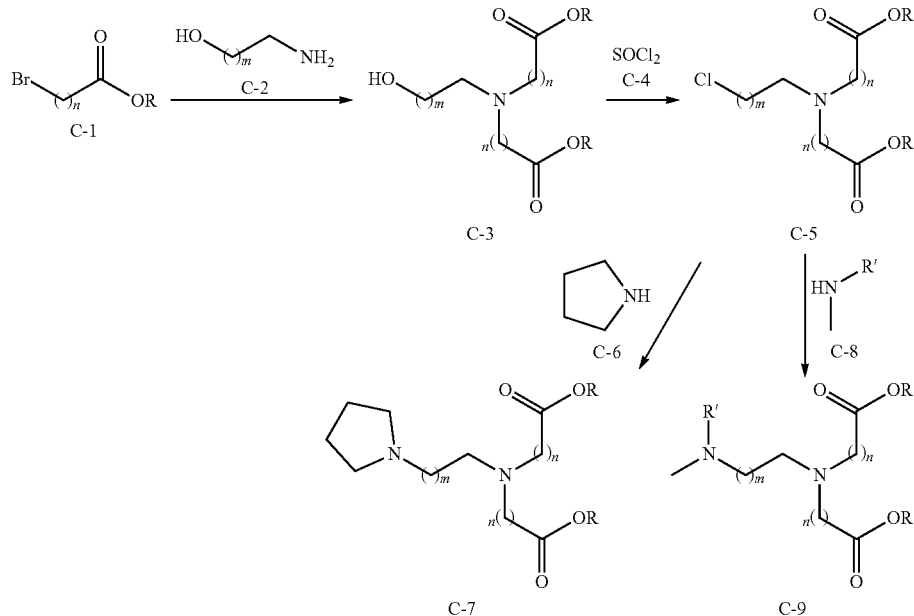

Different embodiments of the lipid of Formula (I) (e.g., compound C-7 or C9) can be prepared according to General Reaction Scheme 3 ("Method C"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 3, compounds of structure C-1 can be purchased from commercial sources or prepared according to methods familiar to one of ordinary skill in the art.

GENERAL REACTION SCHEME 4

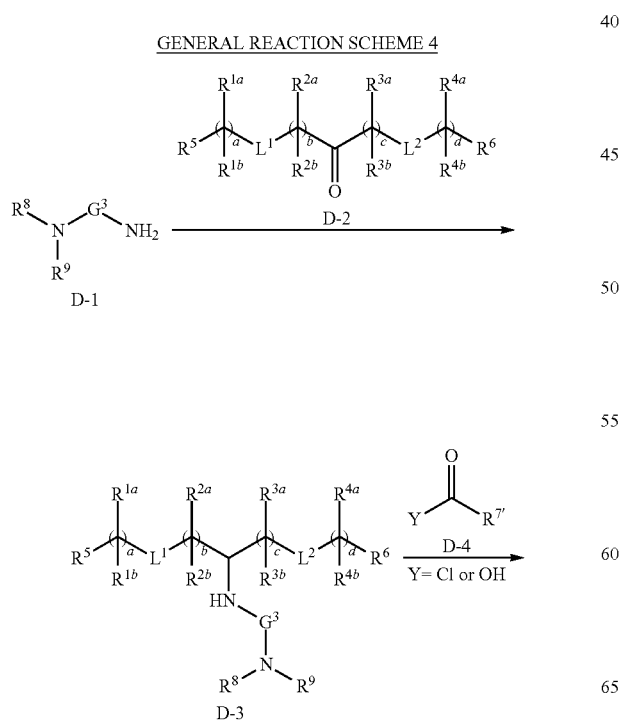

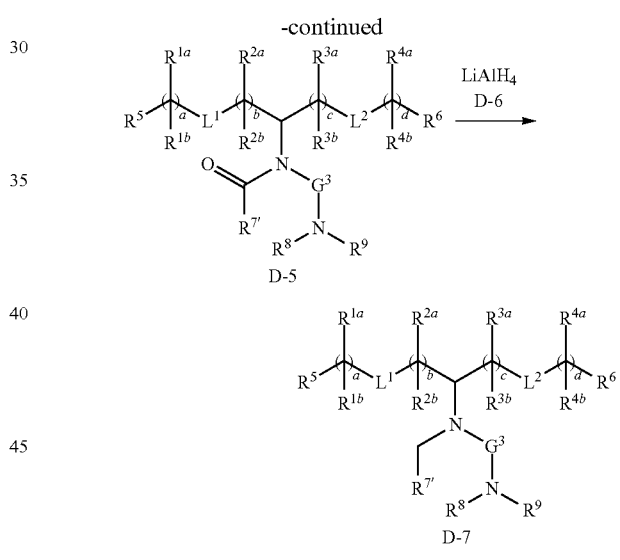

Embodiments of the compound of Formula (II) (e.g., compounds D-5 and D-7) can be prepared according to General Reaction Scheme 4 ("Method D"), wherein $R^{1a}$, Rib, $R^{2a}$, $R^{2b}$, $R^{3a}$, $R^{3b}$, $R^{4a}$, $R^{4b}$, $R^5$, $R^6$, $R^8$, $R^9$, $L^1$, $L^2$, $G^1$, $G^2$, $G^3$, a, b, c and d are as defined herein, and $R^{7'}$ represents $R^7$ or a $C_3$-$C_{19}$ alkyl. Referring to General Reaction Scheme 1, compounds of structure D-1 and D-2 can be purchased from commercial sources or prepared according to methods familiar to one of ordinary skill in the art. A solution of D-1 and D-2 is treated with a reducing agent (e.g., sodium triacetoxyborohydride) to obtain D-3 after any necessary work up. A solution of D-3 and a base (e.g. trimethylamine, DMAP) is treated with acyl chloride D-4 (or carboxylic acid and DCC) to obtain D-5 after any necessary work up and/or purification. D-5 can be reduced with LiAlH4 D-6 to give D-7 after any necessary work up and/or purification.

GENERAL REACTION SCHEME 5

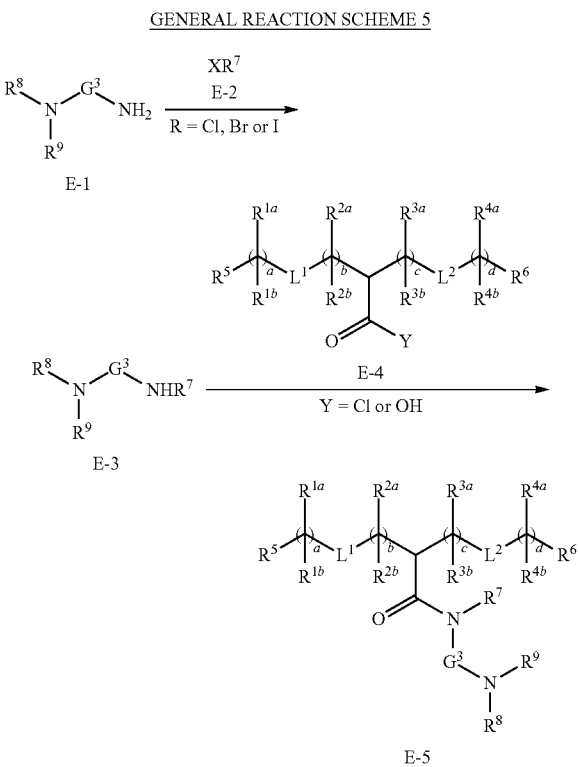

Embodiments of the lipid of Formula (II) (e.g., compound E-5) can be prepared according to General Reaction Scheme 5 ("Method E"), wherein $R^{1a}$, $R^{1b}$, $R^{2a}R^{2b}$, $R^{3a}$, $R^{3b}$, $R^{4a}$, $R^{4b}$, $R^5$, $R^6$, $R^7$, $R^8$, $R^9$, $L^1$, $L^2$, $G^3$, a, b, c and d are as defined herein. Referring to General Reaction Scheme 2, compounds of structure E-1 and E-2 can be purchased from commercial sources or prepared according to methods familiar to one of ordinary skill in the art. A mixture of E-1 (in excess), E-2 and a base (e.g., potassium carbonate) is heated to obtain E-3 after any necessary work up. A solution of E-3 and a base (e.g. trimethylamine, DMAP) is treated with acyl chloride E-4 (or carboxylic acid and DCC) to obtain E-5 after any necessary work up and/or purification.

GENERAL REACTION SCHEME 6

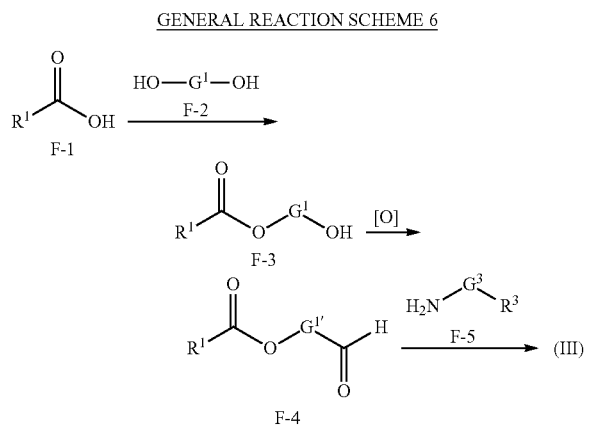

General Reaction Scheme 6 provides an exemplary method (Method F) for preparation of Lipids of Formula (III). $G^1$, $G^3$, $R^1$ and $R^3$ in General Reaction Scheme 6 are as defined herein for Formula (III), and G1' refers to a one-carbon shorter homologue of G1. Compounds of structure F-1 are purchased or prepared according to methods known in the art. Reaction of F-1 with diol F-2 under appropriate condensation conditions (e.g., DCC) yields ester/alcohol F-3, which can then be oxidized (e.g., PCC) to aldehyde F-4. Reaction of F-4 with amine F-5 under reductive amination conditions yields a lipid of Formula (III).

It should be noted that various alternative strategies for preparation of lipids of Formula (III) are available to those of ordinary skill in the art. For example, other lipids of Formula (III) wherein $L^1$ and $L^2$ are other than ester can be prepared according to analogous methods using the appropriate starting material. Further, General Reaction Scheme 6 depicts preparation of a lipids of Formula (III), wherein $G^1$ and $G^2$ are the same; however, this is not a required aspect of the invention and modifications to the above reaction scheme are possible to yield compounds wherein $G^1$ and $G^2$ are different.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intravenous, intracerebroventricular, intradermal, intramuscular, or another route of administration. Other contemplated formulations include projected nanoparticles, liposomal preparations, resealed erythrocytes containing the active ingredient, and immunogenic-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient, which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intradermal, intrasternal injection, intratumoral, intravenous, intracerebroventricular and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, In certain embodiments, the formulation may comprise dry particles which comprise the active ingredient and which have a diameter in the range from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. In certain embodiments, dry powder compositions include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain instances having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, PA), which is incorporated herein by reference.

Treatment Methods

The present invention provides methods of inducing an adaptive immune response against ZIKV in a subject comprising administering an effective amount of a composition comprising one or more isolated nucleic acids encoding one or more ZIKV antigens.

In one embodiment, the method provides immunity in the subject to ZIKV, ZIKV infection, or to a disease or disorder associated with ZIKV. The present invention thus provides a method of treating or preventing the infection, disease, or disorder associated with ZIKV.

In one embodiment, the composition is administered to a subject having an infection, disease, or disorder associated with ZIKV. In one embodiment, the composition is administered to a subject at risk for developing the infection, disease, or disorder associated with ZIKV. For example, the composition may be administered to a subject who is at risk for being in contact with a ZIKV. In one embodiment, the composition is administered to a subject who lives in, traveled to, or is expected to travel to a geographic region in which ZIKV is prevalent. In one embodiment, the composition is administered to a subject who is in contact with or expected to be in contact with another person who lives in, traveled to, or is expected to travel to a geographic region in which ZIKV is prevalent. In one embodiment, the composition is administered to a subject who has knowingly been exposed to ZIKV through their occupation or sexual contact. Exemplary geographic regions in which ZIKV is prevalent, as of 2016, include, but is not limited to, South America, Central America, Caribbean, Puerto Rico, and Florida.

In one embodiment, the composition is administered to a subject who is pregnant or who may become pregnant, in order to prevent infection, disease, or disorder associated with ZIKV in an embryo, fetus, or unborn child of the subject. For example, in certain embodiments, the composition induces an immune response against ZIKV in the embryo, fetus, or unborn child of the subject.

In one embodiment, the method comprises administering a composition comprising one or more nucleoside-modified nucleic acid molecules encoding one or more ZIKV antigens and one or more adjuvant. In one embodiment, the method comprises administering a composition comprising a first nucleoside-modified nucleic acid molecule encoding one or more ZIKV antigens and a second nucleoside-modified nucleic acid molecule encoding one or more adjuvants. In one embodiment, the method comprises administering a first composition comprising one or more nucleoside-modified nucleic acid molecules encoding one or more ZIKV antigens and administering a second composition comprising one or more nucleoside-modified nucleic acid molecules encoding one or more adjuvants.

In certain embodiments, the method comprises administering to subject a plurality of nucleoside-modified nucleic acid molecules encoding a plurality of ZIKV antigens, adjuvants, or a combination thereof.

In certain embodiments, the method of the invention allows for sustained expression of the ZIKV antigen or adjuvant, described herein, for at least several days following administration. In certain embodiments, the method of the invention allows for sustained expression of the ZIKV antigen or adjuvant, described herein, for at least 2 weeks following administration. In certain embodiments, the method of the invention allows for sustained expression of the ZIKV antigen or adjuvant, described herein, for at least 1 month following administration. However, the method, in certain embodiments, also provides for transient expression, as in certain embodiments, the nucleic acid is not integrated into the subject genome.

In certain embodiments, the method comprises administering nucleoside-modified RNA, which provides stable expression of the ZIKV antigen or adjuvant described herein. In some embodiments, administration of nucleoside-modified RNA results in little to no innate immune response, while inducing an effective adaptive immune response.

In certain embodiments, the method provides sustained protection against ZIKV. For example, in certain embodiments, the method provides sustained protection against ZIKV for more than 2 weeks. In certain embodiments, the method provides sustained protection against ZIKV for 1 month or more. In certain embodiments, the method provides sustained protection against ZIKV for 2 months or more. In certain embodiments, the method provides sustained protection against ZIKV for 3 months or more. In certain embodiments, the method provides sustained protection against ZIKV for 4 months or more. In certain embodiments, the method provides sustained protection against ZIKV for 5 months or more. In certain embodiments, the method provides sustained protection against ZIKV for 6 months or more. In certain embodiments, the method provides sustained protection against ZIKV for 1 year or more.

In one embodiment, a single immunization of the composition induces a sustained protection against ZIKV for 1 month or more, 2 months or more, 3 months or more, 4 months or more, 5 months or more, 6 months or more, or 1 year or more.

Administration of the compositions of the invention in a method of treatment can be achieved in a number of different ways, using methods known in the art. In one embodiment, the method of the invention comprises systemic administration of the subject, including for example enteral or parenteral administration. In certain embodiments, the method comprises intradermal delivery of the composition. In another embodiment, the method comprises intravenous delivery of the composition. In some embodiments, the method comprises intramuscular delivery of the composition. In one embodiment, the method comprises subcutaneous delivery of the composition. In one embodiment, the method comprises inhalation of the composition. In one embodiment, the method comprises intranasal delivery of the composition.

It will be appreciated that the composition of the invention may be administered to a subject either alone, or in conjunction with another agent.

The therapeutic and prophylactic methods of the invention thus encompass the use of pharmaceutical compositions encoding a ZIKV antigen, adjuvant, or a combination thereof, described herein to practice the methods of the invention. The pharmaceutical compositions useful for practicing the invention may be administered to deliver a dose of from 1 ng/kg/day and 100 mg/kg/day. In one embodiment, the invention envisions administration of a dose, which results in a concentration of the compound of the present invention from 10 nM and 10 µM in a mammal.

Typically, dosages which may be administered in a method of the invention to a mammal, such as a human, range in amount from 0.01 µg to about 50 mg per kilogram of body weight of the mammal, while the precise dosage administered will vary depending upon any number of factors, including but not limited to, the type of mammal and type of disease state being treated, the age of the mammal and the route of administration. In certain embodiments, the dosage of the compound will vary from about 0.1 µg to about 10 mg per kilogram of body weight of the mammal. In certain embodiments, the dosage will vary from about 1 µg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In certain embodiments, administration of an immunogenic composition or vaccine of the present invention may be performed by single administration or boosted by multiple administrations.

In one embodiment, the invention includes a method comprising administering one or more compositions encoding one or more ZIKV antigens or adjuvants described herein. In certain embodiments, the method has an additive effect, wherein the overall effect of the administering the combination is approximately equal to the sum of the effects of administering each ZIKV antigen or adjuvant. In other embodiments, the method has a synergistic effect, wherein the overall effect of administering the combination is greater than the sum of the effects of administering each ZIKV antigen or adjuvant.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Zika Virus Protection by a Single Low-Dose Nucleoside-Modified mRNA Vaccination It is demonstrated herein that a single low-dose intradermal immunization with lipid nanoparticle-encapsulated nucleoside-modified mRNA (mRNA-LNP) encoding the pre-membrane and envelope (prM-E) glycoproteins of a 2013 ZIKV outbreak strain elicited potent and durable neutralizing antibody responses in mice and non-human primates. Immunization with 30 µg of nucleoside-modified ZIKV mRNA-LNPs protected mice from ZIKV challenges at 2 weeks or 5 months post-vaccination, and a single dose of 50 µg was sufficient to protect non-human primates from a challenge at 5 weeks post-vaccination. These data demonstrate that nucleoside-modified mRNA-LNPs elicits rapid and durable protective immunity and thus represents a new and promising vaccine candidate for the global fight against ZIKV.

The methods and materials employed in these experiments are now described.

Antibody Reagents

The pan-flavivirus murine monoclonal antibody 4G2, clone D1-4G2-4-15 (EMD Millipore MAB10216) was used to detect ZIKV E protein by Western blot. The following antibodies were used for flow cytometry: anti-CD4 PerCP/Cy5.5 (Clone GK1.5, Biolegend), anti-CD3 APC-Cy7 (Clone 145-2C11, BD Biosciences), anti-CD27 PE (Clone LG.3A10, BD Biosciences), anti-TNF-α PE-Cy7 (Clone MP6-XT22, BD Biosciences), anti-IFN-γ AF700 (Clone XMG1.2, BD Biosciences), anti-IL-2 APC (Clone JES6-5H4, BD Biosciences). LIVE/DEAD Fixable Aqua Dead Cell Stain Kit (Life Technologies) was used to discriminate dead cells and debris. The following antibodies were used for ELISA assays: goat anti-mouse IgG HRP (Sigma 4416), goat anti-monkey IgG HRP (Sigma 2054), and ZIKV E protein-binding mAb NR-4747 clone E19 (BEI Resources).

Protein Reagents

Purified recombinant ZIKV E protein (Aalto Bioreagents AZ 6312) was used in ELISAs to detect E protein-specific IgG, in Western blots as a positive control and in mouse splenocyte stimulation.

mRNA Production mRNA was produced as previously described (Pardi et al, 2013, Methods Mol Biol, 969, 29-42) using T7 RNA polymerase on linearized plasmid (pTEV-ZIKVprM-E-A101) encoding codon-optimized (Thess et al., 2015, Mol Ther, 23: 1456-1464) ZIKV strain H/PF/2013 (GenBank: KJ776791) prM-E glycoproteins. mRNA was transcribed to contain 101 nucleotide-long poly(A) tails. 1-methylpseudouridine-5'-triphosphate (TriLink) instead of UTP was used to generate modified nucleoside-containing mRNA. mRNA was capped using the m7G capping kit with 2'-O-methyltransferase to obtain cap1 and was purified by a fast protein liquid chromatography (FPLC) method, as described (Weissman et al., 2013, Methods Mol Biol, 969: 43-54). mRNA was analyzed by agarose gel electrophoresis and stored frozen at −20° C.

Cell Culture

Human embryonic kidney (HEK) 293T cells (ATCC) were cultured in Dulbecco's modified Eagle's medium (DMEM) supplemented with 2 mM L-glutamine (Life Technologies) and 10% fetal calf serum (FCS) (HyClone) (complete medium). The 293T cell line was checked for mycoplasma contamination after receipt for the ATCC and before expansion and cryopreservation. Human dendritic cells (huDCs) were generated from monocytes, as described (Kariko et al, 2008, Mol Ther, 16: 1833-1840), and grown in RPMI 1640 medium containing 2 mM L-glutamine (Life Technologies) and 10% fetal calf serum (FCS) (HyClone) (complete medium) supplemented with 50 g/ml recombinant human GM-CSF and 100 μg/ml recombinant human IL-4 (R&D systems). Cells were maintained by adding fresh medium containing IL-4 and GM-CSF every 3 days and used on day 7. Murine dendritic cells (muDCs) were generated from bone marrow cells obtained from the femurs of animals and grown in complete medium supplemented with 50 μg/ml murine GM-CSF (R&D systems). Cells were maintained by adding fresh medium containing murine GM-CSF every 3 days and used on day 7.

mRNA Transfection

Transfection of human and murine DCs and HEK 293T cells was performed with TransIT-mRNA (Mirus Bio) according to the manufacturer instructions: mRNA (0.3 μg) was combined with TransIT-mRNA Reagent (0.34 μl) and Boost Reagent (0.22 μl) in 17 μl of serum free medium, and the complex was added to $2\times10^5$ cells in 183 μl complete medium. Supernatant was collected and cells were lysed for 1 hour on ice in RIPA buffer (Sigma) at 18 hours post-transfection.

Western Blot Analysis of Envelope Protein Expression

Whole cell lysates and supernatants from ZIKV prM-E transfected cells were assayed for ZIKV E protein by non-denaturing SDS-PAGE Western blot. Samples were combined with 4× Laemmli buffer (Bio-Rad) and separated on a 4-15% precast polyacrylamide Criterion TGX gel (Bio-Rad) for 45 minutes at 200 V. Transfer to PVDF membrane was performed using a semi-dry apparatus (Ellard Instrumentation, Ltd.) at 10V for 1 hour. The membrane was blocked with 5% non-fat dry milk in TBS buffer containing 0.5% Tween-20. E protein was detected using 1:10,000 4G2 ascites for 1 hour, followed by secondary goat anti-mouse IgG HRP 1:10,000 for 1 hour. Antibody incubations were performed at room temperature in blocking buffer. Blots were developed using Luminata Forte substrate (Millipore) and a Kodak X-OMAT 1000A processor. At least 2 independent experiments were performed.

Characterization of E Protein in Supernatant

Supernatant from HEK 293T cells transfected with ZIKV prM-E mRNA was tested for whether E protein could be pelleted and disrupted with detergent, consistent with subviral particles. Supernatant was incubated in PBS alone or PBS with 0.5% Triton X-100 for 1 hour on ice. Samples were then spun at 42,000 rpm for 2.5 hours in a Beckman TLA-55 rotor. The supernatant was then removed from the pellet, which was resuspended in 50 μl of PBS. Equal volumes of the input, pellet, and post-centrifugation supernatant fractions were then analyzed by Western blot, as described elsewhere herein.

Lipid Nanoparticle (LNP) Formulation of the mRNA

FPLC-purified mRNAs and polycytidylic acid (poly(C) RNA) (Sigma) were encapsulated in LNPs using a self-assembly process in which an aqueous solution of mRNA at pH 4.0 is rapidly mixed with a solution of lipids dissolved in ethanol (Maier et al., 2013, Mol Ther, 21: 1570-1578). LNPs used in this study were similar in composition to those described previously (Maier et al., 2013, Mol Ther, 21: 1570-1578; Jayaraman et al., 2012, Angew Chem Int Ed Engl, 51: 8529-8533), which contain an ionizable cationic lipid (proprietary to Acuitas)/phosphatidylcholine/cholesterol/PEG-lipid (50:10:38.5:1.5 mol/mol) and were encapsulated at an RNA to total lipid ratio of ~0.05 (wt/wt). They had a diameter of −80 nm as measured by dynamic light scattering using a Zetasizer Nano ZS (Malvern Instruments Ltd, Malvern, UK) instrument. RNA-LNP formulations were stored at −80° C. at a concentration of RNA of ~1 μg/l.

Administration of LNPs to Mice and Rhesus Monkeys

Mice: Female BALB/c and C57BL/6 mice aged 8 weeks were purchased from Charles River Laboratories, and cages of mice were randomly allocated to groups. Power analysis was used to calculate the size of all animal groups to ensure statistically significant results. mRNA-LNPs were diluted in PBS and injected into animals intradermally with a 3/10cc 29½G insulin syringe (BD Biosciences). Four sites of injection (30 μl each) over the lower back were used.

Monkeys: Ketamine anesthetized animals were shaved on their back and injected with mRNA-LNPs diluted in PBS. Ten sites of injection (60 μl each) were used. Animals of similar age and weight were randomly designated to dose groups.

Blood Collection from Mice and Rhesus Monkeys

Mice: Blood was collected from the orbital sinus under isoflurane anesthesia. Blood was centrifuged for 10 minutes at 13,000 rpm and the serum was stored at −20° C. and used for ELISA and virus neutralization assays. EDTA-plasma was collected to isolate RNA for qRT-PCR analysis.

Monkeys: Blood was collected by femoral venipuncture under ketamine anesthesia, and serum and EDTA-plasma were collected and stored at −80° C. for ELISA, neutralization analysis, and to isolate RNA for qRT-PCR.

Stimulation and Staining of Splenocytes

Single cell suspensions from spleens were made in complete medium. Splenocytes were washed once in PBS and resuspended in complete medium at $2\times10^7$ cells/ml. $2\times10^6$ cells (100 μl) per sample were stimulated for 6 hours at 37° C. using 2 μg/ml purified recombinant ZIKV virus E protein. Golgi Plug (brefeldin A, BD Biosciences) and Golgi Stop (monensin, BD Biosciences) were diluted 1:100 and 1:143 in complete medium, respectively, and 20 μl from both diluted reagents were added to each sample to inhibit the secretion of intracellular cytokines after 1 hour. An unstimulated sample for each animal was included. PMA (10 ng/ml)-ionomycin (250 ng/ml) (Sigma) stimulated samples were used as positive controls.

After stimulation, cells were washed in PBS and stained using the LIVE/DEAD Fixable Aqua Dead Cell Stain Kit (Life Technologies) and then surface stained for CD4 and CD27. Antibodies were incubated with cells for 30 min at room temperature. Following surface staining, cells were washed in FACS buffer and fixed using the Cytofix/Cytoperm kit (BD Biosciences) according to the manufacturer's instructions. Following fixation, the cells were washed in the appropriate perm buffer and incubated with antibodies against CD3, TNF-α, IFN-γ and IL-2 for 1 hour at room temperature. Following staining, the cells were washed with the appropriate perm buffer, fixed (PBS containing 1% paraformaldehyde) and stored at 4° C. until analysis. Results are obtained from one technical replicate.

Flow Cytometry

Splenocytes were analyzed on a modified LSR II flow cytometer (BD Biosciences). One hundred thousand events were collected per sample. After the gates for each function were created, the Boolean gate platform was used to create the full array of possible combination of cytokines, equating to seven response patterns when testing three functions. Data were expressed by subtracting the percent positive unstimulated cells from the percent positive cells stimulated with E protein.

Enzyme-Linked Immunosorbent Assays (ELISA) for ZIKV E-Specific IgG

Immulon 4HXB ELISA plates were coated with 6 µg/ml purified recombinant ZIKV E protein in 0.1 M sodium bicarbonate buffer overnight at 4° C. The plate was blocked with 2% BSA in PBS for 1 hour, and washed three times with wash buffer (PBS with 0.05% Tween-20). Mouse or rhesus macaque sera were diluted in blocking buffer and incubated on the plate for 1 hour at room temperature, followed by four washes. Secondary antibody HRP conjugate was diluted 1:10,000 in blocking buffer and incubated on the plate for 1 hour, followed by four washes. TMB substrate (KPL) was applied to the plate and the reaction was stopped with 2 Normal sulfuric acid. The absorbance was measured at 450 nm using an MRX Revelation microplate reader. ZIKV E-protein-specific IgG was analyzed in two ways: as an endpoint dilution titer, defined as the highest reciprocal dilution of serum to give an OD greater than the sum of the background OD plus 0.01 units; and as an estimate of the absolute IgG concentration, which was based on the murine mAb NR-4747 as a standard (applicable only to mouse samples). All samples were run at least in technical duplicates.

ZIKV MR-766 Plaque Reduction Neutralization Tests (PRNT)

ZIKV strain MR-766 (African lineage, Uganda, 1947, GenBank: AY632535) (UTMB Arbovirus Reference Collection) was produced in Vero cells (ATCC CCL-81) and 50 plaque forming units were incubated with increasing dilutions of heat-inactivated sera in serum-free DMEM (Corning) medium for 1 hour at 37° C. The virus/serum mixture (200 µl) was added to a confluent monolayer of Vero cells in 6-well format and incubated for 1.5 hour at 37° C. with intermittent rocking. Then, 3 ml of overlay, containing a final concentration of 0.5% methylcellulose (4,000 centipoise) (Sigma), 1×DMEM (Gibco), 16 mM HEPES, 0.56% sodium bicarbonate, 1.6× GlutaMAX (Gibco), 1× penicillin/streptomycin (Corning), and 4 µg/ml amphotericin B (Gibco), was added to each well, and plates were incubated for 5 days at 37° C. in 5% $CO_2$. The overlay was aspirated and cells were fixed and stained with 0.5% crystal violet (Sigma) in 25% methanol, 75% deionized water. Wells were rinsed with deionized water to visualize plaques. Neutralization titers (EC50) were determined by plotting a line through the linear portion of the curve that crossed 50% inhibition and calculating the reciprocal dilution of serum required for 50% neutralization of infection. EC50 titers are reported as the mean of one or two technical replicates and values below the limit of detection are reported as half of the limit of detection.

ZIKV MEX I-44 Focus Reduction Neutralization Tests (FRNT)

ZIKV MEX I-44 (Asian lineage, Mexico, 2016, GenBank: KX856011) stocks were generated via propagation in Vero 76 (ATCC CRL-1587) cells and harvested as clarified cell culture lysate/supernatant. Stock titers were quantified via standard focus forming assay. FRNT was performed by combining a standard dose of ZIKV with two-fold serial dilutions of heat-inactivated serum for one hour at 37° C. Virus-serum mixtures (100 µl) were then inoculated onto Vero 76 monolayers, incubated at 37° C. for 1 hour and overlayed with an Avicel (FMC Biopolymer)-containing growth medium. After 3 days of incubation, plates were formalin-fixed, permeabilized, blocked, and stained via sequential incubation with biotin-conjugated 4G2 mAb (ATCC HB-112), streptavidin-HRP (BD Biosciences) and TrueBlue Peroxidase Substrate (KPL). Virus input was verified in parallel (acceptable range: 20-60 foci). $FRNT_{50}$ ($EC_{50}$ titers) are reported as the highest reciprocal dilution giving a focus count ≤the 50% neutralization cutoff, and the geometric mean was computed for technical duplicates.

Reporter Virus Particle (RVP) Production

Pseudo-infectious RVPs were produced by complementation of a GFP-expressing WNV sub-genomic replicon (Dowd et al., 2016, Cell Rep, 16: 1485-1491; Pierson et al., 2006, Virology, 346: 53-65) with a plasmid encoding the viral structural proteins (capsid-prM-E). Briefly, ZIKV MR-766 and ZIKV H/PF/2013 RVPs were produced via co-transfection of HEK-293T cells with the structural gene and replicon plasmids (3:1 ratio by mass) using Lipofectamine 3000 per the manufacturer's protocol (Invitrogen). Transfected cells were incubated at 30° C. and RVP-containing supernatants harvested on days 3-6. Stocks were passed through a 0.2 m filter and aliquots stored at −80° C. until use. Stock titers were determined by infecting Raji-DCSIGNR cells with serial dilutions of filtered RVP supernatants. GFP-positive cells were assessed by flow cytometry at 48 hours post-infection and RVP titers calculated.

RVP Neutralization Assay

Previously titered RVPs were diluted to ensure antibody excess at informative points on the dose-response curves and incubated with serial dilutions of mouse or macaque sera for 1 hour at 37° C. to allow for steady-state binding. Raji-DCSIGNR cells were then infected with antibody-RVP complexes in duplicate technical replicates. Infections were carried out at 37° C. and GFP-positive infected cells detected by flow cytometry 24-48 hours later. Neutralization results were analyzed by non-linear regression to estimate the reciprocal dilution of sera required for half-maximal neutralization of infection ($EC_{50}$ titer) (Prism 6, GraphPad). The initial dilution of sera (based on the final volume of RVPs, cells, and sera) was set as the limit of confidence of the assay. Titers for which non-linear regression was predicted to be below this threshold were reported as a titer half the limit of confidence. Individual $EC_{50}$ titers are reported as the geometric mean of at least 2 technical replicates.

Preparation of Challenge ZIKV Virus

Mice: Challenge ZIKV strain PRVABC59 (Asian Lineage, Puerto Rico, 2016, GenBank: KU501215) (BEI Resources NR-50240) was grown in Vero CCL81 cells. A T175 flask at 75-90% confluency was inoculated with an MOI of 0.01 ZIKV in 10 ml of serum-free DMEM medium. The flask was incubated at 37° C., 5% $CO_2$ for 1.5 hours with intermittent gentle rocking, then warmed media was added to a final concentration of 1.5% FCS, 1× GlutaMAX (Gibco) and 1× penicillin/streptomycin (Corning) in a final volume of 25 ml. The flask was incubated for 4 days or until cytopathic effects were visible. Then supernatant was collected and ultra-centrifuged at 20,000 rpm for 1 hours at 4° C. in a Sorvall SureSpin 630 rotor. The supernatant was removed and the pellet was resuspended in 1 ml of serum-free DMEM, aliquoted, and stored at −80° C. Before challenge, virus was thawed and diluted in PBS to 2,000 PFU/ml.

Monkeys: Challenge ZIKV strain PRVABC59 was grown in Vero76 CRL-1587 cells. T150 flasks at 80-85% confluency were used for propagation. Infection was performed with 100 µl stock virus diluted in 4 ml of fresh L-15 media (Gibco) supplemented with 10% FCS (Gibco), 10% tryptose phosphate broth (Sigma Aldrich), 1× penicillin/streptomycin (Gibco) and L-glutamine (Gibco) and adsorbed for 1 hour at room temperature with gentle agitation every 15 minutes. Each flask received 7 ml of fresh L-15 media after adsorption and was incubated for 4 days at 37° C. Cellular debris was removed by centrifugation at 1,200 rpm for 5 minutes at 4° C. in an Eppendorf A-4-62 rotor. Virus stocks were aliquoted and stored at −80° C.

Zika Virus Challenge in Mice and Rhesus Monkeys

Mice: Two or 20 weeks after vaccination, mice were bled and then challenged intravenously with 200 PFU of ZIKV-PR (PRVABC59) in 100 µl of PBS. Blood was collected 3, 5 and 7 days post-challenge to determine viral loads (ZIKV RNA copies per ml) in plasma.

Monkeys: Macaques were anesthetized with ketamine and injected subcutaneously in the hind thigh with $10^4$ $TCID_{50}$ of ZIKV-PR in a volume of 1 ml in PBS. Blood was collected 1, 3, 5, and 7 days after the challenge to determine viral loads (ZIKV RNA copies per ml) in plasma.

Viral Load Quantification (qRT-PCR)

Using blinded samples, RNA was isolated from 200 µl (macaque) or 50 µl (mouse) of plasma using the QIAamp MinElute Virus spin kit (Qiagen). Extracted RNA was used for amplification using the SensiFAST Probe Lo-ROX One-Step Kit (Bioline BIO-78005) on a 7500 Real-Time PCR system (Applied Biosystems). Primers and probe were designed to amplify a conserved region of the capsid gene from ZIKV BeH815744, as follows: Fwd: GGAAAAAAGAGGCTATGGAAATAATAAAG (SEQ ID NO: 3); Rev: CTCCTTCCTAGCATTGATTATTCTCA (SEQ ID NO: 4); probe: AGTTCAAGAAAGATCTGGCTG (SEQ ID NO: 5). Primers and probe were used at a final concentration of 2 µM, and the following program was run: 48° C. for 30 minutes, 95° C. for 10 minutes, followed by 40 cycles of 95° C. for 15 seconds and 1 minute at 60° C. Assay sensitivity was 50 copies/ml for macaque and 200 copies/ml for mouse samples. Results are calculated from at least two technical replicates.

Statistical Analysis

GraphPad Prism 5.0f was used to perform Mann-Whitney and Kruskal-Wallis (with Dunn's correction) tests to compare immune responses in vaccinated and control mice and in different dose groups of macaques, respectively. SPICE 5.35 and Microsoft Excel software was used to perform Student's t-tests to compare T cell responses in vaccinated and control mice.

The results of the experiments are now described.

mRNA has emerged as a promising new vaccine modality that can elicit potent immune responses (reviewed in Weissman, 2015, Expert Rev Vaccines, 14: 265-281 and Sahin et al., 2014, Nat Rev Drug Discov, 13: 759-780), while avoiding the safety risks and anti-vector immunity associated with some live virus vaccines (reviewed in Minor, 2015, Virology, 479-480: 379-392). Vaccination with mRNA offers several advantages over other vaccine platforms: (I) it is a non-infectious gene vector that can be readily designed to express any protein with high efficiency, (II) mRNA does not integrate into the host genome, (III) it has the potential for cost-effective and highly scalable manufacturing, and (IV) small doses are sufficient to induce protective immune responses.

Figures 5A, 5B, 5C:
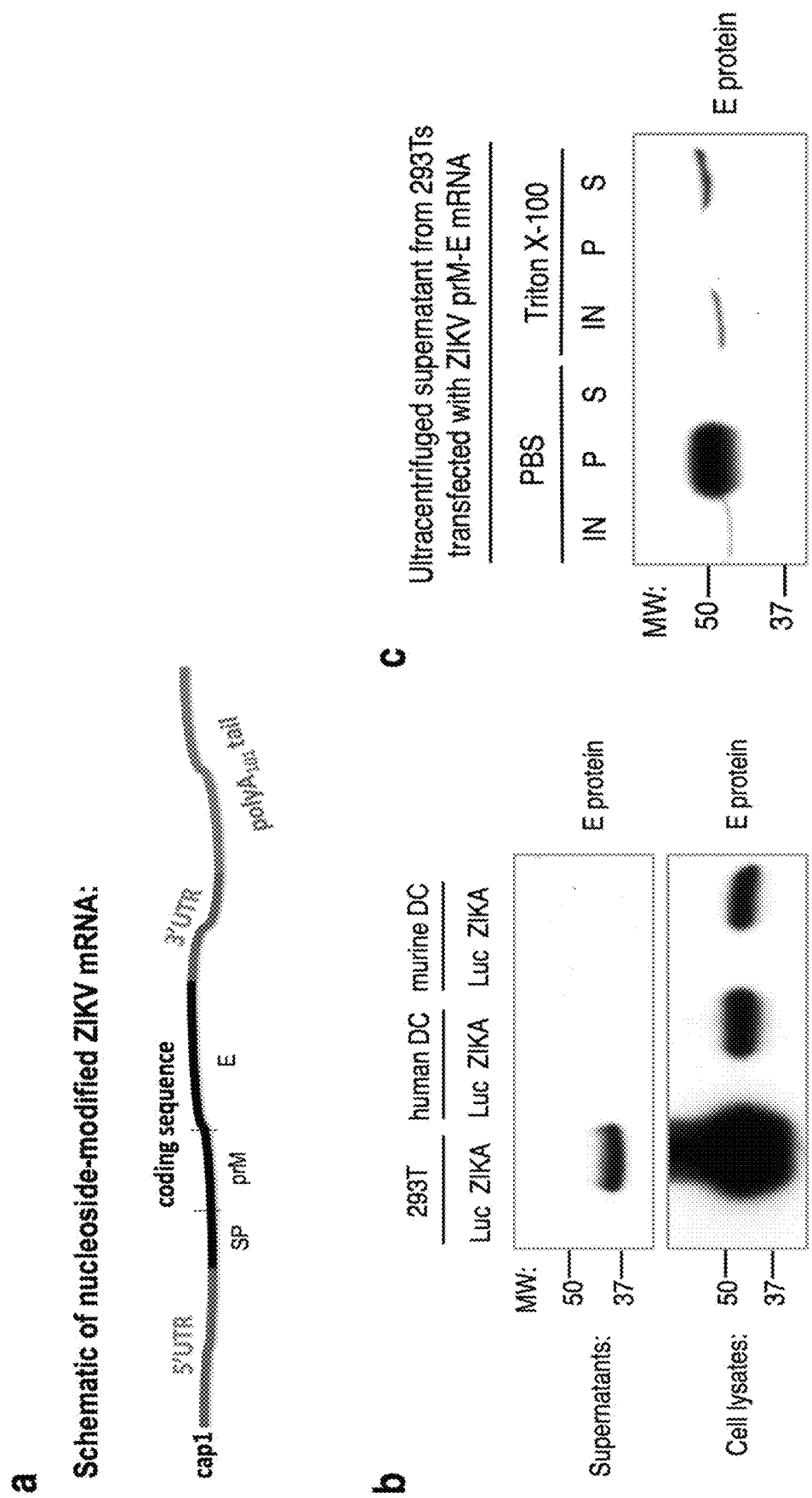
FIG. 5A through FIG. 5C depict the design and characterization of ZIKV prM-E mRNA.
Figure 6:
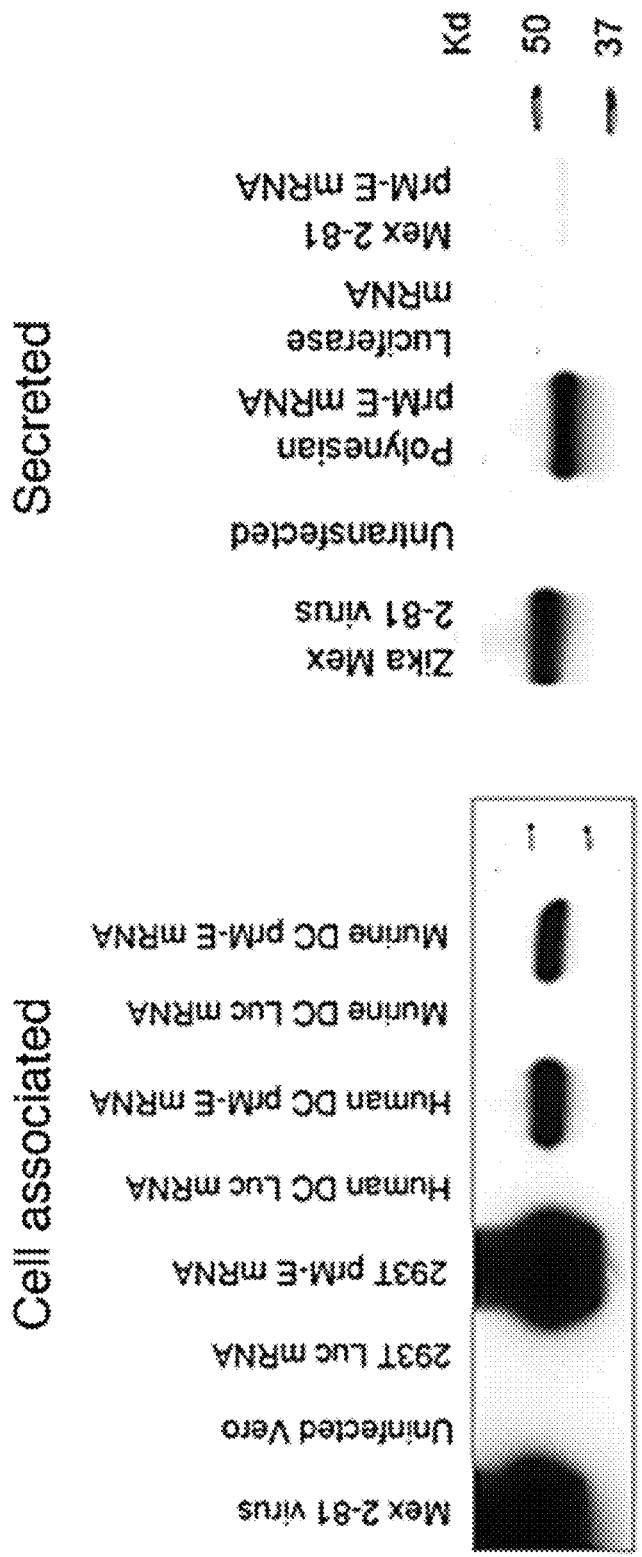
FIG. 6 depicts the results of experiments demonstrating that modified mRNA encoding ZIKV prM-E is translated and secretes subviral particles.

Presented herein is the design of a novel, potent anti-ZIKV vaccine in which the prM-E glycoproteins of ZIKV H/PF/2013 (an Asian-lineage isolate from French Polynesia, 2013) (Baronti et al., 2014, Genome Announc, 2) were encoded by mRNA containing the modified nucleoside 1-methylpseudouridine (m1Ψ), which prevents innate immune sensing and increases mRNA translation in vivo (Andries et al., 2015, J Control Release, 217: 337-344). Nucleoside-modified ZIKV prM-E mRNA was formulated for vaccination in lipid nanoparticles (LNPs), which have been shown to mediate efficient and prolonged protein expression in vivo (Pardi et al, 2015, J Control Release, 217: 345-351). Studies of ZIKV and other flaviviruses have demonstrated that co-expression of prM and E proteins is sufficient to assemble and secrete subviral particles (Dowd et al., 2016, Science, 354: 237-240; Wang et al., 2009, PLoS One 4: e8325). ZIKV prM-E-encoding mRNA was first characterized in vitro by transfecting HEK 293T cells and human and murine dendritic cells (DCs) (FIG. 5A). ZIKV E protein was produced by all three cell types and was secreted into the supernatant of 293T cells (FIG. 5B and FIG. 6). It was examined whether DCs also secrete E protein and whether it is rapidly endocytosed, as has been proposed for HIV gag (Weissman et al., 2000, J Immunol, 165: 4710-4717). To test whether E protein in 293T cell supernatant exhibited properties of subviral particles, the transfection supernatant was subjected to ultracentrifugation and probed the input, pellet, and resulting supernatant fractions for E protein. All E protein secreted from 293T cells was pelleted when incubated with PBS, but not with 0.5% Triton X-100, consistent with particle production by prM-E mRNA (Wang et al., 2009, PLoS One 4: e8325) (FIG. 5C).

Figure 7:
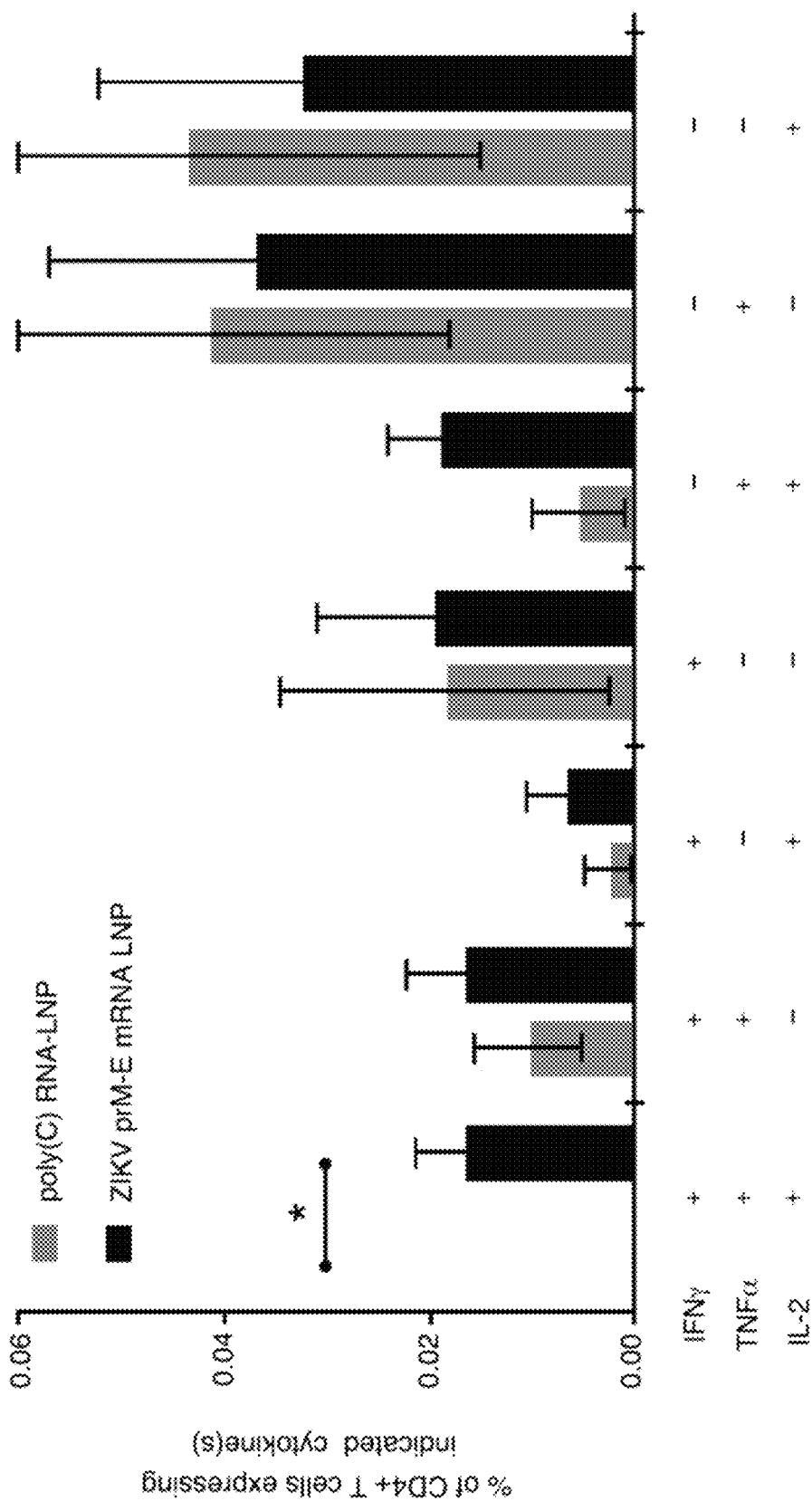
FIG. 7 depicts the results of experiments demonstrating that nucleoside-modified ZIKV mRNA-LNP immunization elicits polyfunctional ZIKV E-specific CD4+ T cell responses. C57BL/6 mice were immunized with 30 μg of nucleoside-modified ZIKV prM-E mRNA-LNP (n=8) or control poly(C) RNA-LNP (n=4). At week 2, antigen-specific CD4+ T cells were detected by intracellular cytokine staining. Bar graph shows mean frequencies of combinations of cytokines produced by CD4+ T cells. Error bars indicate the SEM, and asterisk indicates a significant difference ($p<0.05$) by Student's t-test.
Figures 8A, 8B:
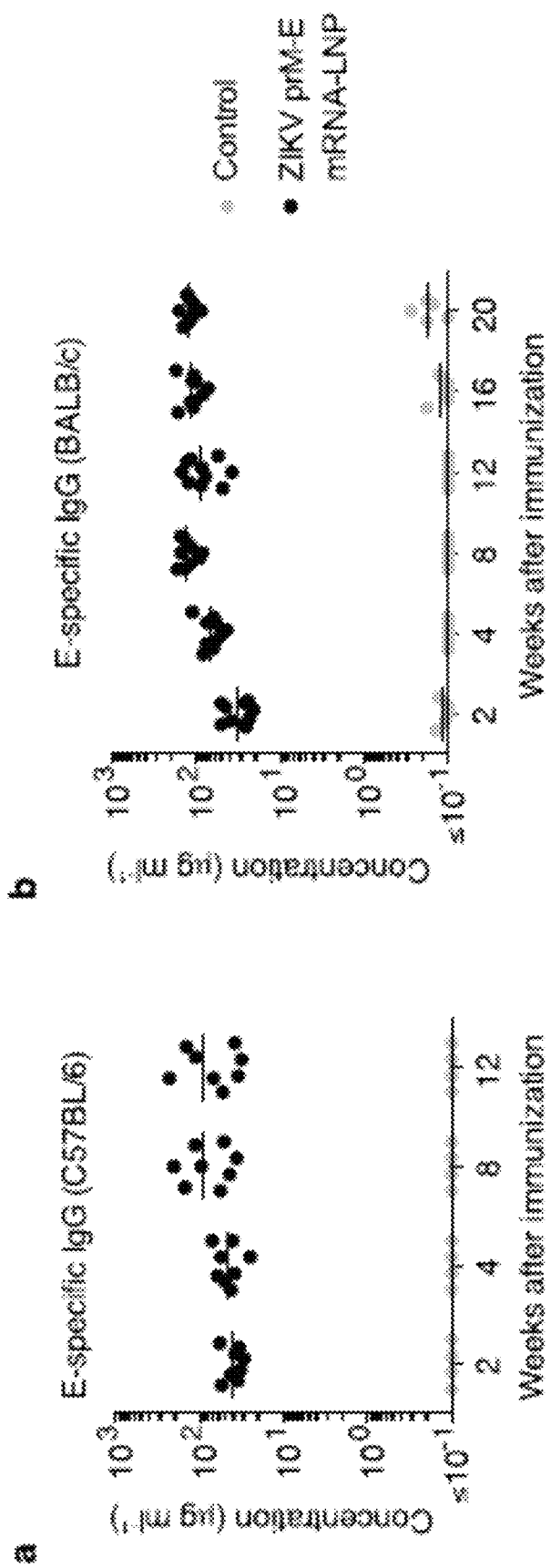
FIG. 8A and FIG. 8B depict the results of experiments measuring ZIKV E-protein specific IgG concentration in mice. Sera from immunized (FIG. 8A) C57BL/6 mice (n=4 control; n=8 ZIKV mRNA-LNP) or (FIG. 8B) BALB/c mice (n=5 control; n=10 ZIKV mRNA-LNP) were assayed by ELISA, and estimates of ZIKV E-protein-specific IgG concentrations were calculated using mouse monolconal mAb NR-4747 as a standard. Points represent individual mice; horizontal lines indicate the mean. Responses in vaccine and control groups were compared at each time point by Mann-Whitney test, $P<0.01$ for all comparisons.

The immune response induced by the nucleoside-modified ZIKV mRNA-LNP vaccine was first evaluated in C57BL/6 mice. Animals were intradermally (i.d.) immunized with 30 µg of ZIKV prM-E mRNA-LNPs or poly(C) RNA-LNP (negative control). No inflammation or other adverse events were observed at the sites of injection. Polyfunctional E protein-specific CD4+ T cell responses were detected based on intracellular IFN-γ, TNF-α, and IL-2 production by ZIKV E protein-stimulated splenocytes at week 2 post-vaccination (FIG. 1A and FIG. 7). ZIKV E-specific serum IgG developed quickly in ZIKV mRNA-vaccinated mice and stabilized at an endpoint titer of 180, 000 (~90 µg/ml) at weeks 8 to 12 (FIG. 1B and FIG. 8A). Anti-ZIKV neutralizing antibodies (NAb) were measured using two independent assays: a standard plaque reduction neutralization test (PRNT) and a ZIKV reporter viral particle (RVP) assay (Dowd et al., 2016, Science, 354: 237-240). The mean $PRNT_{50}$ titer against ZIKV MR-766 (African lineage, Uganda, 1947) peaked at ~1,300 at week 8 (FIG. 1C) and was relatively stable, with only a 2-fold reduction at week 12. The mean RVP NAb titer ($EC_{50}$) against ZIKV H/PF/2013 reached ~$10^5$ at weeks 8 and 12 (FIG. 1D). The detection of higher neutralization titers in the RVP assay relative to PRNT is consistent with a previous comparison of ZIKV neutralization assay (Dowd et al., 2016, Science, 354:

237-240). In addition, it was noted that the ratio of RVP to PRNT titers was not fixed and varies with the animal model and viral stock.

Figures 1E, 1F, 1G:
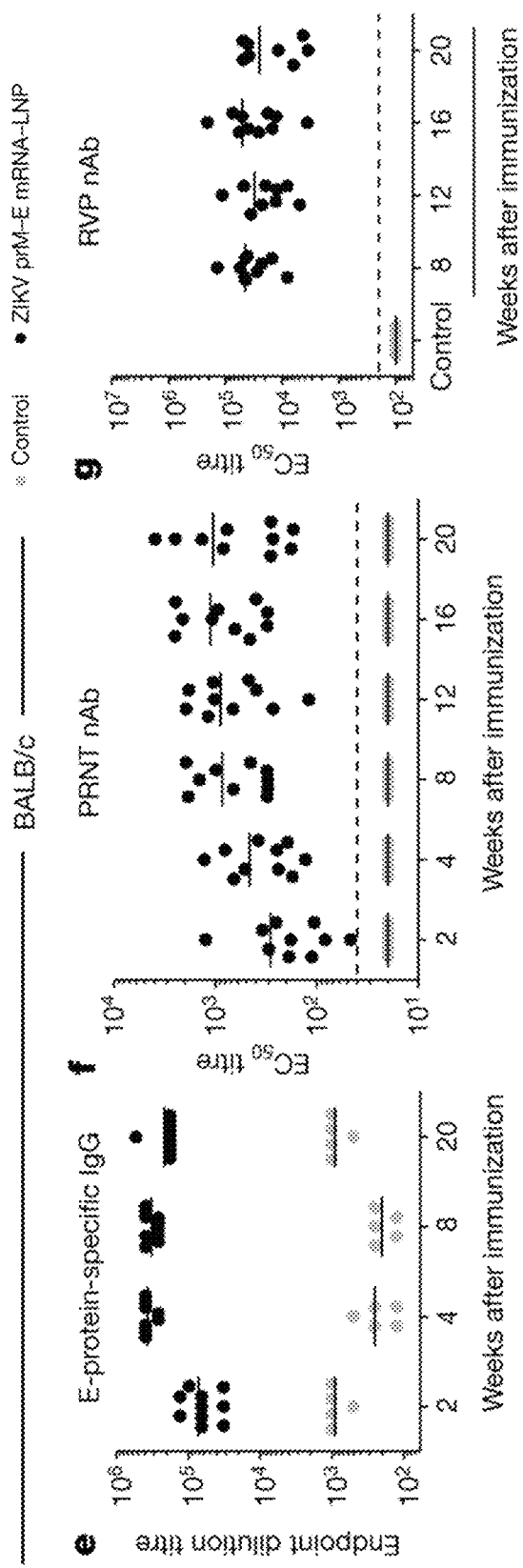

Immunogenicity of the same dose of nucleoside-modified ZIKV prM-E mRNA-LNP was next evaluated in BALB/c mice. E-specific serum IgG peaked at week 8 and remained stable between weeks 12 and 20 (endpoint titers ~200,000; 90-130 µg/ml) (FIG. 1E and FIG. 8B). $PRNT_{50}$ NAb increased to a maximum of 1,300 at week 16 and remained stable until week 20 (FIG. 1F). The RVP NAb titer rose to 50,000 at week 8 and remained above 20,000 until week 20 (FIG. 1G).

Figures 2A, 2B:
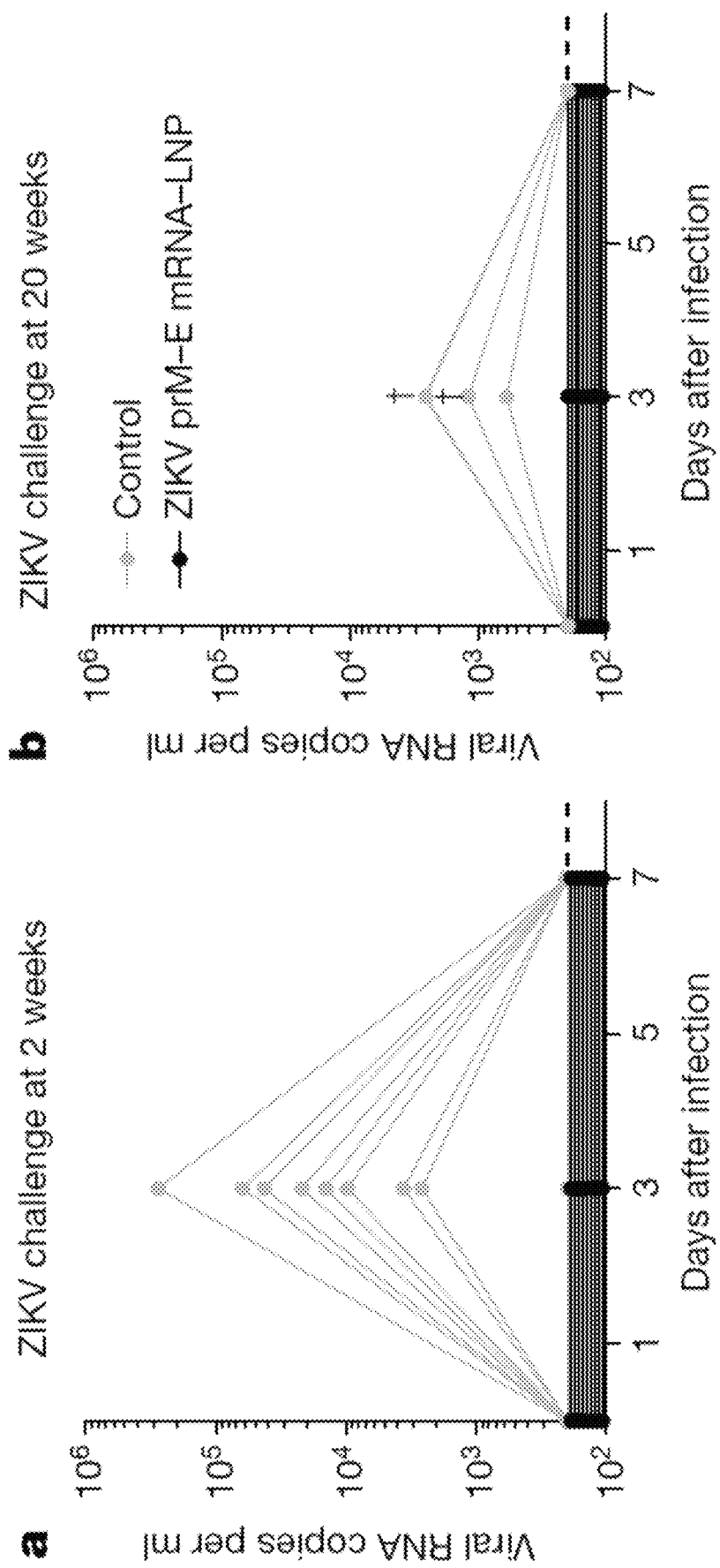
FIG. 2A and FIG. 2B depict the results of experiments demonstrating that a single immunization of nucleoside-modified ZIKV prM-E mRNA-LNP provides rapid and durable protection from ZIKV challenge in mice. BALB/c mice immunized with 30 μg of ZIKV prM-E mRNA-LNPs or control poly(C) RNA-LNPs were challenged i.v. with 200 PFU ZIKV PRVABC59 at (FIG. 2A) 2 weeks (n=9 per group) or (FIG. 2B) 20 weeks (n=5 control mice; n=10 ZIKV mRNA mice) post-vaccination, and plasma viral loads were measured by qRT-PCR for ZIKV capsid RNA. ‡ symbol indicates two overlapping curves. Dotted lines indicate the limit of detection (200 copies/ml), with undetectable curves staggered to show individual mice. Day 3 viraemia in vaccine and control groups was compared by Mann-Whitney test, $P<0.001$ for both challenges.

A challenge study was conducted in BALB/c mice immunized with 30 µg of nucleoside-modified ZIKV prM-E mRNA-LNPs or poly(C) RNA-LNPs. Mice were intravenously (i.v.) challenged at week 2 (short-term) or week 20 (long-term) post-immunization with 200 plaque-forming units (PFU) of ZIKV PRVABC59 (Asian lineage, Puerto Rico, 2015). In the short-term protection study, 8 of 9 control mice developed viremia by day 3, with a median peak of ~14,000 copies/ml. All ZIKV mRNA-immunized mice (n=9) were protected from detectable viremia (FIG. 2A). In the long-term study, all control mice (n=5) showed viremia on day 3, with a median peak of 1,200 copies/ml, while none of the ZIKV mRNA-immunized mice (n=10) had viremia at any time point tested (FIG. 2B). These data demonstrate that a single immunization with nucleoside-modified ZIKV prM-E mRNA-LNP elicits durable protection from detectable viremia with a heterologous ZIKV strain in mice.

Figures 3A, 3B, 3C:
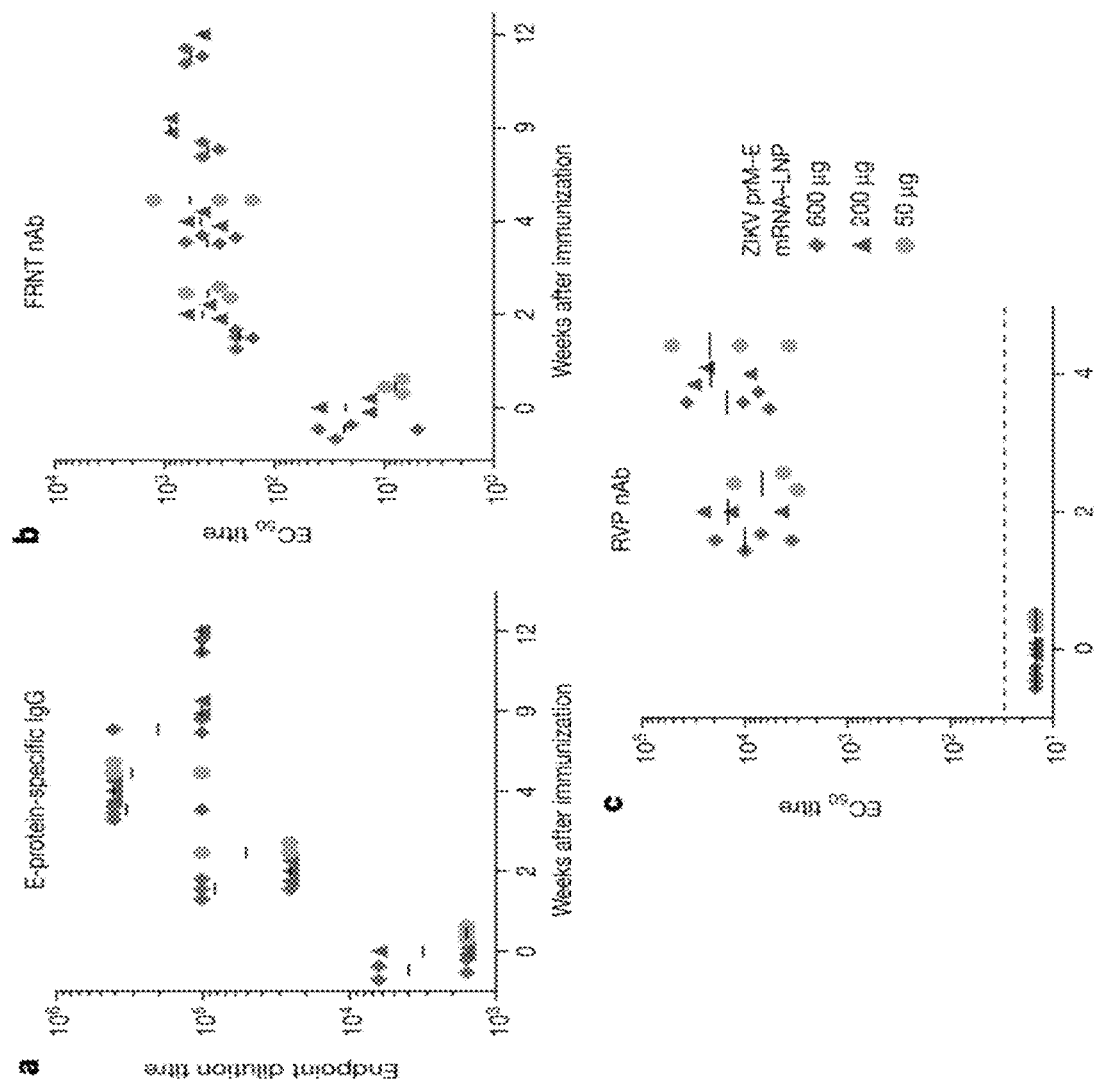
FIG. 3A through FIG. 3C depict the results of experiments demonstrating that nucleoside-modified ZIKV mRNA-LNP immunization elicits potent ZIKV-specific neutralizing antibody responses in non-human primates. Rhesus macaques were immunized with 600 μg (n=4), 200 μg (n=3), or 50 μg (n=3) of ZIKV prM-E mRNA-LNP, and the antibody response was quantified by (FIG. 3A) ELISA, (FIG. 3B) FRNT using ZIKV MEX I-44, and (FIG. 3C) RVP using ZIKV H/PF/2013. Only pre-challenge and unchallenged animal data are shown. Points represent individual monkeys; dotted lines indicate the limit of detection; horizontal lines indicate the mean. Immune responses in dose groups were compared by Kruskal-Wallis test, $P>0.05$ for all comparisons.
Figure 9:
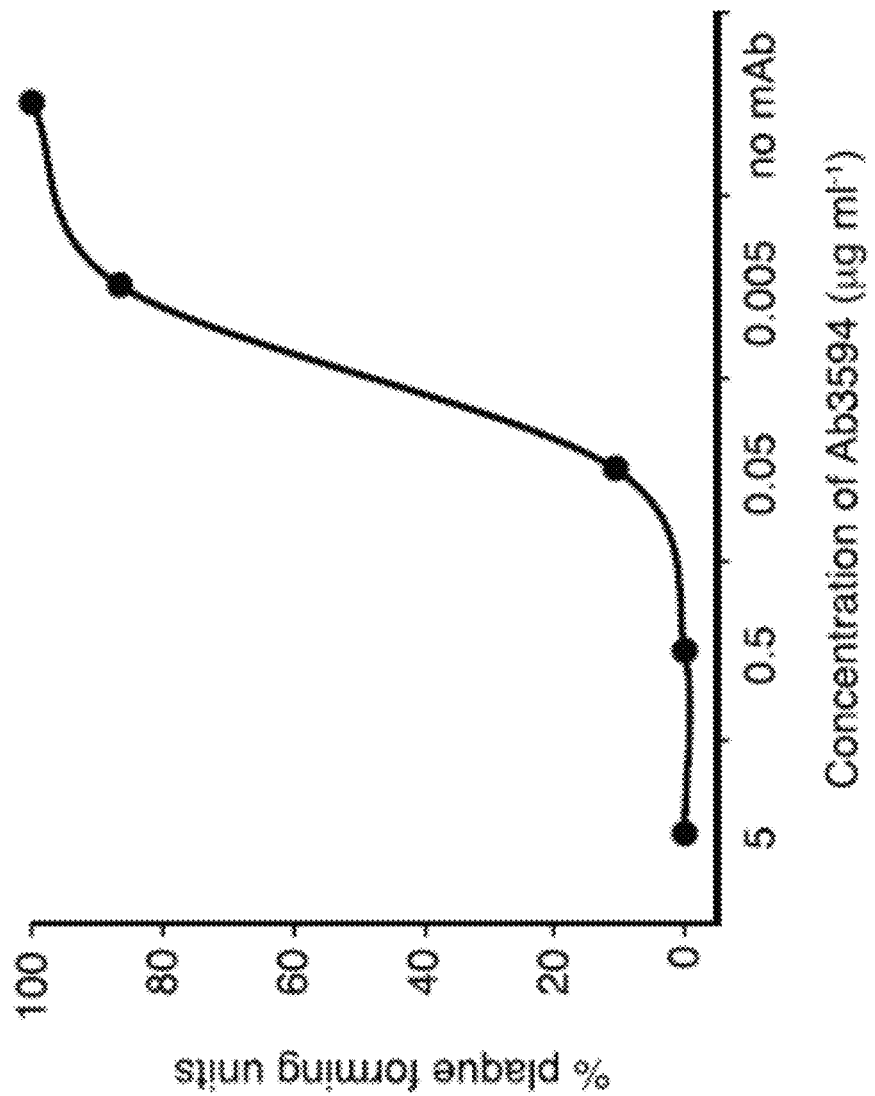
FIG. 9 depicts a neutralization curve for a human anti-ZIKV neutralizing mAb. ZIKV MR-766 was neutralized by Ab3594, a human ZIKV-neutralizing monoclonal antibody, as a positive control in the PRNT assay. Shown is a representative curve (n=4). EC50=0.026±5.4 μg ml$^{-1}$ (mean±s.d.).
Figure 10A:
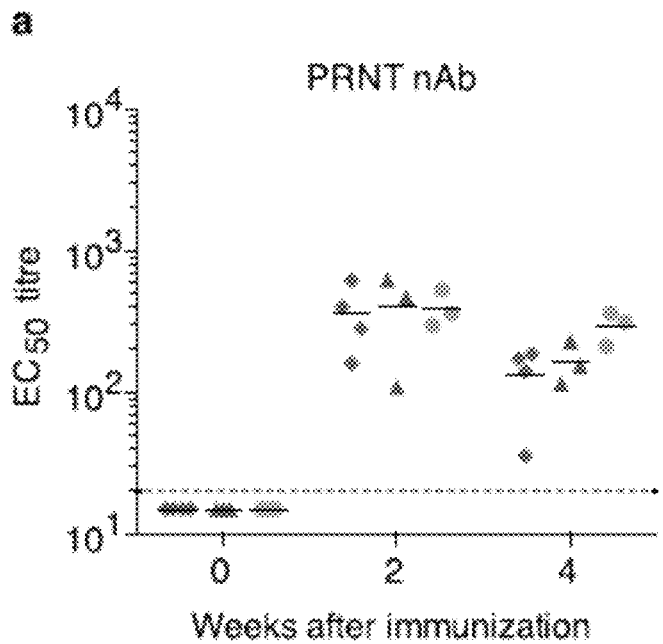
FIG. 10A and FIG. 10B depicts the results of experiments demonstrating that neutralizing antibody responses against ZIKV MR-766 in macaques immunized with ZIKV to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.
Figure 10B:
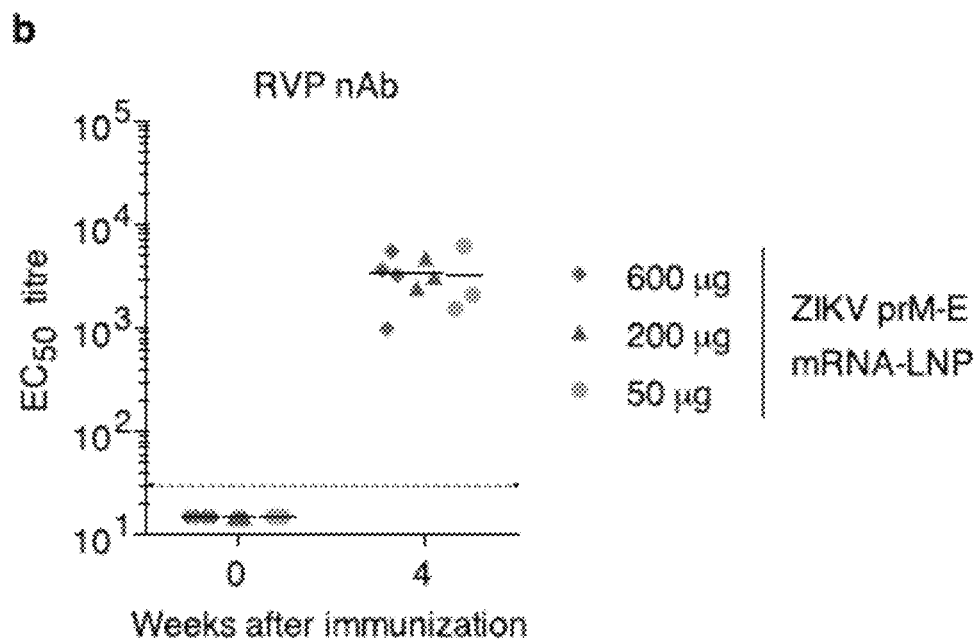

Next, the efficacy of the nucleoside-modified ZIKV mRNA-LNP vaccine was evaluated in rhesus macaques (*Macaca mulatta*), a non-human primate species that recapitulates several features of ZIKV infection in humans (Dudley et al, 2016, Nat Commun 7, 12204). Macaques were immunized by intradermal injection with doses of 600 µg, 200 µg or 50 µg of ZIKV prM-E mRNA-LNPs. Similar to mice, no inflammation or other adverse events were observed at the sites of injection. E-protein-specific IgG and NAb were efficiently induced by all three vaccine doses, with no statistically significant differences between groups. Endpoint IgG titers rose to >300,000 in all groups by week 4 and were maintained at ≥100,000 until week 12 (FIG. 3A). $PRNT_{50}$ NAb titers against MR-766 peaked at ~400 at week 2 (FIG. 10A), and stabilized at ~200 at weeks 4 through 12. To facilitate comparison of NAb titers across laboratories, the neutralization curve is shown for a human anti-ZIKV neutralizing mAb, A3594, in the PRNT assay (FIG. 9). NAb titers obtained with a focus reduction neutralization test (FRNT), which has a format similar to PRNT, were stable around 400 against ZIKV MEX I-44 (Asian lineage, Mexico, 2016) at weeks 2 and 4 (FIG. 3B). The RVP assay revealed NAb titers against H/PF/2013 of ~10,000 at week 2 and ~17,000 at week 4 (FIG. 3C), and a titer of ~3,000 against MR-766 at week 4 (FIG. 10B). The neutralization of both Asian- and African-lineage viruses is consistent with a prior report demonstrating the existence of only one serotype of ZIKV (Dowd et al., 2016, Cell Rep, 16: 1485-1491). The absence of a significant dose-dependent effect on the antibody response elicited by the nucleoside-modified ZIKV prM-E mRNA-LNP vaccine in any assay (Kruskal-Wallis test, $p>0.05$) suggests that a low dose of 50 µg (approximately 0.02 mg/kg) was sufficient, or possibly more than sufficient, to induce robust anti-ZIKV immunity in macaques.

Figure 4:
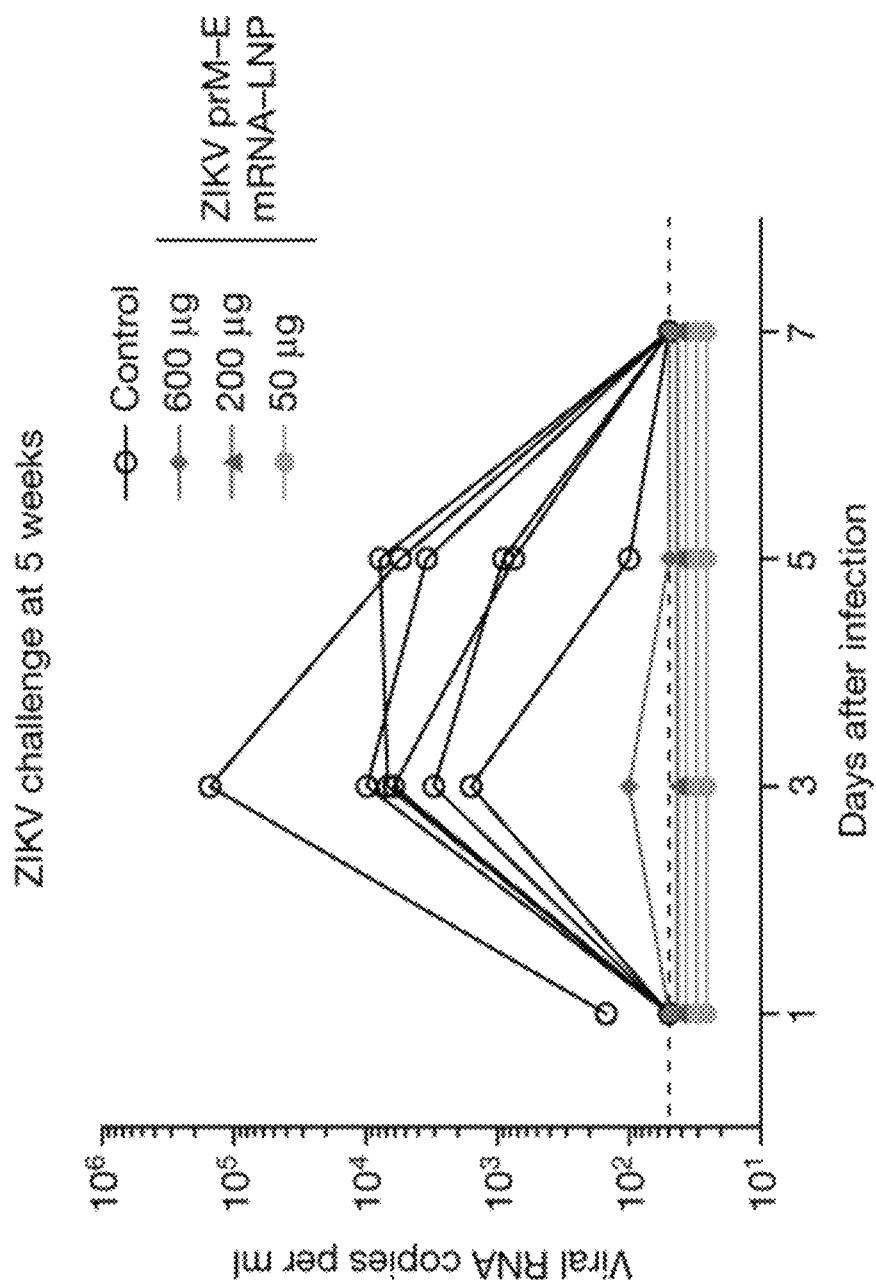
FIG. 4 depicts the results of experiments demonstrating that a single immunization of nucleoside-modified ZIKV prM-E mRNA-LNP protects rhesus macaques from ZIKV challenge at 5 weeks post-immunization. Six unvaccinated control macaques and five vaccinated macaques that received 50 μg (n=3), 200 μg (n=1), or 600 g (n=1) of ZIKV mRNA-LNP at week 0 were challenged s.c. with $10^4$ TCID50 of ZIKV PRVABC59 at week 5. Viral loads were measured in plasma by qRT-PCR for ZIKV capsid RNA. Dotted lines indicate the threshold beneath which values are below the limit of detection (50 copies per ml), and undetectable values were staggered to show individual animals. Day 3 and 5 viraemia in vaccine and control groups was compared by Mann-Whitney test, $P<0.001$.

Rhesus macaques were challenged at week 5 by subcutaneously (s.c.) injecting $10^4$ $TCID_{50}$ of ZIKV-PRVABC59 into five vaccinated animals and six unvaccinated control animals (Table 4). All control animals became infected, and median peak plasma viremia was 7,000 ZIKV RNA copies/ml (FIG. 4). In contrast, vaccinated macaques were highly protected from ZIKV infection. Four of five animals—including three that received the lowest dose of 50 µg and one that received the medium dose of 200 µg—were completely protected with no detectable viremia (<50 copies/ml) at all time points.

TABLE 4

Characteristic of rhesus macaques in vaccination and challenge experiments.
Asterisk indicates the animals that were challenged with ZIKV.

| Immunization | Group | ID | Weight (kg) | Sex | DOB |
|---|---|---|---|---|---|
| ZIKV prM-E mRNA-LNP, 600 µg | 1 | 6858 | 3.3 | M | May 19, 2014 |
| | | 150250 | 3.05 | F | Mar. 22, 2015 |
| | | 150793 | 2.55 | M | Apr. 1, 2015 |
| | | 150796 * | 2.75 | F | Apr. 13, 2015 |
| ZIKV prM-E mRNA-LNP, 200 µg | 2 | 150251 | 2.95 | M | Mar. 22, 2015 |
| | | 160795 | 2..5 | M | Apr. 12, 2015 |
| | | 150798 * | 2.35 | F | Apr. 26, 2015 |
| ZIKV prM-E mRNA-LNP, 50 µg | 3 | 6857 * | 3.15 | F | Jun. 6, 2014 |
| | | 150252 * | 2.15 | F | Mar. 25, 2015 |
| | | 150794 * | 2.75 | M | Apr. 5, 2015 |
| Challenge control group (unimmunized) | 4 | 6143 * | 7.85 | F | Jul. 3, 2000 |
| | | 6154 * | 8.95 | F | Apr. 6, 2010 |
| | | 6076 * | 7.6 | M | Oct. 20, 2011 |
| | | 6150 * | 11.55 | M | Jan. 26, 2010 |
| | | 6211 * | 8.65 | M | May 2, 2010 |
| | | 6157 * | 10.15 | F | Apr. 3, 2010 |

In this report, it is demonstrated that a single, low-dose intradermal immunization with nucleoside-modified ZIKV prM-E mRNA-LNP is protective in both mice and rhesus macaques and elicits higher NAb responses than a single immunization of multiple recently reported ZIKV vaccine candidates, including purified inactivated virus (PIV) and plasmid DNA vaccines encoding prM-E or M-E (Larocca et al., 2016, Nature, 536: 474-478; Abbink et al., 2016, Science, 353, 1129-1132; Dowd et al., 2016, Science, 354, 237-240). In mice, $PRNT_{50}$ NAb increased steadily over several months, rising to levels 50-100 times higher than those induced by a single immunization with PIV or DNA vaccines (Larocca et al., 2016, Nature, 536: 474-478; Dowd et al., 2016, Science, 354, 237-240). The ZIKV mRNA-LNP vaccine conferred complete, rapid, and durable protection in mice that was maintained for at least 5 months, and likely much longer, since NAb titers were stable. The mouse challenge studies also revealed that ZIKV PRVABC59 replicated much more efficiently (p=0.02, Mann-Whitney test) in 8-week-old BALB/c mice compared to 25-week-old mice, when two identical aliquots and doses of challenge virus stock were used. A prior report has shown that ZIKV-related mortality in immune-competent mice decreases between 1 and 4 weeks of age (Lazear et al., 2016, Cell Host Microbe, 19: 720-730), but ZIKV replication in adult mice has not yet been well described. This result may be relevant to future ZIKV vaccine testing in mice and to the understanding of ZIKV pathogenesis.

In rhesus macaques, a single immunization with 50 μg ZIKV prM-E mRNA-LNP induced RVP NAb titers that were 50 times higher than those induced by one immunization of 1 mg DNA vaccine and over 2 times higher than those induced by two immunizations of DNA (Dowd et al., 2016, Science, 354, 237-240) using the same assay run by the same lab with an identical positive control. ZIKV mRNA-LNP NAb titers may overlap with those elicited by one injection of PIV or RhAd52 ZIKV vaccines in macaques, although differing assay formats prevent a precise comparison. In contrast to viral vector vaccines, mRNA-LNP induces no anti-vector immunity, and can be administered repeatedly without loss of immunogenicity. The FRNT nAb titres elicited by ZIKV mRNA-LNP in macaques were maintained at a stable level until 12 weeks after immunization, suggesting that protection may be durable.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for inducing an immune response against Zika virus (ZIKV) in a subject, the composition comprising at least one mRNA molecule encoding at least one ZIKV antigen, wherein the mRNA molecule comprises a sequence having at least 95% identity to the nucleotide sequence of SEQ ID NO: 1.

2. The composition of claim 1, wherein the composition further comprises an adjuvant.

3. The composition of claim 1, wherein the mRNA molecule further encodes at least one adjuvant.

4. The composition of claim 1, further comprising a lipid nanoparticle (LNP).

5. The composition of claim 1, wherein the at least one mRNA molecule is encapsulated within an LNP.

6. The composition of claim 1, wherein the composition is a vaccine.

7. A method of inducing an adaptive immune response against Zika virus (ZIKV) in a subject comprising administering to the subject an effective amount of the composition of claim 1.

8. The method of claim 7, wherein the method further comprises administering to the subject an effective amount of an adjuvant.

9. The method of claim 7, wherein the at least one mRNA molecule is encapsulated within an LNP.

10. The method of claim 7, wherein the composition is a vaccine.

11. The method of claim 7, wherein the composition is administered by a delivery route selected from the group consisting of intradermal, subcutaneous, inhalation, intranasal, and intramuscular.

12. The method of claim 7, wherein the method comprises a single administration of the composition.

13. The method of claim 7, wherein the method comprises multiple administrations of the composition.

14. A method of treating or preventing an infection, disease, or disorder associated with ZIKV in at least one selected from the group consisting of the subject and an unborn child of the subject, the method comprising administering to the subject the composition of claim 1.

15. The method of claim 14, wherein the at least one mRNA molecule comprises at least one modified nucleoside selected from the group consisting of pseudouridine, and 1-methyl-pseudouridine.

16. The method of claim 14, wherein the composition further comprises an adjuvant.

17. The method of claim 14, wherein the at least one mRNA molecule further encodes at least one adjuvant.

18. The method of claim 14, further comprising a lipid nanoparticle (LNP).

19. The method of claim 14, wherein the at least one mRNA is encapsulated within an LNP.

20. The method of claim 14, wherein the composition is a vaccine.

21. The method of claim 14, wherein the composition is administered by a delivery route selected from the group consisting of intradermal, subcutaneous, inhalation, intranasal, and intramuscular.

22. The method of claim 14, wherein the method comprises a single administration of the composition.

23. The method of claim 14, wherein the method comprises multiple administrations of the composition.

* * * * *

SEQUENCE LISTING

<160> NUMBER OF SEQ ID NOS: 5

<210> SEQ ID NO 1
<211> LENGTH: 2094
<212> TYPE: DNA
<213> ORGANISM: Artificial Sequence
<220> FEATURE:
<223> OTHER INFORMATION: chemically synthesized

<400> SEQUENCE: 1

```
atggccataa gtggagtccc ggtgctagga ttcttcatca tagccgtgct gatgagcgcg      60
caggaatcat gggccgccga ggtgacgaga cggggagcg catactacat gtacttggac     120
agaaacgacg ccggggaggc catatccttc ccaaccacat tggggatgaa caagtgttac     180
atacagatca tggacctggg acacatgtgc gacgccacca tgagctacga atgccctatg     240
ctggacgagg gggtggaacc agacgacgtc gactgctggt gcaacacgac gtcaacttgg     300
gtggtgtacg gaacctgcca ccacaaaaaa ggcgaagcac ggagatcgag acgggccgtg     360
acgctcccct cccactccac gaggaagctg caaacgcggt cgcaaacctg gttggaatca     420
agagaataca caaagcactt gatcagagtc gaaaactgga tattcaggaa ccctggcttc     480
gcgttagcag cagccgccat cgcttggctg ttgggaagct caacgagcca aaaagtcata     540
tacttggtca tgatactgct gatcgccccg gcatacagca tcaggtgcat aggagtcagc     600
aacagggact tcgtggaagg gatgtcaggc gggacctggg tggacgtggt cttggaacac     660
ggagggtgcg tcaccgtaat ggcacaggac aaaccgacgg tcgacataga gctggttaca     720
acaacagtca gcaacatggc ggaggtaaga tcctactgct acgaggcatc aatatcggac     780
atggcgtcgg acagccgctg cccaacacaa ggcgaagcct acctggacaa gcaatcagac     840
acgcaatacg tctgcaaaag aacgttagtg gacagaggct ggggaaacgg atgcggactg     900
ttcggcaaag ggagcctggt gacatgcgcc aagttcgcat gctccaagaa aatgaccggg     960
aagagcatcc agccagagaa cctggagtac cggataatgc tgtcagtgca cggctcccag    1020
cacagcggga tgatcgtgaa cgacacagga cacgaaacgg acgagaacag agcgaaggtg    1080
gagataacgc ccaactcacc aagagccgaa gccaccctgg ggggcttcgg aagcctagga    1140
ctggactgcg aaccgaggac aggcctcgac ttctcagact tgtactactt gacgatgaac    1200
aacaagcact ggttggtgca caggagtgg ttccacgaca tcccattacc ttggcacgcc    1260
```

-continued

```
gggcagaca ccggaacgcc acactggaac aacaaagaag cactggtaga gttcaaggac    1320
gcacacgcca aaaggcaaac ggtcgtggtc ctagggagcc aagaaggagc agtgcacacg    1380
gccctggccg gagcgctgga ggccgagatg gacggggcaa agggaaggct gtcctccggc    1440
cacttgaaat gccgcctgaa aatggacaaa ctgagattga agggcgtgtc atactccttg    1500
tgcaccgcag cgttcacatt caccaagatc ccggcggaaa cactgcacgg acagtcaca    1560
gtggaggtac agtacgcagg acagacgga ccgtgcaagg tgccagcgca gatggcggtg    1620
gacatgcaaa ccctgacccc agtcgggagg ttgataaccg cgaaccccgt aatcacggaa    1680
agcaccgaga actcgaagat gatgctggaa ctcgatccac cattcgggga ctcgtacatc    1740
gtcataggag tcggggagaa gaagatcacc caccactggc acaggagcgg cagcaccatc    1800
ggaaaagcat cgaagccac ggtgagaggg gccaagagaa tggcagtctt gggagacaca    1860
gcctgggact tcggatcagt cggaggcgcg ctcaactcat gggcaaggg catccaccaa    1920
atcttcggag cagctttcaa atcattgttc ggaggaatgt cctggttctc acaaatcctc    1980
atcggaacgt tgctgatgtg gttggggctg aacacaaaga acggatcgat ctccctgatg    2040
tgcttggcct tagggggagt gttgatcttc ttatccacag cggtctccgc gtaa          2094
```

<210> SEQ ID NO 2
<211> LENGTH: 697
<212> TYPE: PRT
<213> ORGANISM: Artificial Sequence
<220> FEATURE:
<223> OTHER INFORMATION: chemically synthesized

<400> SEQUENCE: 2

```
Met Ala Ile Ser Gly Val Pro Val Leu Gly Phe Phe Ile Ile Ala Val
1               5                   10                  15

Leu Met Ser Ala Gln Glu Ser Trp Ala Ala Glu Val Thr Arg Arg Gly
            20                  25                  30

Ser Ala Tyr Tyr Met Tyr Leu Asp Arg Asn Asp Ala Gly Glu Ala Ile
        35                  40                  45

Ser Phe Pro Thr Thr Leu Gly Met Asn Lys Cys Tyr Ile Gln Ile Met
    50                  55                  60

Asp Leu Gly His Met Cys Asp Ala Thr Met Ser Tyr Glu Cys Pro Met
65                  70                  75                  80

Leu Asp Glu Gly Val Glu Pro Asp Asp Val Asp Cys Trp Cys Asn Thr
                85                  90                  95

Thr Ser Thr Trp Val Val Tyr Gly Thr Cys His His Lys Lys Gly Glu
            100                 105                 110

Ala Arg Arg Ser Arg Arg Ala Val Thr Leu Pro Ser His Ser Thr Arg
        115                 120                 125

Lys Leu Gln Thr Arg Ser Gln Thr Trp Leu Glu Ser Arg Glu Tyr Thr
    130                 135                 140

Lys His Leu Ile Arg Val Glu Asn Trp Ile Phe Arg Asn Pro Gly Phe
145                 150                 155                 160

Ala Leu Ala Ala Ala Ala Ile Ala Trp Leu Leu Gly Ser Ser Thr Ser
                165                 170                 175

Gln Lys Val Ile Tyr Leu Val Met Ile Leu Leu Ile Ala Pro Ala Tyr
            180                 185                 190

Ser Ile Arg Cys Ile Gly Val Ser Asn Arg Asp Phe Val Glu Gly Met
        195                 200                 205

Ser Gly Gly Thr Trp Val Asp Val Val Leu Glu His Gly Gly Cys Val
```

```
            210                 215                 220
Thr Val Met Ala Gln Asp Lys Pro Thr Val Asp Ile Glu Leu Val Thr
225                 230                 235                 240

Thr Thr Val Ser Asn Met Ala Glu Val Arg Ser Tyr Cys Tyr Glu Ala
                245                 250                 255

Ser Ile Ser Asp Met Ala Ser Asp Ser Arg Cys Pro Thr Gln Gly Glu
                260                 265                 270

Ala Tyr Leu Asp Lys Gln Ser Asp Thr Gln Tyr Val Cys Lys Arg Thr
            275                 280                 285

Leu Val Asp Arg Gly Trp Gly Asn Gly Cys Gly Leu Phe Gly Lys Gly
        290                 295                 300

Ser Leu Val Thr Cys Ala Lys Phe Ala Cys Ser Lys Lys Met Thr Gly
305                 310                 315                 320

Lys Ser Ile Gln Pro Glu Asn Leu Glu Tyr Arg Ile Met Leu Ser Val
                325                 330                 335

His Gly Ser Gln His Ser Gly Met Ile Val Asn Asp Thr Gly His Glu
                340                 345                 350

Thr Asp Glu Asn Arg Ala Lys Val Glu Ile Thr Pro Asn Ser Pro Arg
            355                 360                 365

Ala Glu Ala Thr Leu Gly Gly Phe Gly Ser Leu Gly Leu Asp Cys Glu
        370                 375                 380

Pro Arg Thr Gly Leu Asp Phe Ser Asp Leu Tyr Tyr Leu Thr Met Asn
385                 390                 395                 400

Asn Lys His Trp Leu Val His Lys Glu Trp Phe His Asp Ile Pro Leu
                405                 410                 415

Pro Trp His Ala Gly Ala Asp Thr Gly Thr Pro His Trp Asn Asn Lys
                420                 425                 430

Glu Ala Leu Val Glu Phe Lys Asp Ala His Ala Lys Arg Gln Thr Val
            435                 440                 445

Val Val Leu Gly Ser Gln Glu Gly Ala Val His Thr Ala Leu Ala Gly
        450                 455                 460

Ala Leu Glu Ala Glu Met Asp Gly Ala Lys Gly Arg Leu Ser Ser Gly
465                 470                 475                 480

His Leu Lys Cys Arg Leu Lys Met Asp Lys Leu Arg Leu Lys Gly Val
                485                 490                 495

Ser Tyr Ser Leu Cys Thr Ala Ala Phe Thr Phe Thr Lys Ile Pro Ala
            500                 505                 510

Glu Thr Leu His Gly Thr Val Thr Val Glu Val Gln Tyr Ala Gly Thr
        515                 520                 525

Asp Gly Pro Cys Lys Val Pro Ala Gln Met Ala Val Asp Met Gln Thr
530                 535                 540

Leu Thr Pro Val Gly Arg Leu Ile Thr Ala Asn Pro Val Ile Thr Glu
545                 550                 555                 560

Ser Thr Glu Asn Ser Lys Met Met Leu Glu Leu Asp Pro Pro Phe Gly
                565                 570                 575

Asp Ser Tyr Ile Val Ile Gly Val Gly Glu Lys Lys Ile Thr His His
                580                 585                 590

Trp His Arg Ser Gly Ser Thr Ile Gly Lys Ala Phe Glu Ala Thr Val
            595                 600                 605

Arg Gly Ala Lys Arg Met Ala Val Leu Gly Asp Thr Ala Trp Asp Phe
        610                 615                 620

Gly Ser Val Gly Gly Ala Leu Asn Ser Leu Gly Lys Gly Ile His Gln
625                 630                 635                 640
```

```
Ile Phe Gly Ala Ala Phe Lys Ser Leu Phe Gly Gly Met Ser Trp Phe
                645                 650                 655

Ser Gln Ile Leu Ile Gly Thr Leu Leu Met Trp Leu Gly Leu Asn Thr
            660                 665                 670

Lys Asn Gly Ser Ile Ser Leu Met Cys Leu Ala Leu Gly Gly Val Leu
            675                 680                 685

Ile Phe Leu Ser Thr Ala Val Ser Ala
    690                 695

<210> SEQ ID NO 3
<211> LENGTH: 29
<212> TYPE: DNA
<213> ORGANISM: Artificial Sequence
<220> FEATURE:
<223> OTHER INFORMATION: chemically synthesized

<400> SEQUENCE: 3
ggaaaaaaga ggctatggaa ataataaag                                    29

<210> SEQ ID NO 4
<211> LENGTH: 26
<212> TYPE: DNA
<213> ORGANISM: Artificial Sequence
<220> FEATURE:
<223> OTHER INFORMATION: chemically synthesized

<400> SEQUENCE: 4
ctccttccta gcattgatta ttctca                                       26

<210> SEQ ID NO 5
<211> LENGTH: 21
<212> TYPE: DNA
<213> ORGANISM: Artificial Sequence
<220> FEATURE:
<223> OTHER INFORMATION: chemically synthesized

<400> SEQUENCE: 5
agttcaagaa agatctggct g                                            21
```